Patent Number: 5,770,600
Date of Patent: Jun. 23, 1998

United States Patent [19]
Abelman et al.

[54] METHIONINE SULFONE AND S-SUBSTITUTED CYSTEINE SULFONE DERIVATIVES AS ENZYME INHIBITORS

[75] Inventors: Matthew Mark Abelman, Solana Beach; Robert John Ardecky, Encinitas; Ruth Foelsche Nutt, San Diego, all of Calif.

[73] Assignee: Corvas International, Inc., San Diego, Calif.

[21] Appl. No.: 473,647

[22] Filed: Jun. 6, 1995

Related U.S. Application Data

[63] Continuation of Ser. No. 423,584, Apr. 18, 1995, which is a continuation-in-part of Ser. No. 234,811, Apr. 28, 1994, which is a continuation-in-part of Ser. No. 229,298, Apr. 18, 1994.

[51] Int. Cl.$^6$ .......... A61K 31/535; A61K 31/445; C07D 401/12; C07D 413/12

[52] U.S. Cl. .......... 514/237.2; 544/129; 544/130; 544/132; 544/141; 546/186; 546/188; 546/189; 546/190; 546/191; 546/208; 546/210; 514/236.2; 514/326; 514/316

[58] Field of Search .......... 544/141; 546/208; 514/237.2, 326

[56] References Cited

U.S. PATENT DOCUMENTS

| | | | |
|---|---|---|---|
| 5,439,888 | 8/1995 | Shuman et al. | 514/18 |
| 5,484,772 | 1/1996 | Sall et al. | 514/18 |
| 5,488,037 | 1/1996 | Sall et al. | 514/19 |
| 5,498,779 | 3/1996 | Neises et al. | 514/428 |

*Primary Examiner*—Johann Richter
*Assistant Examiner*—Laura L. Stockton
*Attorney, Agent, or Firm*—Lyon & Lyon

[57] ABSTRACT

This invention relates to compounds which inhibit thrombin or factor Xa. The compounds contain an aldehyde functionality and a methionine sulfone or S-substituted cysteine sulfone residue. The compounds and their pharmaceutical compositions are useful for preventing thrombosis in mammals which are suspected of having a condition characterized by abnormal thrombosis.

24 Claims, 3 Drawing Sheets

METHIONINE SULFONE AND S-SUBSTITUTED CYSTEINE SULFONE DERIVATIVES AS ENZYME INHIBITORS

RELATED APPLICATIONS

This is a continuation of application Ser. No. 08/423,584, filed Apr. 18, 1995 which is a continuation-in-part of U.S. Ser. No. 08/234,811, filed Apr. 28, 1994 which is a continuation-in-part of U.S. Ser. No. 08/229,298, filed Apr. 18, 1994 the disclosures of which are hereby incorporated by reference herein, including the drawings attached thereto.

TECHNICAL FIELD

In one aspect, the present invention relates to compounds which are potent inhibitors of thrombin or factor Xa. In another aspect, the present invention relates to novel peptide aldehyde analogs, their pharmaceutically acceptable salts, and pharmaceutically acceptable compositions thereof which are useful as potent and specific inhibitors of blood coagulation in vitro and in vivo in mammals. In yet another aspect, the invention relates to methods of using these inhibitors as therapeutic agents for disease states in mammals characterized by abnormal thrombosis.

BACKGROUND

Normal hemostasis is the result of a complex balance between the processes of clot formation (blood coagulation) and clot dissolution (fibrinolysis). The complex interactions between blood cells, specific plasma proteins and the vascular surface, maintain the fluidity of blood unless injury and blood loss occur.

Blood coagulation is the culmination of a series of amplified reactions in which several specific zymogens of serine proteases in plasma are activated by limited proteolysis. Nemerson, Y. and Nossel, H. L., Ann. Rev. Med., 33: 479 (1982). This series of reactions results in the formation of an insoluble fibrin matrix which is required for the stabilization of the primary hemostatic plug. The interaction and propagation of the activation reactions occurs through the extrinsic and intrinsic pathways of coagulation.

These pathways are highly inter-dependent and converge in the formation of the serine protease, Factor Xa. Factor Xa catalyzes the penultimate step in the blood coagulation cascade which is the formation of the serine protease thrombin. This step occurs following the assembly of the prothrombinase complex which is composed of factor Xa, the non-enzymatic co-factor Va and the substrate prothrombin assembled on the surface of adhered, activated platelets or systemically circulating membranous microparticles.

Proteolytic activation of zymogen factor X to its catalytically active form, factor Xa, can occur by either the intrinsic or extrinsic coagulation pathways.

The intrinsic pathway is referred to as "intrinsic" because everything needed for clotting is in the blood. Saito, H., "Normal Hemostatic Mechanisms", Disorders of Hemostasis, pp. 27–29, Grune & Stratton, Inc. (O. D. Ratnoff, M.D. and C. D. Forbes, M.D. edit. 1984). This pathway is comprised of the zymogen serine proteases, factors IX and XI, and the non-enzymatic co-factor, factor VIII. The initiation of the intrinsic pathway results in the activation of factor XI to XIa. Factor XIa catalyzes the activation of factor IX to factor IXa which in combination with the activated form of factor VIII on an appropriate phospholipid surface, results in the formation of the tenase complex. This complex also catalyzes the formation of the serine protease, factor Xa, from its zymogen, factor X which subsequently results in clot formation.

The extrinsic pathway is referred to as "extrinsic" because the tissue factor which binds to and facilitates the activation of factor VII comes from outside the blood. Saito, Id. The major components of this pathway are the zymogen serine protease, factor VII, and the membrane bound protein, tissue factor. The latter serves as the requisite non-enzymatic co-factor for this enzyme. The initiation of this pathway is thought to be an autocatalytic event resulting from the activation of zymogen factor VII by trace levels of activated factor VII (factor VIIa), both of which are bound to newly exposed tissue factor on membrane surfaces at sites of vascular damage. The factor VIIa/tissue factor complex directly catalyzes the formation of the serine protease, factor Xa, from its zymogen, factor X. Exposure of blood to injured tissue initiates blood clotting by the extrinsic pathway.

The formation of thrombin is catalyzed by factor Xa following the assembly of the catalytic prothrombinase complex as reviewed by Mann, K. G. et. al., "Surface-Dependent Reactions of the Vitamin K-Dependent Enzyme Complexes", Blood, 76: 1–16 (1990). This complex is composed of factor Xa, the non-enzymatic co-factor Va and the substrate prothrombin all assembled on an appropriate phospholipid surface. The requirement of a macromolecular complex for efficient catalysis results in the protection of factor Xa from natural anticoagulant mechanisms such as heparin-antithrombin III mediated inhibition. Teite, J. M. and Rosenberg, R. D., "Protection of Factor Xa from neutralization by the heparin-antithrombin complex", J. Clin. Invest., 71: 1383–1391(1983). In addition, sequestration of factor Xa in the prothrombinase complex also renders it resistant to inhibition by exogenous heparin therapy which also requires antithrombin III to elicit its anticoagulant effect.

Thrombin is the primary mediator of thrombus formation. Thrombin acts directly to cause formation of insoluble fibrin from circulating fibrinogen. In addition, thrombin activates the zymogen factor XIII to the active transglutaminase factor XIIIa which acts to covalently stabilize the growing thrombus by crosslinking the fibrin strands. Lorand, L. and Konishi, K., Arch. Biochem. Biophys., 105: 58 (1964). Beyond its direct role in the formation and stabilization of fibrin rich clots, the enzyme has been reported to have profound bioregulatory effects on a number of cellular components within the vasculature and blood. Shuman, M. A., Ann. NY Acad. Sci., 405: 349 (1986).

It is believed that thrombin is the most potent agonist of platelet activation, and it has been demonstrated to be the primary pathophysiologic-mediator of platelet-dependent arterial thrombus formation. Edit, J. F. et al., J. Clin. Invest., 84: 18 (1989). Thrombin-mediated platelet activation leads to ligand-induced inter-platelet aggregation principally due to the bivalent interactions between adhesive ligands such as fibrinogen and fibronectin with platelet integrin receptors such as glycoprotein IIb/IIIa which assume their active conformation following thrombin activation. Berndt, M. C. and Phillips, D. R., Platelets in Biology and Pathology, pp 43–74, Elsevier/North Holland Biomedical Press (Gordon, J. L. edit. 1981). Thrombin-activated platelets can also support further thrombin production through the assembly of new prothrombinase and tenase (factor IXa, factor VIIIa and factor X) catalytic complexes on the membrane surface of intact activated platelets and platelet-derived microparticles, following thrombin-mediated activation of the non-enzymatic cofactors V and VIII, respectively. Tans, G. et al., Blood, 77: 2641 (1991). This positive feedback process results in the local generation of large concentrations of thrombin within the vicinity of the thrombus which supports further thrombus growth and extension. Mann, K. G. et al., Blood, 76: 1 (1990).

In contrast to its prothrombotic effects, thrombin has been shown to influence other aspects of hemostasis. These include its effect as an important physiological anticoagulant. The anticoagulant effect of thrombin is expressed following binding of thrombin to the endothelial cell membrane glycoprotein, thrombomodulin. This is thought to result in an alteration of the substrate specificity of thrombin thereby allowing it to recognize and proteolytically activate circulating protein C to give activated protein C (aPC). Musci, G. et al., Biochemistry, 27: 769 (1988). aPC is a serine protease which selectively inactivates the non-enzymatic co-factors Va and VIIIa resulting in a down-regulation of thrombin formation by the prothrombinase and tenase catalytic complexes, respectively. Esmon, C. T., Science, 235: 1348 (1987). The activation of protein C by thrombin in the absence of thrombomodulin is poor.

Thrombin has also been shown to be a potent direct mitogen for a number of cell types, including cells of mesenchymal origin such as vascular smooth muscle cells. Chen, L. B. and Buchanan, J. M., Proc. Natl. Acad. Sci. USA, 72: 131 (1975). The direct interaction of thrombin with vascular smooth muscle also results in vasoconstriction. Walz, D. A. et al., Proc. Soc. Expl. Biol. Med., 180: 518 (1985). Thrombin acts as a direct secretagogue inducing the release of a number of bioactive substances from vascular endothelial cells including tissue plasminogen activator. Levin, E. G. et al., Thromb. Haemost., 56: 115 (1986). In addition to these direct effects on vascular cells, the enzyme can indirectly elaborate potent mitogenic activity on vascular smooth muscle cells by the release of several potent growth factors (e.g. platelet-derived growth factor and epidermal growth factor) from platelet a-granules following thrombin-induced activation. Ross, R., N. Engl. J. Med., 314: 408 (1986).

Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively. Ross, A. M., Thrombosis in Cardiovascular Disorder, p. 327, W. B. Saunders Co. (Fuster, V. and Verstraete, M. edit. 1991); Califf, R. M. and Willerson, J. T., Id. at p 389. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. Heparin, the most widely used clinical anticoagulant administered i.v., has not been shown to be universally effective in the treatment or prevention of acute arterial thrombosis or rethrombosis. Prins, M. H. and Hirsh, J., J. Am. Coll. Cardiol., 67: 3A (1991).

Besides the unpredictable, recurrent thrombotic reocclusion which commonly occurs following PTCA, a profound restenosis of the recanalized vessel occurs in 30 to 40% of patients 1 to 6 months following this procedure. Califf, R. M. et al., J. Am. Coll. Cardiol., 17: 2B (1991). These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

The need for safe and effective therapeutic anticoagulants has in one aspect focused on the role of the serine protease thrombin in blood coagulation.

Most preferred natural substrates for thrombin are reported to contain an uncharged amino acid in the P3 recognition subsite. For example, the thrombin cleavage site on the Aα chain of fibrinogen, which is the primary physiological substrate for thrombin, is reported to contain a glycine residue in this position while the cleavage site on the Bβ chain contains a serine, as shown below:

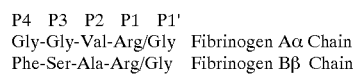

```
P4  P3  P2  P1  P1'
Gly-Gly-Val-Arg/Gly    Fibrinogen Aα Chain
Phe-Ser-Ala-Arg/Gly    Fibrinogen Bβ Chain
```

Peptidyl derivatives having an uncharged residue in the P3 position are said to bind to the active site of thrombin and thereby inhibit the conversion of fibrinogen to fibrin and cellular activation have been reported. These derivatives have either an aldehyde, chloromethyl ketone or boronic acid functionality associated with the P1 amino acid. For example, substrate-like peptidyl derivatives such as D-phenylalanyl-prolyl-argininal (D-Phe-Pro-Arg-al), D-phenylalanyl-prolyl-arginine-chloromethyl ketone (P-PACK) and acetyl-D-phenylalanyl-prolyl-boroarginine (Ac-(D-Phe)-Pro-boroArg) have been reported to inhibit thrombin by directly binding to the active site of the enzyme. Bajusz, S., Symposia Biologica Hungarica, 25: 277 (1984), Bajusz, S. et al, J. Med. Chem., 33: 1729 (1990) and Bajusz, S. et al., Int. J. Peptide Protein Res. 12: 217 (1970); Kettner, C. and Shaw, E., Methods Enzymol., 80: 826 (1987), Kettner, C. et al., EP 293,881 (published Dec. 7, 1988), Kettner, C., et al., J. Biol. Chem., 265: 18209 (1990). These molecules have been reported to be potent anticoagulants in the prevention of platelet-rich arterial thrombosis. Kelly, A. B. et al., Thromb. Haemostas., 65: 736 at abstract 257 (1991). Other peptidyl aldehydes have been proposed or reported as inhibitors of thrombin. Bey, P. et al., EP 363,284 (published Apr. 11, 1990) and Balasubramanian, N. et al., EP 526,877 (published Feb. 10, 1993).

Peptidyl compounds which are said to be active site inhibitors of thrombin but which differ in structure from those containing a uncharged amino acid in the P3 recognition subsite have been reported.

The compound, Argatroban (also called 2R,4R-4-methyl-1-[N-2-(3-methyl-1,2,3,4-tetrahydro-8-quinolinesulfonyl)-L-argininal]-2-piperdinecarboxylic acid), is also reported to bind directly to the active site of thrombin and has been thought to be the most potent and selective compound in the class of non-peptidyl inhibitors of this enzyme. Okamoto, S. et al., Biochem. Biophys. Res. Commun., 101: 440 (1981). Argatroban has been reported to be a potent antithrombotic agent in several experimental models of acute arterial thrombosis. Jang, I. K. et al., in both Circulation, 81: 219 (1990) and Circ. Res., 67: 1552 (1990).

Peptidyl compounds which are said to be inhibitors of thrombin and whose mode of action is thought to be by binding to both the active site and another site on the enzyme have been reported. Hirudin and certain peptidyl derivatives of hirudin have been reported to inhibit both conversion of fibrinogen to fibrin and platelet activation by binding to either both the active site and exo site, or the exo site only, of thrombin. Markwardt, F., Thromb. Haemostas., 66: 141 (1991). Hirudin is reported to be a 65 amino acid polypeptide originally isolated from leech salivary gland extracts. It is said to be one of the most potent inhibitors of thrombin known. Marki, W. E. and Wallis, R. B., Thromb. Haemostas., 64: 344 (1990). It has been reported to inhibit thrombin by binding to both its anion-binding exo-site and to its catalytic active site which are distinct and physically distant from each other. Rydel, T. J. et al., Science, 249: 277 (1990). Hirudin has been reported to be a potent antithrombotic agent in vivo. Markwardt, F. et al., Pharmazie, 43: 202 (1988); Kelly, A. B. et al., Blood, 77: 1 (1991). In addition to its antithrombotic effects, hirudin has been reported to also effectively inhibit smooth muscle proliferation and the associated restenosis following mechanical damage to a atherosclerotic rabbit femoral artery. Sarembock, I. J. et al., Circulation, 84: 232 (1991).

Hirugen has been reported to be a peptide derived from the anionic carboxy-terminus of hirudin. It is reported to bind only to the anion binding exo-site of thrombin and thereby inhibit the formation of fibrin but not the catalytic turnover of small synthetic substrates which have access to the unblocked active site of the enzyme. Maraganore, J. M. et al., J. Biol. Chem., 264: 8692 (1989); Naski, M. C. et al., J. Biol. Chem., 265: 13484 (1990). The region of hirudin represented by hirugen has been reported, as according to by x-ray crystallographic analysis, to bind directly to the exo site of thrombin. Skrzypczak-Jankun, E. et al., Thromb. Haemostas., 65: 830 at abstract 507 (1991). Moreover, the binding of hirugen has also been reported to enhance the catalytic turnover of certain small synthetic substrates by thrombin, indicating that a conformational change in the enzyme active site may accompany occupancy of the exo-site. Liu, L. W. et al., J. Biol. Chem, 266: 16977 (1991). Hirugen also is reported to block thrombin-mediated platelet aggregation. Jakubowski, J. A. and Maraganore, J. M., Blood, 75: 399 (1990).

A group of synthetic chimeric molecules comprised of a hirugen-like sequence linked by a glycine-spacer region to the peptide, D-phenylalanyl-prolyl-arginine, which is based on a preferred substrate recognition site for thrombin, has been termed to be hirulog. Maraganore et al., U.S. Pat. No. 5,196,404 (Mar. 23, 1993). The hirugen-like sequence is said to be linked to this peptide through the C-terminal end of the peptide. Maraganone, J. M. et al., Biochemistry, 29: 7095 (1990). The hirulogs have been reported to be an effective antithrombotic agents in preventing both fibrin-rich and platelet-rich thrombosis. Maraganone, J. M. et al., Thromb. Haemostas., 65: 651 at abstract 17 (1991).

SUMMARY OF THE INVENTION

In one aspect, the present invention is directed to compounds which are useful in vitro and in vivo as antithrombic agents.

According to a preferred aspect, the peptide aldehydes of the present invention include those depicted in formula (I) below:

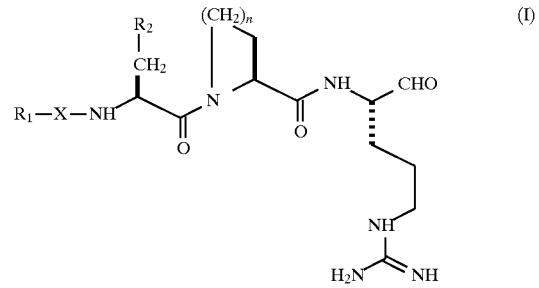

wherein (a) X is selected from the group consisting of —C(O)—, —O—C(O)—, —NH—C(O)—, —S(O$_2$)—, —O—S(O$_2$)—, —NH—S(O$_2$)— and —N(R')—S(O$_2$)—, wherein R' is alkyl of 1 to about 4 carbon atoms, aryl of about 6 to about 14 carbon atoms, or aralkyl of about 6 to about 15 carbon atoms;

(b) R$_1$ is selected from the group consisting of:
  (1) alkyl of about 3 to about 10 carbon atoms,
  (2) alkyl of 1 to about 3 carbon atoms substituted with cyclic alkyl of about 5 to about 8 carbon atoms,
  (3) alkenyl of about 3 to about 6 carbon atoms,
  (4) alkenyl of about 3 to about 6 carbon atoms which is substituted with cyclic alkyl of about 5 to about 8 carbon atoms,
  (5) aryl of about 6 to about 14 carbon atoms,
  (6) aryl of about 6 to about 14 carbon atoms which is substituted with Y$_1$,
  (7) aryl of about 6 to about 14 carbon atoms which is substituted with Y$_1$ and Y$_2$, or Y$_1$ and Y$_2$ and Y$_3$,
  (8) aralkyl of about 6 to about 15 carbon atoms,
  (9) aralkyl of about 6 to about 15 carbon atoms which is substituted in the aryl ring with Y$_1$,
  (10) aralkyl of about 6 to about 15 carbon atoms which is substituted in the aryl ring with Y$_1$ and Y$_2$, or Y$_1$ and Y$_2$ and Y$_3$,
  (11) aralkenyl of about 8 to about 15 carbon atoms,
  (12) aralkenyl of about 8 to about 15 carbon atoms which is substituted in the aryl ring with Y$_1$,
  (13) aralkenyl of about 8 to about 15 carbon atoms which is substituted in the aryl ring with Y$_1$ and Y$_2$, or Y$_1$ and Y$_2$ and Y$_3$,
  (14) perfluoroalkyl of 1 to about 12 carbon atoms,
  (15) perfluoroaryl of about 6 to about 14 carbon atoms,
  (16) trimethylsilylalkyl of about 4 to about 8 carbon atoms,

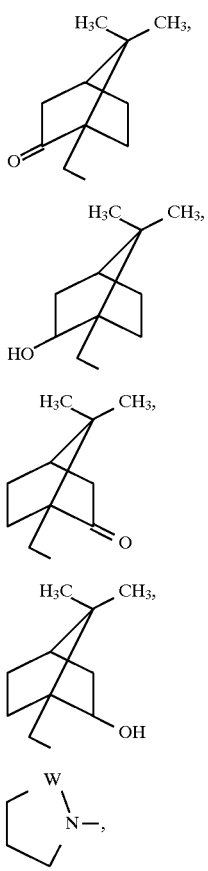

(17)

(18)

(19)

(20)

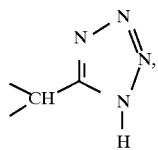

(21)

wherein W is oxygen, methylene, —C(O)—, —CH(OH)—, —CH(OA$_1$)—, —CH(C(O)—OH)—, —CH(C(O)—OR')—, —CH(C(O)—NHR')—, —CH(C(O)—NR'R")—,

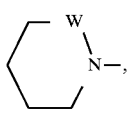

—NH— or —N(R')—, and X is not —O—C(O)—, —NH—C(O)—, —O—S(O$_2$)—, —NH—S(O$_2$)— or —N(R')—S(O$_2$)—, (22)

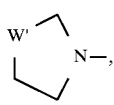

where X is not —O—C(O)—, —NH—C(O)—, —O—S(O$_2$)—, —NH—S(O$_2$)— or —N(R')—S(O$_2$)—, (23)

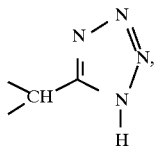

wherein W' is oxygen, sulfur, —S(O)—, —S(O$_2$)—, methylene, —C(O)—, —CH(OH)—, —CH(OA$_1$)—, —CH(C(O)—OH)—, —CH(C(O)—OR')—, —CH(C(O)—NHR')—, —CH(C(O)—NR'R")—,

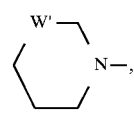

—NH— or —N(R')—, and X is not —O—C(O)—, —NH—C(O)—, —O—S(O$_2$)—, —NH—S(O$_2$)— or —N(R')—S(O$_2$)—, (24)

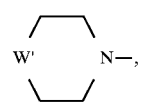

where X is not —O—C(O)—, —NH—C(O)—, —O—S(O$_2$)—, —NH—S(O$_2$)— or —N(R')—S(O$_2$)—, (25)

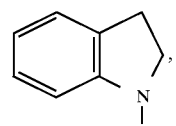

where X is not —O—C(O)—, —NH—C(O)—, —O—S(O$_2$)—, —NH—S(O$_2$)— or —N(R')—S(O$_2$)—, (26)

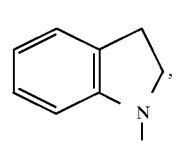

where X is not —O—C(O)—, —NH—C(O)—, —O—S(O$_2$)—, —NH—S(O$_2$)— or —N(R')—S(O$_2$)—,

(27) a substituted group of the formula

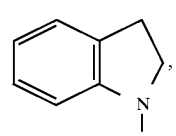

wherein the aryl ring is substituted with Y$_1$, and X is not —O—C(O)—, —NH—C(O)—, —O—S(O$_2$)—, —NH—S(O$_2$)— or —N(R')—S(O$_2$)—, and

(28) a substituted group of the formula wherein the aryl ring is substituted with Y$_1$ and Y$_2$, and X is not —O—C(O)—, —NH—C(O)—, —O—S(O$_2$)—, —NH—S(O$_2$)— or —N(R')—S(O$_2$)—, wherein Y$_1$, Y$_2$ and Y$_3$ are independently selected from the group consisting of bromo, chloro, fluoro, —Z$_1$, —OH, —OZ$_1$, —NH$_2$, —NHZ$_1$, —NZ$_1$Z$_2$, —NH—C(O)—Z$_1$, —N(Z$_1$)—C(O)—Z$_2$, —NH—C(O)—OZ$_1$, —N(Z$_1$)—C(O)—OZ$_2$, —NH—C(O)—NH$_2$, —NH—C(O)—NHZ$_1$, —NH—C(O)—NZ$_1$Z$_2$, —N(Z$_1$)—C(O)—NHZ$_2$, —N(Z$_1$)—C(O)—NZ$_2$Z$_3$, —C(O)—OH, —C(O)—OZ$_1$, —C(O)—NHZ$_1$, —C(O)—NZ$_1$Z$_2$, —SH, —SZ$_1$, —S(O)—Z$_1$, —S(O$_2$)—Z$_1$, —S(O$_2$)—OH, —S(O$_2$)—OZ$_1$, —S(O$_2$)—NH$_2$, —S(O$_2$)—NHZ$_1$, —S(O$_2$)—NZ$_1$Z$_2$ and

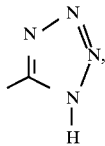

wherein Z$_1$, Z$_2$ and Z$_3$ are independently selected from the group consisting of trifluoromethyl, pentafluoroethyl, alkyl of 1 to about 12 carbon atoms, aryl of about 6 to about 14 carbon atoms, and aralkyl of about 6 to about 15 carbon atoms, R" is alkyl of 1 to about 4 carbon atoms, aryl of about 6 to about 14 carbon atoms, or aralkyl of about 6 to about 15 carbon atoms, A$_1$ is aryl of about 6 to about 14 carbon atoms, aryl of about 6 to about 14 carbon atoms which is substituted with Y$_1$, aralkyl of about 6 to about 15 carbon atoms, or aralkyl of about 6 to about 15 carbon atoms which is substituted with Y$_1$;

(c) R$_2$ is selected from the group consisting of
—CH$_2$—S(O)$_q$—CH$_3$,
—CH$_2$—S(O)$_q$—(CH$_2$)$_m$—C(O)—OH,
—CH$_2$—S(O)$_q$—(CH$_2$)$_m$—C(O)—OR',
—CH$_2$—S(O)$_q$—(CH$_2$)$_m$—C(O)—NH$_2$,
—CH$_2$—S(O)$_q$—(CH$_2$)$_m$—C(O)—NHR',
—CH$_2$—S(O)$_q$—(CH$_2$)$_m$—C(O)—NR'R",

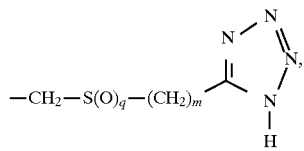

—CH$_2$—S(O)$_q$—(CH$_2$)$_m$—Ar—C(O)OH,
—CH$_2$—S(O)$_q$—(CH$_2$)$_m$—Ar—C(O)OR'
—CH$_2$—S(O)$_q$—(CH$_2$)$_m$—Ar—C(O)NH$_2$,
—CH$_2$—S(O)$_q$—(CH$_2$)$_m$—Ar—C(O)NHR',
—CH$_2$—S(O)$_q$—(CH$_2$)$_m$—Ar—C(O)NR'R",
—S(O)$_q$—CH$_3$,
—S(O)$_q$—(CH$_2$)$_m$—C(O)—OH,
—S(O)$_q$—(CH$_2$)$_m$—C(O)—OR',
—S(O)$_q$—(CH$_2$)$_m$—C(O)—NH$_2$,
—S(O)$_q$—(CH$_2$)$_m$—C(O)—NHR',
—S(O)$_q$—(CH$_2$)$_m$—C(O)—NR'R",

—S(O)$_q$—(CH$_2$)$_m$

—S(O)$_q$—(CH$_2$)$_m$—Ar—C(O)OH,
—S(O)$_q$—(CH$_2$)$_m$—Ar—C(O)OR',
—S(O)$_q$—(CH$_2$)$_m$—Ar—C(O)NH$_2$,
—S(O)$_q$—(CH$_2$)$_m$—Ar—C(O)NHR',
—S(O)$_q$—(CH$_2$)$_m$—Ar—C(O)NR'R", and —S(O)$_q$—(CH$_2$)$_m$—Ar—CHN$_4$ wherein m is 1, 2, 3, 4, 5 or 6; q is 0, 1 or 2 and Ar is a divalent aryl group of 6 to 14 carbon atoms; and (d) n is 1, 2 or 3; or pharmaceutically acceptable salts thereof.

Peptidyl arginine aldehydes have been reported to exist in equilibrium structures in aqueous solutions. Bajusz, S., et al., J. Med. Chem., 33: 1729 (1990). These structures, as shown below, include the arginine aldehyde, A, aldehyde hydrate, B, and two amino cyclol forms, C and D. The R group would represent the remainder of a given compound embodied in the present invention. The peptide aldehydes of the present invention include within their definition all the equilibrium forms.

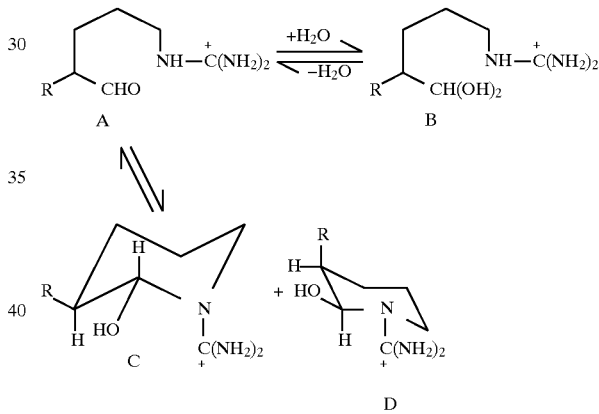

In another aspect, the present invention is directed to pharmaceutical compositions comprising a therapeutically effective amount of a compound of the present invention and a pharmaceutically acceptable carrier.

In yet another aspect, the present invention is directed to methods of using the compounds and pharmaceutical compositions of the present invention for the prevention of thrombosis in a mammal suspected of having a condition characterized by abnormal thrombosis, comprising administering to said mammal a therapeutically effective amount of a compound the present invention or pharmaceutical composition comprising such a compound.

Definitions

In accordance with the present invention and as used herein, the following terms are defined to have following meanings, unless explicitly stated otherwise.

The term "alkyl" refers to saturated aliphatic groups including straight-chain, branched-chain and cyclic groups.

The term "alkoxy" refers to a group having the formula, R—O—, wherein R is an alkyl group.

The term "alkenyl" refers to unsaturated aliphatic groups which contain at least one carbon-carbon double bond and includes straight-chain, branched-chain and cyclic groups.

The term "alkenyloxy" refers to a group having the formula, R—O—, wherein R is an alkenyl group.

The term "aryl" refers to aromatic groups which have at least one ring having a conjugated pi electron system and includes carbocyclic aryl, heterocyclic aryl and biaryl groups, all of which may be optionally substituted.

The term "aryloxy" refers to a group having the formula, R—O—, wherein R is an aryl group.

The term "aralkyl" refers to an alkyl group substituted with an aryl group. Suitable aralkyl groups include benzyl, picolyl, and the like, all of which may be optionally substituted.

The term "aralkoxy" refers to a group having the formula, R—O—, wherein R is an aralkyl group.

The term "aralkenyl refers to an alkenyl group substituted with an aryl group. Suitable aralkenyl groups include styrenyl and the like, all of which may be optionally substituted.

The term "aralkenyloxy" refers to a group having the formula, R—O—, wherein R is an aralkenyl group.

The term "alkylene" refers to a divalent straight chain or branched chain saturated aliphatic radical.

The term "alkylenecarboxy" refers to the group -alk-COOH where alk is alklene.

The term "alkylene aryl" refers to the group -alk-Ar where alk is alkylene and Ar is a divalent aryl group.

The term "carboxamide" refers to the group —C(=O)—NH$_2$.

The term "alkylenecarboxamide" refers to the group -alk-C(=O)—NH$_2$ where alk is alkylene.

The term "alkylenehydroxy" refers to the group -alk-OH herein alk is alkylene.

The term "amino acid" refers to both natural and unnatural amino acids. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid.

The term "amino acid residue" refers to —NH—CH(R)—CO—, wherein R is the side chain group distinguishing each amino acid. For cyclic amino acids, the residue is

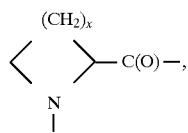

wherein x is 1, 2 or 3 representing the azetidinecarboxylic acid, proline or pipecolic acid residues, respectively.

The term "methylene" refers to —CH$_2$—.

The term "perfluoroalkyl refers to an alkyl group wherein each hydrogen is replaced by a fluoro. Suitable perfluoroalkyl groups include perfluoromethyl (having the structure of CF$_3$—) and perfluroethyl (having the structure of CF$_3$—CF$_2$—) and the like.

The term "perfluoroaryl refers to an aryl group wherein each hydrogen is replaced by a fluoro. Suitable perfluoroaryl groups include perfluorophenyl (having the formula of

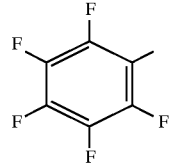

and 2-perfluoronaphthyl (having the formula of

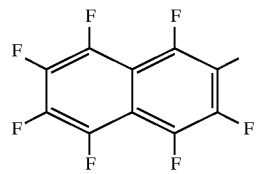

and the like.

In addition, the following abbreviations stand for the following:

"AIBN" refers to

"N-Boc-N$^g$-nitro-L-arginine" refers to the compound which has the formula:

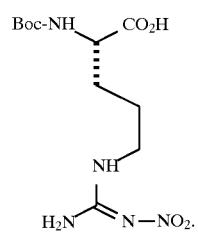

"Arg-al" refers to L-argininal which has the formula:

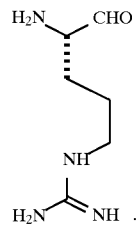

"Arg-ol" refers to L-argininol which has the formula:

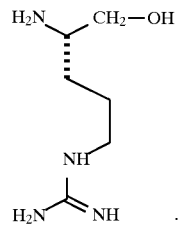

"Azt" refers to L-2-azetidinecarboxylic acid.
"Bzl" refers to benzyl.
"BzlSO$_2$" refers to benzylsulfonyl.
"Boc" refers to t-butoxycarbonyl.

"BOP" refers to benzotriazol-1-yloxy-tris-(dimethylamino)-phosphonium-hexafluorophosphate.

"Brine" means an aqueous saturated solution of sodium chloride.

"BuSO$_2$" refers to 1-butanesulfonyl.

"d-camphor-SO$_2$" refers to d-10-camphorsulfonyl which has the formula:

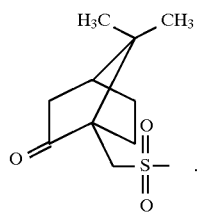

"l-camphor-SO$_2$" refers to l-10-camphorsulfonyl which has the formula:

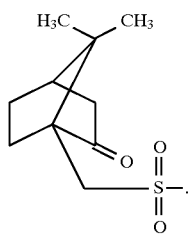

"CDI" refers to carbonyldiimidazole.

"CHN$_4$" refers to tetrazolyl.

"ChxCH$_2$SO$_2$" refers to cyclohexylmethanesulfonyl.

"ChxNHSO$_2$" refers to N-cyclohexylaminosulfonyl.

"2-CMPhSO$_2$" refers to 2-carbomethoxy-1-phenylsulfonyl.

"Cys[S—CH$_3$]" refers to S-methyl-L-cysteine which has the formula:

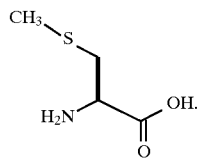

"Cys[S(O)—CH$_3$]" refers to S-methyl-L-cysteine sulfoxide which has the formula:

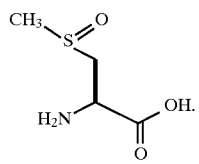

"Cys[S(O$_2$)—CH$_3$]" refers to S-methyl-L-cysteine sulfone which has the formula:

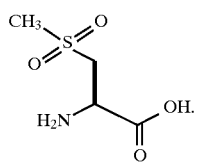

"Cys[S—CH$_2$CO$_2$H]" refers to S-(carboxymethyl)-L-cysteine which has the formula:

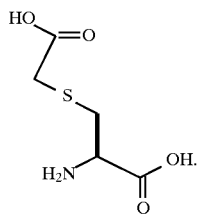

"Cys[S(O)—CH$_2$CO$_2$H]" refers to S-(carboxymethyl)-L-cysteine sulfoxide which has the formula:

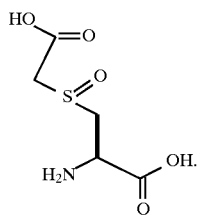

"Cys[S(O$_2$)—CH$_2$CO$_2$H]" refers to S-(carboxymethyl)-L-cysteine sulfone which has the formula:

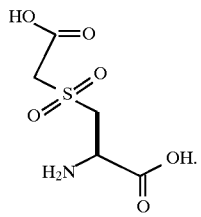

"Cys[S—CH$_2$CO$_2$CH$_3$]" refers to S-(carbomethoxymethyl)-L-cysteine which has the formula:

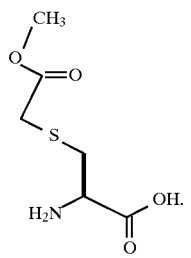

"Cys[S(O)—CH$_2$CO$_2$CH$_3$]" refers to S-(carbomethoxymethyl)-L-cysteine sulfoxide which has the formula:

"Cys[S(O₂)—CH₂CO₂CH₃]" refers to S-(carbomethoxymethyl)-L-cysteine sulfone which has the formula:

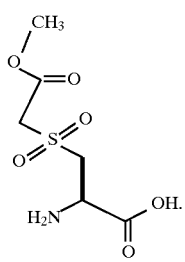

"Cys[(S—CH₂Tzl]" refers to S-(tetrazol-5-ylmethyl)-L-cysteine which has the formula:

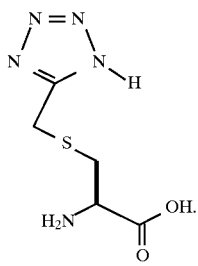

"Cys[S(O)—CH₂Tzl]" refers to S-(tetrazol-5-yl)-L-cysteine methyl sulfoxide which has the formula:

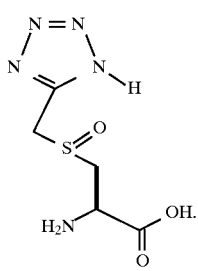

"CYs[S(O₂)—CH₂Tzl]" refers to S-(tetrazol-5-yl)-L-cysteine methyl sulfone which has the formula:

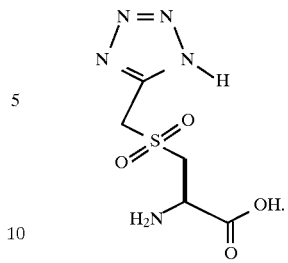

"DCC" refers to 1,3-dicyclohexylcarbodiimide.
"DCM" refers to dichloromethane.
"DIEA" refers to diisopropylethylamine.
"DMF" refers to N,N-dimethylformamide.
"EDC" refers to ethyl-3-(3-dimethylamino)propylcarbodiimide hydrochloride salt.
"HBTU" refers to 2-(1H benzotriazol-1-yl)-1,1,3,3-tetramethyluronium hexafluorophosphate.
"HOBt" refers to 1-hydroxybenzotriazole monohydrate.
"MeOH" refers to methanol.
"Met[S(O)]" refers to L-methionine sulfoxide which has the formula:

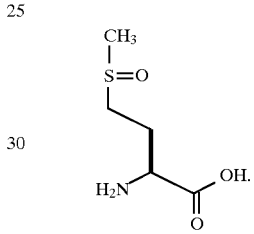

"Met[S(O₂)]" refers to L-methionine sulfone which has the formula:

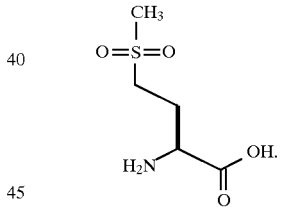

"MgSO₄" refers to anhydrous magnesium sulfate.
"MeOH" refers to methanol.
"1-NpSO₂" refers to 1-naphthalenesulfonyl.
"2-NPSO₂" refers to 2-naphthalenesulfonyl.
"NMP" refers to N-methylpiperidine.
"NMM" refers to 4-methylmorpholine.
"Ph" refers to phenyl.
"Pip" refers to L-pipecolic acid.
"Pro" refers to L-proline.
"2-PrPen" refers to 2-propylpentanoyl.
"TBTU" refers to 2-(1H-benzotriazol-1-yl)-1,1,3,3-tetramethyluronium tetrafluoroborate.
"TEA" refers to triethylamine.
"TFA" refers to trifluoroacetic acid.
"THF" refers to tetrahydrofuran.

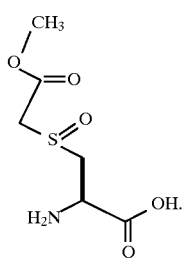

the compounds of the present invention. In this figure, Bzl refers to benzyl; t-Bu refers to t-butyl; and Boc refers to t-butoxycarbonyl.

Figure 2:
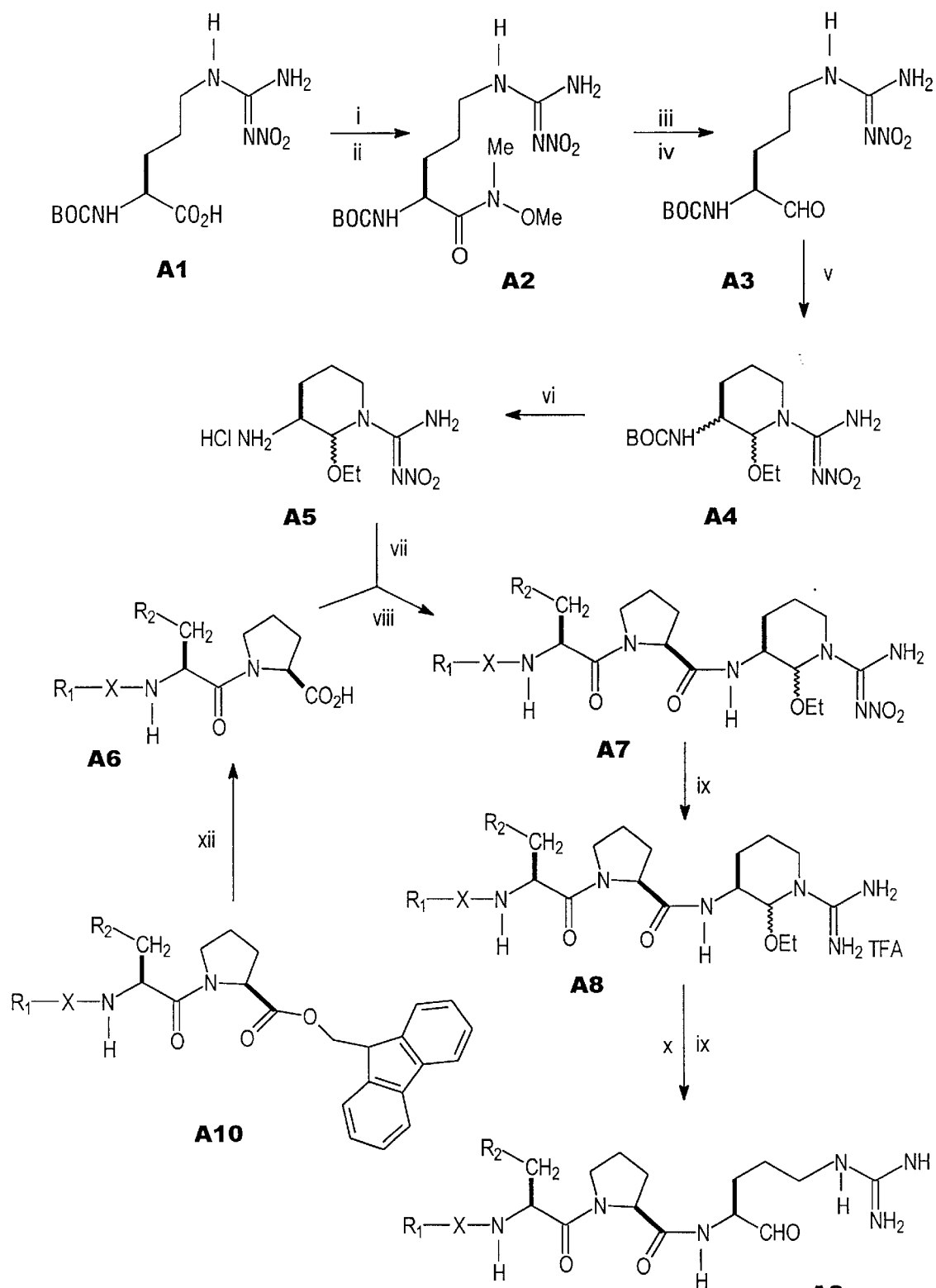

FIG. 2 depicts a reaction scheme describing a preferred solution phase synthesis route for preparing the peptide aldehydes of the present invention. In this figure, Boc refers to t-butoxycarboxyl, Et refers to ethyl, Me refers to methyl and $R_1$, $R_2$ and X are as defined in connection with formula (I). In this figure, (i) to (xii) denote the following reaction conditions, reagents and/or solvents: (i) N-methylpiperidine, isobutylchloroformate, 5° C.; (ii) N-methyl-O-methylhydroxylamine hydrochloride, N-methylpiperidine, 5° C.; (iii) lithium aluminum hydride, tetrahydrofuran, −60° C.; (iv) potassium bisulfate, −30° C.; (v) hydrochloric acid, ethanol; (vi) ethanol, hydrogen chloride(g); (vii) dimethylformamide/acetonitrile, HBTU, HOBT, 0° C.; (viii) 4-methyl-morpholine; (ix) methanol/water/acetic acid, hydrogenation catalyst (such as Pd/C); (x) acetonitrile/water, hydrochloric acid, 0° C.; (xi) aqueous sodium acetate; and (xii) tetrahydrofuran, piperidine.

Figure 3:
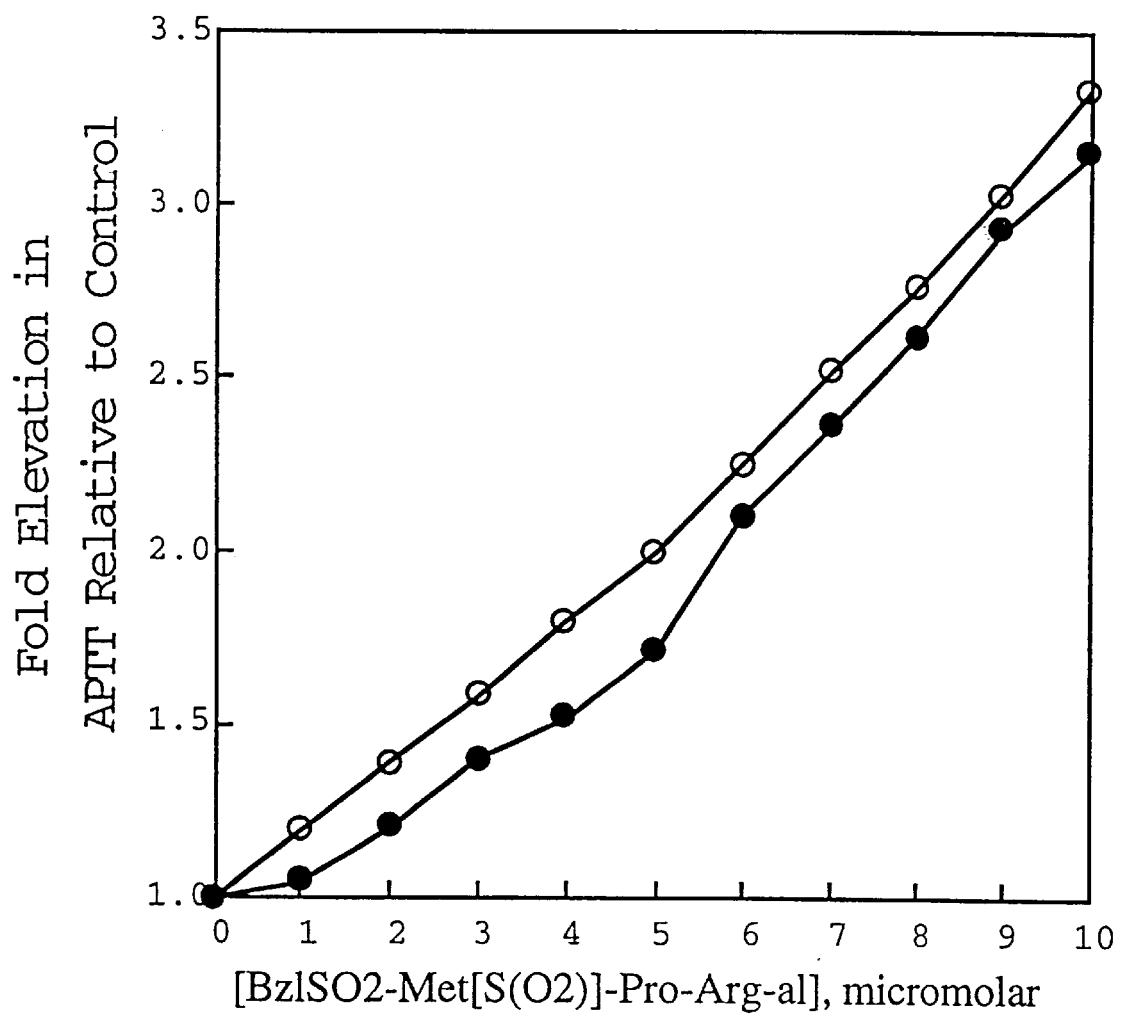

FIG. 3 depicts the anticoagulant effect of the compound of Example 27, BzlSO$_2$-Met[S(O$_2$)]-Pro-Arg-al, measured in citrated rat (●) and human (○) plasma using the activated partial thromboplastin time (APTT) assay. The elevation in APTT due to increasing concentration of compound is presented relative to the control clotting time for rat (19.75 sec) and human (28.3 sec) plasma which is set to a value of 1.0.

DETAILED DESCRIPTION OF THE INVENTION

1. Preferred Compounds

In one aspect, the present invention is directed to certain compounds which are the peptide aldehydes as depicted in formula (IA) below:

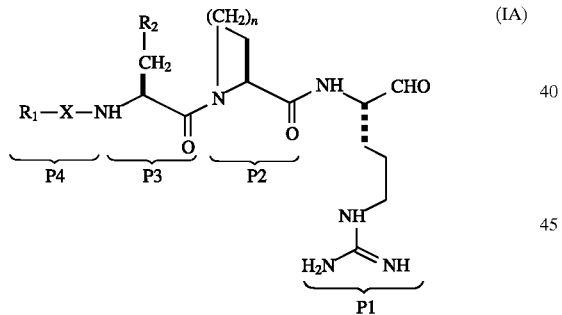

wherein
(a) X is selected from the group consisting of —O—C(O)—, —NH—C(O)—, —C(O)—, —S(O$_2$)—, —O—S(O$_2$)—, —NH—S(O$_2$)— and —N(R')—S(O$_2$)—, wherein R' is alkyl of 1 to about 4 carbon atoms, aryl of about 6 to about 14 carbon atoms, or aralkyl of about 6 to about 15 carbon atoms;
(b) $R_1$ is selected from the group consisting of:
 (1) alkyl of about 3 to about 10 carbon atoms,
 (2) alkyl of 1 to about 3 carbon atoms substituted with cyclic alkyl of about 5 to about 8 carbon atoms,
 (3) alkenyl of about 3 to about 6 carbon atoms,
 (4) alkenyl of about 3 to about 6 carbon atoms which is substituted with cyclic alkyl of about 5 to about 8 carbon atoms,
 (5) aryl of about 6 to about 14 carbon atoms,
 (6) aryl of about 6 to about 14 carbon atoms which is substituted with $Y_1$,
 (7) aryl of about 6 to about 14 carbon atoms which is substituted with $Y_1$ and $Y_2$, or $Y_1$, $Y_2$ and $Y_3$.
 (8) aralkyl of about 6 to about 15 carbon atoms,
 (9) aralkyl of about 6 to about 15 carbon atoms which is substituted in the aryl ring with $Y_1$,
 (10) aralkyl of about 6 to about 15 carbon atoms which is substituted in the aryl ring with $Y_1$ and $Y_2$, or $Y_1$, $Y_2$ and $Y_3$.
 (11) aralkenyl of about 8 to about 15 carbon atoms,
 (12) aralkenyl of about 8 to about 15 carbon atoms which is substituted in the aryl ring with $Y_1$,
 (13) aralkenyl of about 8 to about 15 carbon atoms which is substituted in the aryl ring with $Y_1$ and $Y_2$, or $Y_1$, $Y_2$ and $Y_3$.
 (14) perfluoroalkyl of 1 to about 12 carbon atoms,
 (15) perfluoroaryl of about 6 to about 14 carbon atoms,
 (16) trimethylsilylalkyl of about 4 to about 8 carbon atoms,

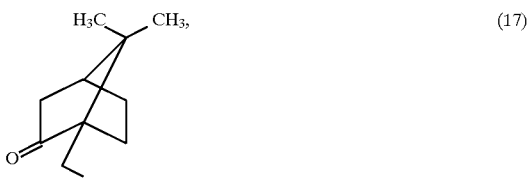

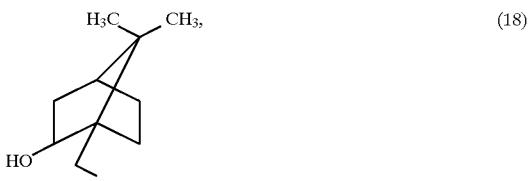

wherein W is oxygen, methylene, —C(O)—, —CH(OH)—, —CH(OA$_1$)—, —CH(C(O)—OH)—, —CH(C(O)—OR')—, —CH(C(O)—NHR')—, —CH(C(O)—NR'R")—,

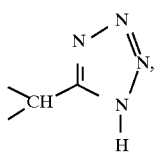

—NH— or —N(R')—, and X is not —O—C(O)—, —NH—C(O)—, —O—S(O$_2$)—, —NH—S(O$_2$)— or —N(R')—S(O$_2$)—, (22)

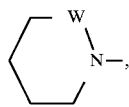

where X is not —O—C(O)—, —NH—C(O)—, —O—S(O$_2$)—, —NH—S(O$_2$)— or —N(R')—S(O$_2$)—, (23)

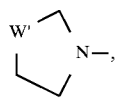

wherein W' is oxygen, sulfur, —S(O)—, —S(O$_2$)—, methylene, —C(O)—, —CH(OH)—, —CH(OA$_1$)—, —CH(C(O)—OH)—, —CH(C(O)—OR')—, —CH(C(O)—NHR')—, —CH(C(O)—NR'R")—,

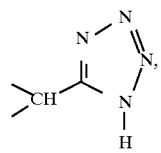

—NH— or —N(R')—, and X is not —O—C(O)—, —NH—C(O)—, —O—S(O$_2$)—, —NH—S(O$_2$)— or —N(R')—S(O$_2$)—, (24)

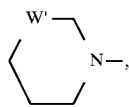

where X is not —O—C(O)—, —NH—C(O)—, —O—S(O$_2$)—, —NH—S(O$_2$)— or —N(R')—S(O$_2$)—, (25)

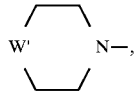

where X is not —O—C(O)—, —NH—C(O)—, —O—S(O$_2$)—, —NH—S(O$_2$)— or —N(R')—S(O$_2$)—, (26)

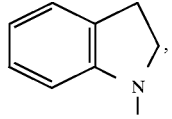

where X is not —O—C(O)—, —NH—C(O)—, —O—S(O$_2$)—, —NH—S(O$_2$)— or —N(R')—S(O$_2$)—,

(27) a substituted group of the formula

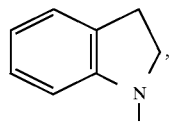

wherein the aryl ring is substituted with Y$_1$, and X is not —O—C(O)—, —NH—C(O)—, —O—S(O$_2$)—, —NH—S(O$_2$)— or —N(R')—S(O$_2$)—, and

(28) a substituted group of the formula

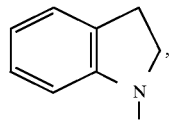

wherein the aryl ring is substituted with Y$_1$ and Y$_2$, and X is not —O—C(O)—, —NH—C(O)—, —O—S(O$_2$)—, —NH—S(O$_2$)— or —N(R')—S(O$_2$)—, wherein Y$_1$, Y$_2$ and Y$_3$ are independently selected from the group consisting of bromo, chloro, fluoro, —Z$_1$, —OH, —OZ$_1$, —NH$_2$, —NHZ$_1$, —NZ$_1$Z$_2$, —NH—C(O)—Z$_1$, —N(Z$_1$)—C(O)—Z$_2$, —NH—C(O)—OZ$_1$, —N(Z$_1$)—C(O)—OZ$_2$, —NH—C(O)—NH$_2$, —NH—C(O)—NHZ$_1$, —NH—C(O)—NZ$_1$Z$_2$, —N(Z$_1$)—C(O)—NHZ$_2$, —N(Z$_1$)—C(O)—NZ$_2$Z$_3$, —C(O)—OH, —C(O)—OZ$_1$, —C(O)—NHZ$_1$, —C(O)—NZ$_1$Z$_2$, —SH, —SZ$_1$, —S(O)—Z$_1$, —S(O$_2$)—Z$_1$, —S(O$_2$)—OH, —S(O$_2$)—OZ$_1$, —S(O$_2$)—NH$_2$, —S(O$_2$)—NHZ$_1$, —S(O$_2$)—NZ$_1$Z$_2$ and

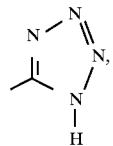

wherein Z$_1$, Z$_2$ and Z$_3$ are independently selected from the group consisting of trifluoromethyl, pentafluoroethyl, alkyl of 1 to about 12 carbon atoms, aryl of about 6 to about 14 carbon atoms, and aralkyl of about 6 to about 15 carbon atoms, R" is alkyl of 1 to about 4 carbon atoms, aryl of about 6 to about 14 carbon atoms, or aralkyl of about 6 to about 15 carbon atoms, A$_1$ is aryl of about 6 to about 14 carbon atoms, aryl of about 6 to about 14 carbon atoms which is substituted with Y$_1$, aralkyl of about 6 to about 15 carbon atoms, or aralkyl of about 6 to about 15 carbon atoms which is substituted with Y$_1$;

(c) R$_2$ is selected from the group consisting of
—CH$_2$—S(O)$_q$—CH$_3$,
—CH$_2$—S(O)$_q$—(CH$_2$)$_m$—C(O)—OH,
—CH$_2$—S(O)$_q$—(CH$_2$)$_m$—C(O)—OR',
—CH$_2$—S(O)$_q$—(CH$_2$)$_m$—C(O)—NH$_2$,
—CH$_2$—S(O)$_q$—(CH$_2$)$_m$—C(O)—NHR', —CH$_2$—S(O)$_q$—(CH$_2$)$_m$—C(O)—NR'R",

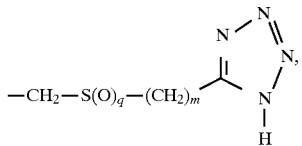

—CH$_2$—S(O)$_q$—(CH$_2$)$_m$—Ar—C(O)OH,
—CH$_2$—S(O)$_q$—(CH$_2$)$_m$—Ar—C(O)OR',
—CH$_2$—S(O)$_q$—(CH$_2$)$_m$—Ar—C(O)NH$_2$,
—CH$_2$—S(O)$_q$—(CH$_2$)$_m$—Ar—C(O)NHR',
—CH$_2$—S(O)$_q$—(CH$_2$)$_m$—Ar—CN$_4$H,
—S(O)$_q$—CH$_3$,
—S(O)$_q$—(CH$_2$)$_m$—C(O)—OH,
—S(O)$_q$—(CH$_2$)$_m$—C(O)—OR',
—S(O)$_q$—(CH$_2$)$_m$—C(O)—NH$_2$,
—S(O)$_q$—(CH$_2$)$_m$—C(O)—NHR',
—S(O)$_q$—(CH$_2$)$_m$—C(O)—NR'R",

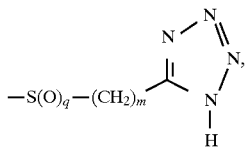

—S(O)$_q$—(CH$_2$)$_m$—Ar—C(O)OH,
—S(O)$_q$—(CH$_2$)$_m$—Ar—C(O)OR',
—S(O)$_q$—(CH$_2$)$_m$—Ar—C(O)NH$_2$,
—S(O)$_q$—(CH$_2$)$_m$—Ar—C(O)NHR',
—S(O)$_q$—(CH$_2$)$_m$—Ar—C(O)NR'R", and
S(O)$_q$—(CH$_2$)$_m$—Ar—CN$_4$H, wherein m is 1, 2, 3, 4, 5 or 6; q is 0, 1 or 2 and Ar is a divalent aryl group of 6 to 14 carbon atoms; and (d) n is 1, 2 or 3; or pharmaceutically acceptable salts thereof.

Compounds of formula (IA) include those wherein P2 is L-2-azetidinecarboxylic acid, L-proline or L-pipecolic acid. Preferred compounds include those wherein P2 is L-2-azetidinecarboxylic acid or L-proline. Especially preferred compounds include those wherein P2 is L-proline.

The compounds of formula (IA) include those wherein P3 is: (1) L-cysteine which is substituted on its sulfur atom with a methyl, straight-chain alkylene of 1 to about 6 carbon atoms or alkylene aryl, wherein said straight-chain alkylene or alkylenearyl is substituted with —C(O)—OH, —C(O)—OR', —C(O)—NH$_2$, —C(O)—NHR', —C(O)—NR'R", or tetrazol-5-yl, wherein R' and R" are independently selected from the group consisting of alkyl of 1 to about 4 carbon atoms, aryl of about 6 to about 14 carbon atoms, or aralkyl of about 6 to about 15 carbon atoms; (2) L-cysteine sulfoxide which is substituted on its sulfur atom with a methyl, straight-chain alkylene of 1 to about 6 carbon atoms, or alkylene aryl wherein said straight-chain alkylene or alkylene aryl is substituted with —C(O)—OH, —C(O)—OR', —C(O)—NH$_2$, —C(O)—NHR', —C(O)—NR'R", or tetrazol-5-yl; (3) L-cysteine sulfone which is substituted on its sulfur atom with a methyl or straight-chain alkylene of 1 to about 6 carbon atoms, or alkylene aryl wherein said straight-chain alkylene or alkylene aryl is substituted with —C(O)—OH, —C(O)—OR', —C(O)—NH$_2$, —C(O)—NHR', —C(O)—NR'R", or tetrazol-5-yl; (4) L-methionine; (5) L-methionine which is substituted on its S-methyl group with a straight-chain alkylene of 1 to about 6 carbon atoms, alkylene aryl or a divalent aryl group wherein said straight-chain alkylene, alkylene aryl, or divalent aryl group is substituted with —C(O)—OH, —C(O)—OR', —C(O)—NH$_2$, —C(O)—NHR', —C(O)—NR'R", or tetrazol-5-yl; (6) L-methionine sulfoxide; (7) L-methionine sulfoxide which is substituted on its S-methyl group with a straight-chain alkylene of 1 to about 6 carbon atoms, alkylene aryl or divalent aryl group, wherein said straight-chain alkylene, alkylene aryl or divalent aryl group is substituted with —C(O)—OH, —C(O)—O—R', —C(O)—NH$_2$, —C(O)—NHR', —C(O)—NR'R", or tetrazol-5-yl; (8) L-methionine sulfone; or (9) L-methionine sulfone which is substituted on its S-methyl group with a straight-chain alkylene of 1 to about 6 carbon atoms, alkylene aryl or divalent aryl group wherein said straight-chain alkylene, alkylene aryl or divalent aryl group is substituted with —C(O)—OH, —C(O)—O—R', —C(O)—NH$_2$, —C(O)—NHR', —C(O)—NR'R", or tetrazol-5-yl. Suitable alkylene aryl groups those having 1 to 6 carbons in the alkylene group and from about 6 to 14 carbons in the divalent aryl. Suitable divalent aryl groups have from 6 to 14 carbon atoms.

Preferred compounds include those wherein the amino acid residue at P3 is: (1) L-cysteine which is substituted on its sulfur atom with a straight-chain alkylene of 1 to 3 carbon atoms, wherein said straight-chain alkylene is substituted with —C(O)—OH, —C(O)—O—CH$_3$, —C(O)—O—CH$_2$—CH$_3$, —C(O)—O—CH$_2$—CH$_2$—CH$_3$, or tetrazol-5-yl; (2) L-cysteine sulfoxide which is substituted on its sulfur atom with a methyl or straight-chain alkylene of 1 to 3 carbon atoms, wherein said straight-chain alkylene is substituted with —C(O)—OH, —C(O)—O—CH$_3$, —C(O)—O—CH$_2$—CH$_3$, —C(O)—O—CH$_2$—CH$_2$—CH$_3$, or tetrazol-5-yl; (3) L-cysteine sulfone which is substituted on its sulfur atom with a methyl or straight-chain alkylene of 1 to 3 carbon atoms, wherein said straight-chain alkylene is substituted with —C(O)—OH, —C(O)—O—CH$_3$, —C(O)—O—CH$_2$—CH$_3$, —C(O)—O—CH$_2$—CH$_2$—CH$_3$, or tetrazol-5-yl; (4) L-methionine; (5) L-methionine which is substituted on its S-methyl group with a straight-chain alkylene of 1 to 3 carbon atoms, wherein said straight-chain alkylene is substituted with —C(O)—OH, —C(O)—O—CH$_3$, —C(O)—O—CH$_2$—CH$_3$, —C(O)—O—CH$_2$—CH$_2$—CH$_3$, or tetrazol-5-yl; (6) L-methionine sulfoxide; (7) L-methionine sulfoxide which is substituted on its S-methyl group with a straight-chain alkylene of 1 to 3 carbon atoms, wherein said straight-chain alkylene is substituted with —C(O)—OH, —C(O)—O—CH$_3$, —C(O)—O—CH$_2$—CH$_3$, —C(O)—O—CH$_2$—CH$_2$—CH$_3$, or tetrazol-5-yl; (8) L-methionine sulfone; or (9) L-methionine sulfone which is substituted on its S-methyl group with a straight-chain alkylene of 1 to 3 carbon atoms, wherein said straight-chain alkylene is substituted with —C(O)—OH, —C(O)—O—CH$_3$, —C(O)—O—CH$_2$—CH$_3$, —C(O)—O—CH$_2$—CH$_2$—CH$_3$, or tetrazol-5-yl.

Also preferred are compounds wherein the amino acid residue at P3 has an alkylene aryl substituent attached to the sulfur atom, and substituted with —C(O)—OH, —C(O)OR', —C(O)NH$_2$, —C(O)NHR', or —C(O)NR'N". Especially preferred substituted alkylene aryl include those where the alkylene moiety is —CH$_2$— or —CH$_2$CH$_2$— and Ar is a divalent phenyl group.

Especially preferred compounds include those wherein P3 is L-methionine sulfone, S-methyl-L-cysteine sulfone, S-(carboxymethyl)-L-cysteine sulfone, S(carbomethoxymethyl)-L-cysteine sulfone, S-(carboethoxymethyl)-L-cysteine sulfone, or S-(carbopropyloxymethyl)-L-cysteine sulfone.

Compounds of formula (IA) include those wherein P4 is R$_1$—C(O)—, R$_1$—S(O$_2$)—, R$_1$—O—S(O$_2$)—, R$_1$—NH—S(O$_2$)— or R$_1$—N(R')—S(O$_2$)—.

Preferred compounds include those wherein $R_1$ is alkyl of about 3 to about 10 carbon atoms; alkyl of 1 to about 3 carbon atoms substituted with cyclic alkyl of about 5 to about 8 carbon atoms; aryl of about 6 to about 14 carbon atoms; aryl of about 6 to about 14 carbon atoms which is substituted with $Y_1$; aryl of about 6 to about 14 carbon atoms which is substituted with $Y_1$ and $Y_2$; aralkyl of about 6 to about 15 carbon atoms; aralkyl of about 6 to about 15 carbon atoms which is substituted in the aryl ring with $Y_1$; aralkyl of about 6 to about 15 carbon atoms which is substituted in the aryl ring with $Y_1$ and $Y_2$;

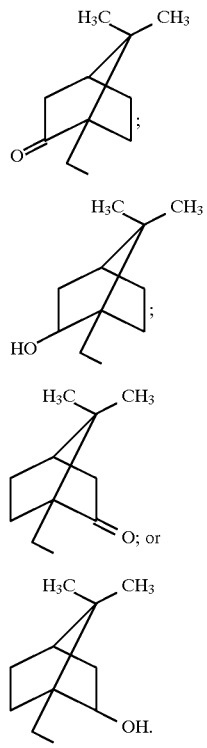

Suitable alkyls for $R_1$ include 1-propyl, 2-methyl-1-propyl, 2,2-dimethyl-1-propyl, 2-propyl, 2-methyl-2-propyl, 1-butyl, 2-butyl, 3-butyl, 3-methy-1-butyl, 1-pentyl, cyclopentyl, 1-hexyl, cyclopentylmethyl, cyclohexyl, cyclohexylmethyl, 1-heptyl, 4-heptyl, octyl, nonanyl, dodecanyl, adamantyl or adamantylmethyl. Suitable cyclic alkyls include cyclopentyl, cyclopentylmethyl, cyclohexyl, cyclohexylmethyl, adamantyl and adamantylmethyl. Suitable aryl groups for $R_1$ include phenyl, 2-carboxyphenyl, 2-carbomethoxyphenyl, 2-indanyl, 2-indenyl, 1-naphthyl, 2-naphthyl, 2-thienyl, 2-pyrrolyl or 2-furyl. Suitable aralkyl groups include benzyl, diphenylmethyl, biphenylmethyl, naphthylmethyl, alpha-phenylmethylphenyl and 2-phenylethylene.

Where P3 is L-methionine sulfone, preferred compounds of formula (IA) include those wherein P4 is $R_1$—S($O_2$)—, $R_1$—O—S($O_2$)—, $R_1$—NH—S($O_2$)— or $R_1$—C(O)—. Especially preferred compounds include those wherein P4 is $R_1$—S($O_2$)— or $R_1$—C(O)—.

Where P4 is $R_1$—S($O_2$)—, preferred compounds include those wherein $R_1$ is alkyl of about 3 to about 10 carbon atoms, alkyl of 1 to about 3 carbon atoms substituted with cyclic alkyl of about 5 to about 8 carbon atoms, aryl of about 6 to about 14 carbon atoms, aryl of about 6 to about 14 carbon atoms which is substituted with $Y_1$, aryl of about 6 to about 14 carbon atoms which is substituted with $Y_1$ and $Y_2$, aralkyl of about 6 to about 15 carbon atoms, aralkyl of about 6 to about 15 carbon atoms which is substituted in the aryl ring with $Y_1$, or aralkyl of about 6 to about 15 carbon atoms which is substituted in the aryl ring with $Y_1$ and $Y_2$. Especially preferred compounds include those wherein $R_1$ is aryl of about 6 to about 14 carbon atoms, or aryl of about 6 to about 14 carbon atoms which is substituted with $Y_1$. More especially preferred compounds include those wherein $R_1$ is phenyl, 2-carboxyphenyl, 2-carbomethoxyphenyl, 1-naphthyl or 2-naphthyl.

Where P4 is $R_1$—C(O)—, preferred compounds include those wherein $R_1$ is alkyl of about 3 to about 10 carbon atoms, alkyl of 1 to about 3 carbon atoms substituted with cyclic alkyl of about 5 to about 8 carbon atoms, aralkyl of about 6 to about 15 carbon atoms, aralkyl of about 6 to about 15 carbon atoms which is substituted in the aryl ring with $Y_1$, or aralkyl of about 6 to about 15 carbon atoms which is substituted in the aryl ring with $Y_1$ and $Y_2$. Especially preferred compounds include those wherein $R_1$ is alkyl of about 3 to about 10 carbon atoms. More especially preferred compounds include those wherein $R_1$ is 1-butyl, 1-heptyl or 4-heptyl.

Alternatively, where P3 is S-methyl-L-cysteine sulfone, preferred compounds of formula (IA) include those wherein P4 is $R_1$—S($O_2$)—, $R_1$—NH—S($O_2$)— or $R_1$—C(O)—. Especially preferred compounds include those wherein P4 is $R_1$—S($O_2$)—.

Where P4 is $R_1$—S($O_2$)—, preferred compounds include those wherein $R_1$ is alkyl of about 3 to about 10 carbon atoms, alkyl of 1 to about 3 carbon atoms substituted with cyclic alkyl of about 5 to about 8 carbon atoms, aryl of about 6 to about 14 carbon atoms, aryl of about 6 to about 14 carbon atoms which is substituted with $Y_1$, aryl of about 6 to about 14 carbon atoms which is substituted with $Y_1$ and $Y_2$, aralkyl of about 6 to about 15 carbon atoms, aralkyl of about 6 to about 15 carbon atoms which is substituted in the aryl ring with $Y_1$, or aralkyl of about 6 to about 15 carbon atoms which is substituted in the aryl ring with $Y_1$ and $Y_2$. Especially preferred compounds include those wherein $R_1$ is aryl of about 6 to about 14, or aryl of about 6 to about 14 carbon atoms which is substituted with $Y_1$. More especially preferred compound include those wherein $R_1$ is phenyl, 2-carboxyphenyl, 2-carbomethoxyphenyl, 1-naphthyl or 2-naphthyl.

Alternatively, where P3 is S-(carboxymethyl)-L-cysteine sulfone, S-(carbomethoxymethyl)-L-cysteine sulfone, S-(carboethoxymethyl)-L-cysteine sulfone, or S-(carbopropyloxymethyl)-L-cysteine sulfone, preferred compounds of formula (IA) include those wherein P4 is $R_1$—S($O_2$)—, $R_1$—NH—S($O_2$)— or $R_1$—C(O)—. Especially preferred compounds include those wherein P3 is S-(carboxymethyl)-L-cysteine sulfone or S-(carbomethoxymethyl)-L-cysteine sulfone and P4 is $R_1$—S($O_2$)— or $R_1$—C(O)—.

Where P3 is S-(carboxymethyl)-L-cysteine sulfone or S-(carbomethoxymethyl)-L-cysteine sulfone and P4 is $R_1$—S($O_2$)—, preferred compounds include those wherein $R_1$ is alkyl of about 3 to about 10 carbon atoms, alkyl of 1 to about 3 carbon atoms substituted with cyclic alkyl of about 5 to about 8 carbon atoms, aryl of about 6 to about 14 carbon atoms, aryl of about 6 to about 14 carbon atoms which is substituted with $Y_1$, aryl of about 6 to about 14 carbon atoms which is substituted with $Y_1$ and $Y_2$, aralkyl of about 6 to about 15 carbon atoms, aralkyl of about 6 to about 15 carbon atoms which is substituted in the aryl ring with $Y_1$, or aralkyl of about 6 to about 15 carbon atoms which is substituted in the aryl ring with $Y_1$ and $Y_2$. Especially preferred compounds include those wherein $R_1$ is aryl of about 6 to about 14 carbon atoms, or aryl of about 6 to about 14 carbon atoms which is substituted with $Y_1$. More especially preferred compounds include those wherein P3 is S-(carboxymethyl)-L-cysteine sulfone and $R_1$ is phenyl, 1-naphthyl or 2-naphthyl. More especially preferred compounds also include those wherein P3 is S-(carbomethoxymethyl)-L-cysteine sulfone and $R_1$ is phenyl, 2-carboxyphenyl, 2-carbomethoxyphenyl, 1-naphthyl or 2-naphthyl.

Where P3 is S-(carboxymethyl)-L-cysteine sulfone or S-(carbomethoxymethyl)-L-cysteine sulfone and P4 is $R_1$—C(O)—, preferred compounds include those wherein $R_1$ is alkyl of about 3 to about 10 carbon atoms, alkyl of 1 to about 3 carbon atoms substituted with cyclic alkyl of about 5 to about 8 carbon atoms, aralkyl of about 6 to about 15 carbon atoms, aralkyl of about 6 to about 15 carbon atoms which is substituted in the aryl ring with $Y_1$, or aralkyl of about 6 to about 15 carbon atoms which is substituted in the aryl ring with $Y_1$ and $Y_2$. Especially preferred compounds include those wherein $R_1$ is alkyl of about 3 to about 10 carbon atoms. More especially preferred compounds include those wherein $R_1$ is 1-butyl, 1-heptyl or 4-heptyl.

Certain preferred compounds of the present invention include:

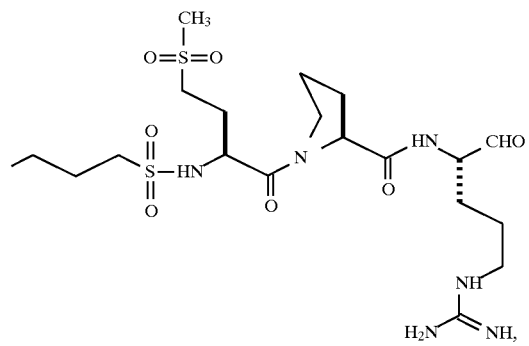

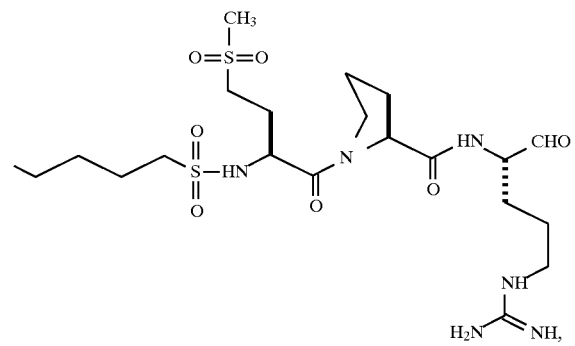

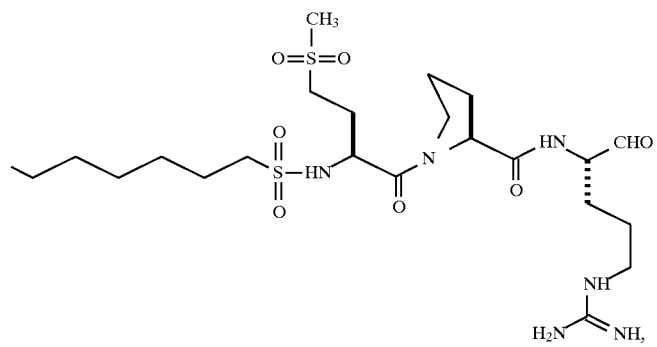

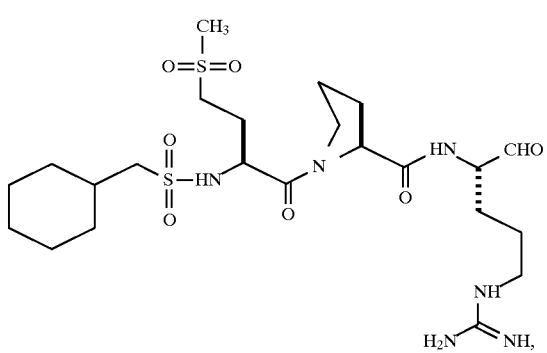

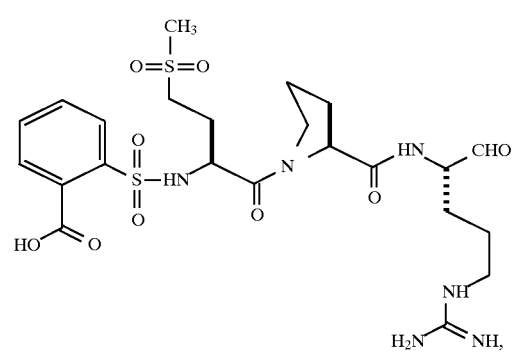

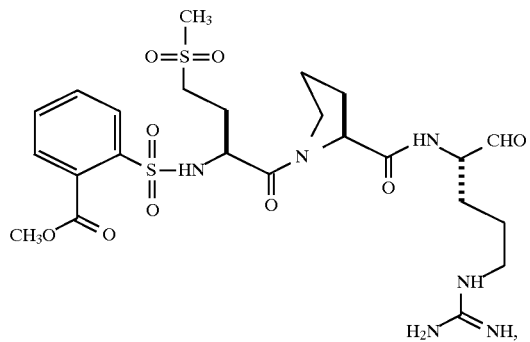

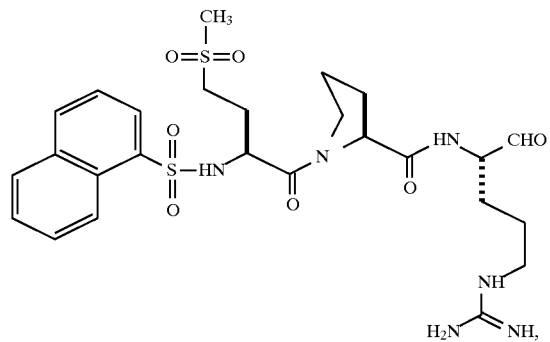

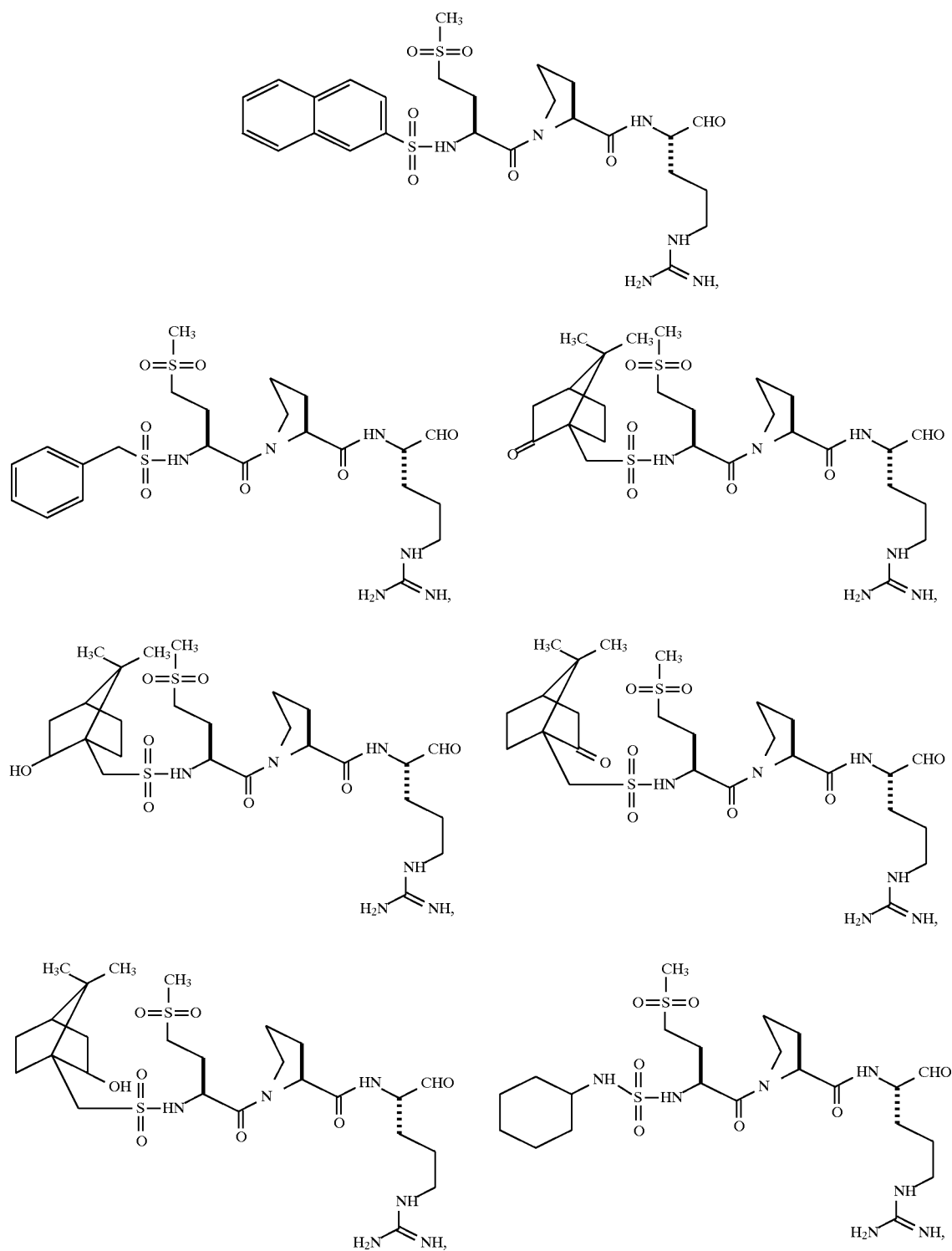

29 30
-continued
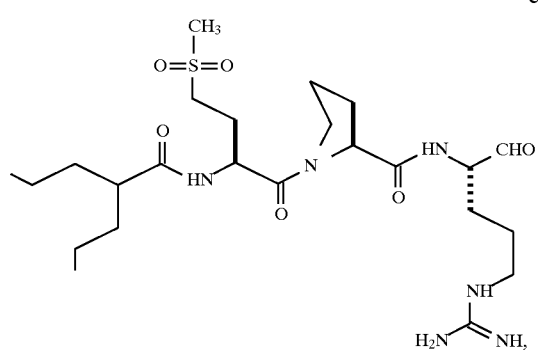 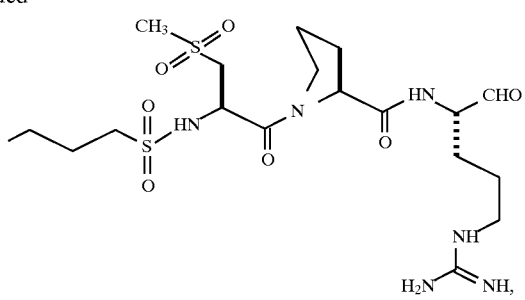
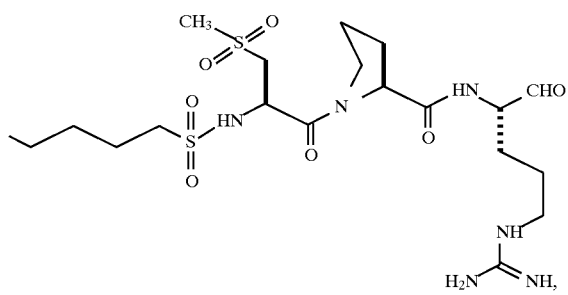
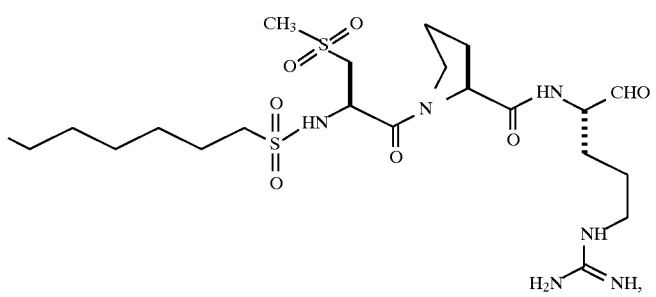
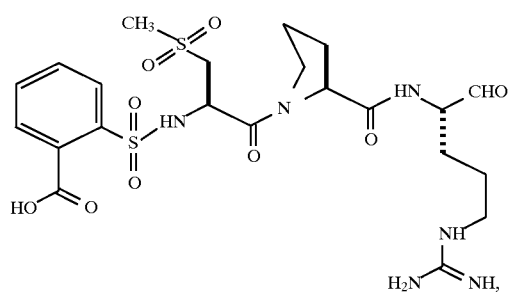 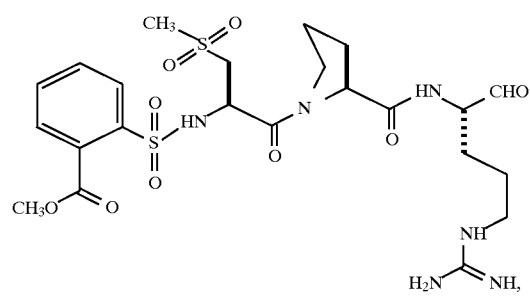
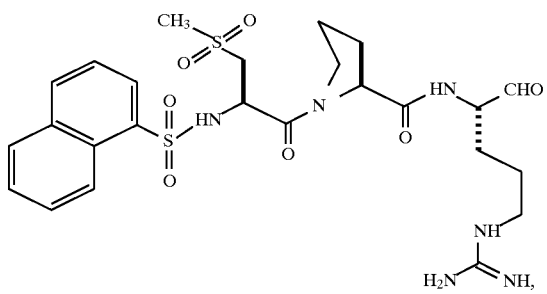 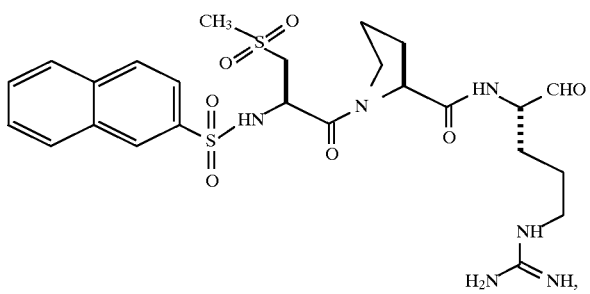

31
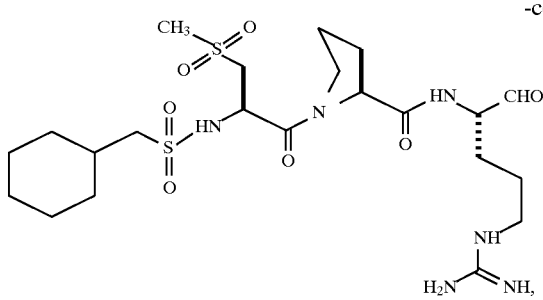
32
-continued
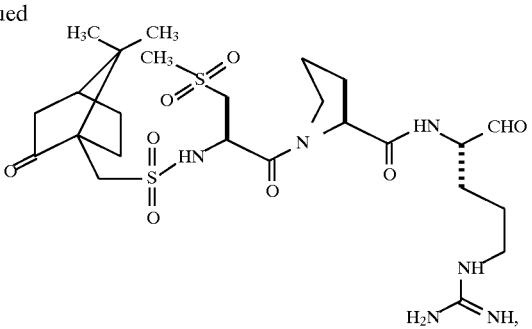
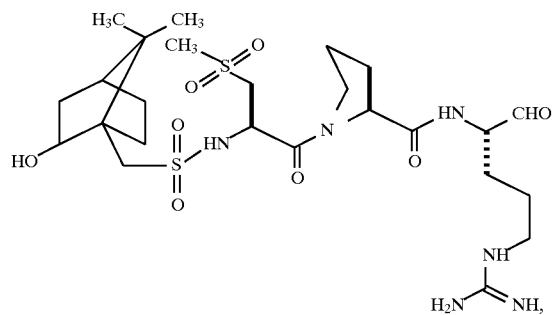
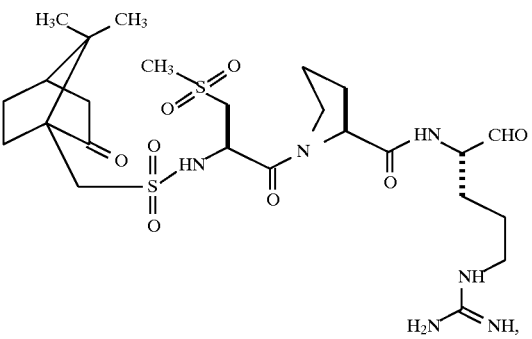
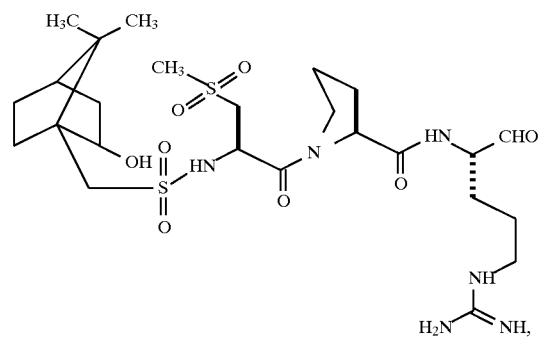
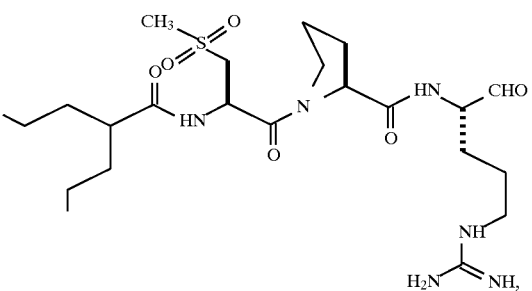
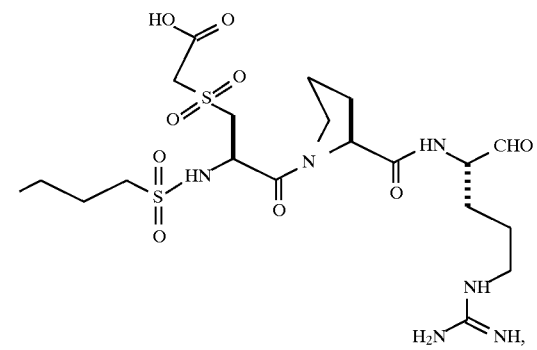
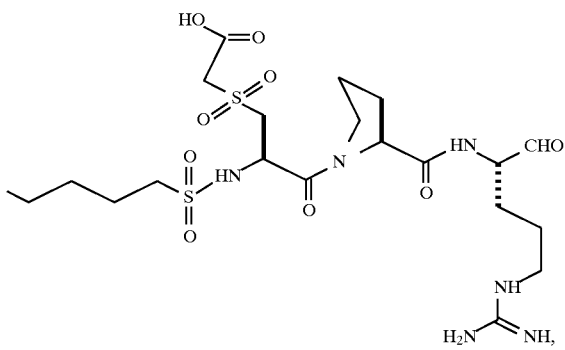
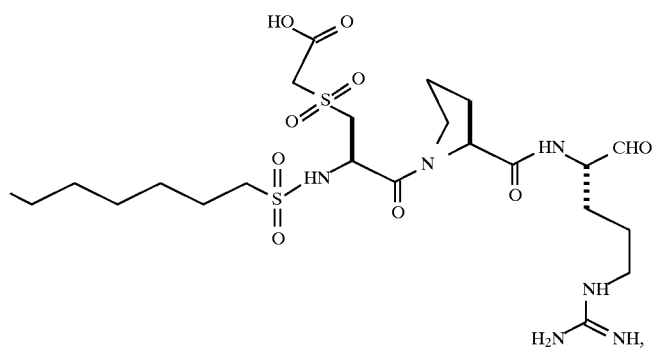

33 34
-continued
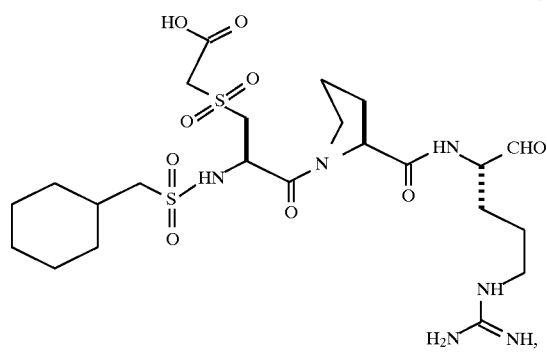
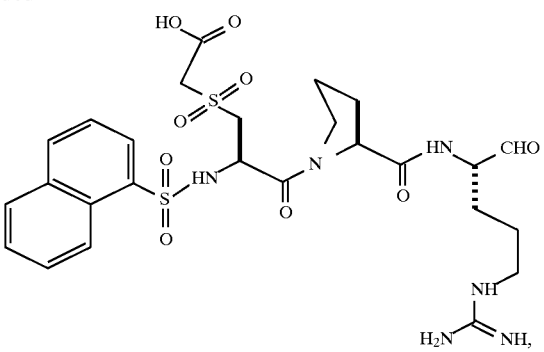
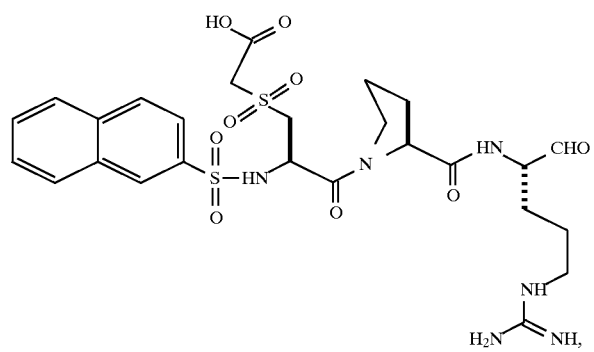
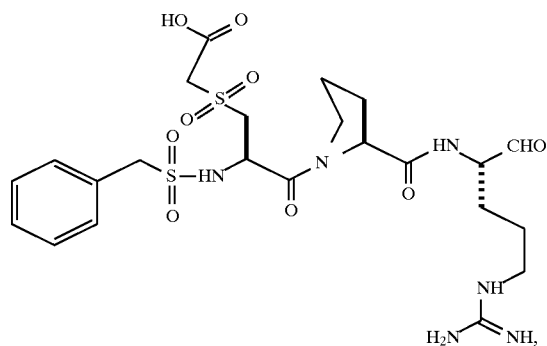
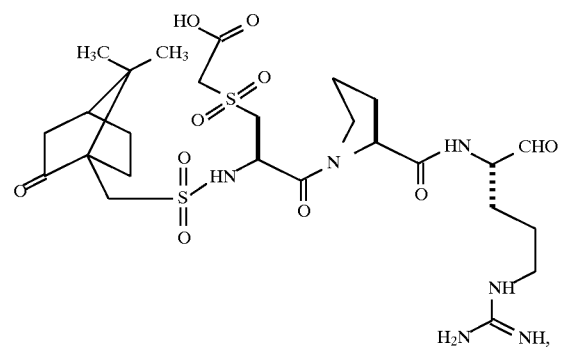
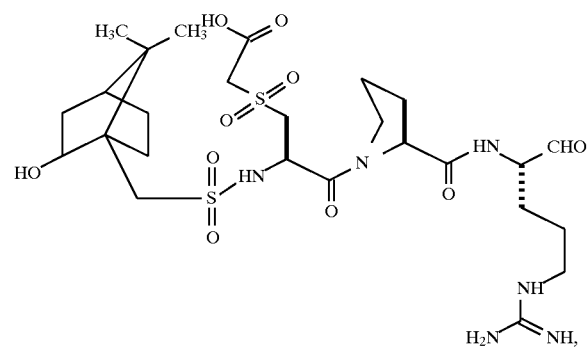
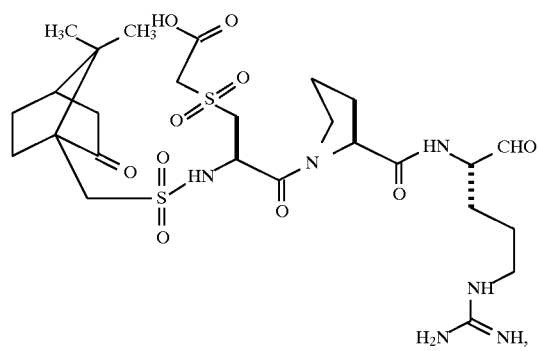

35
36
-continued
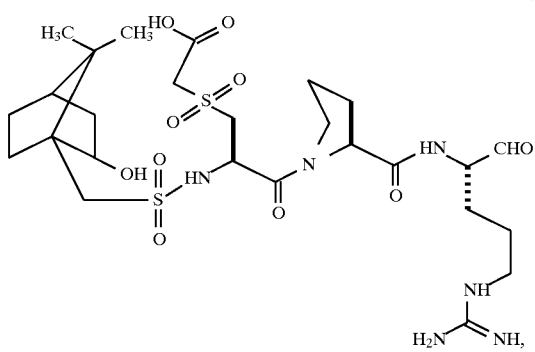
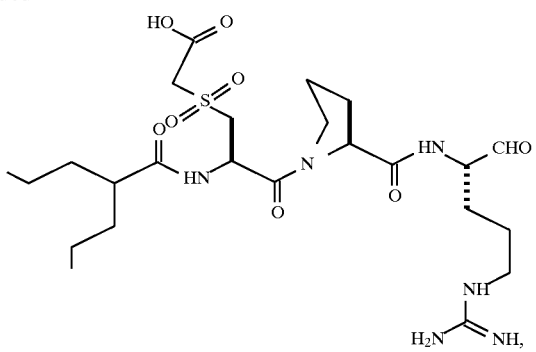
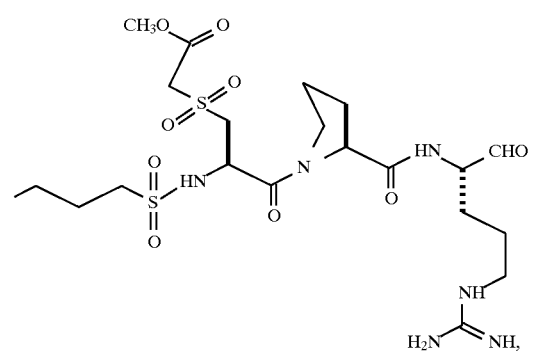
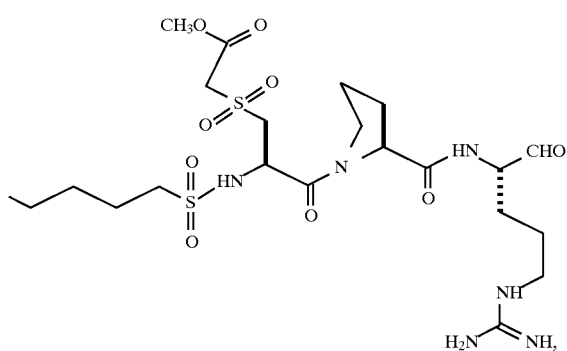
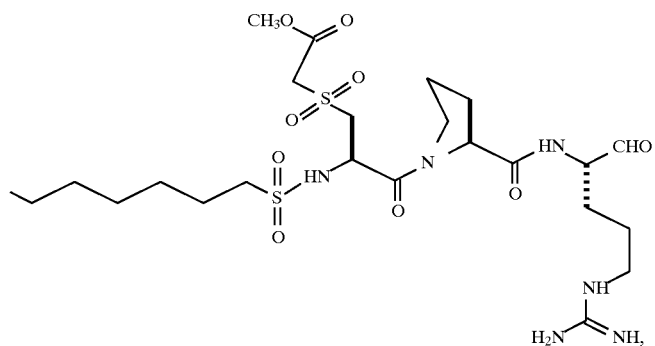
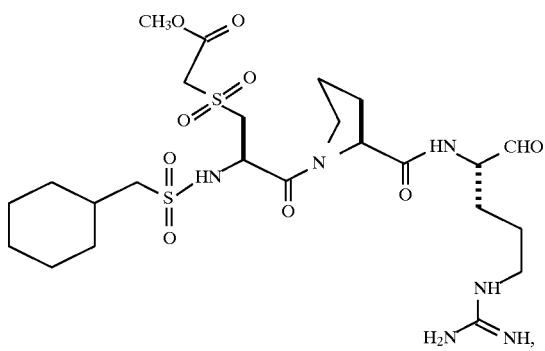
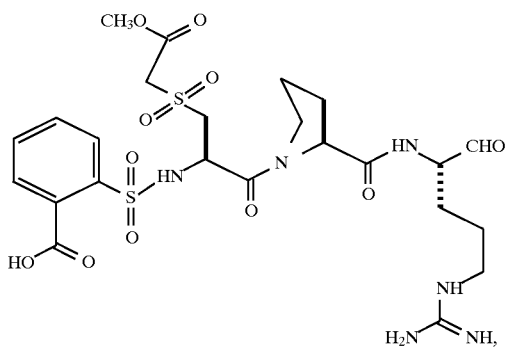

37 38
-continued
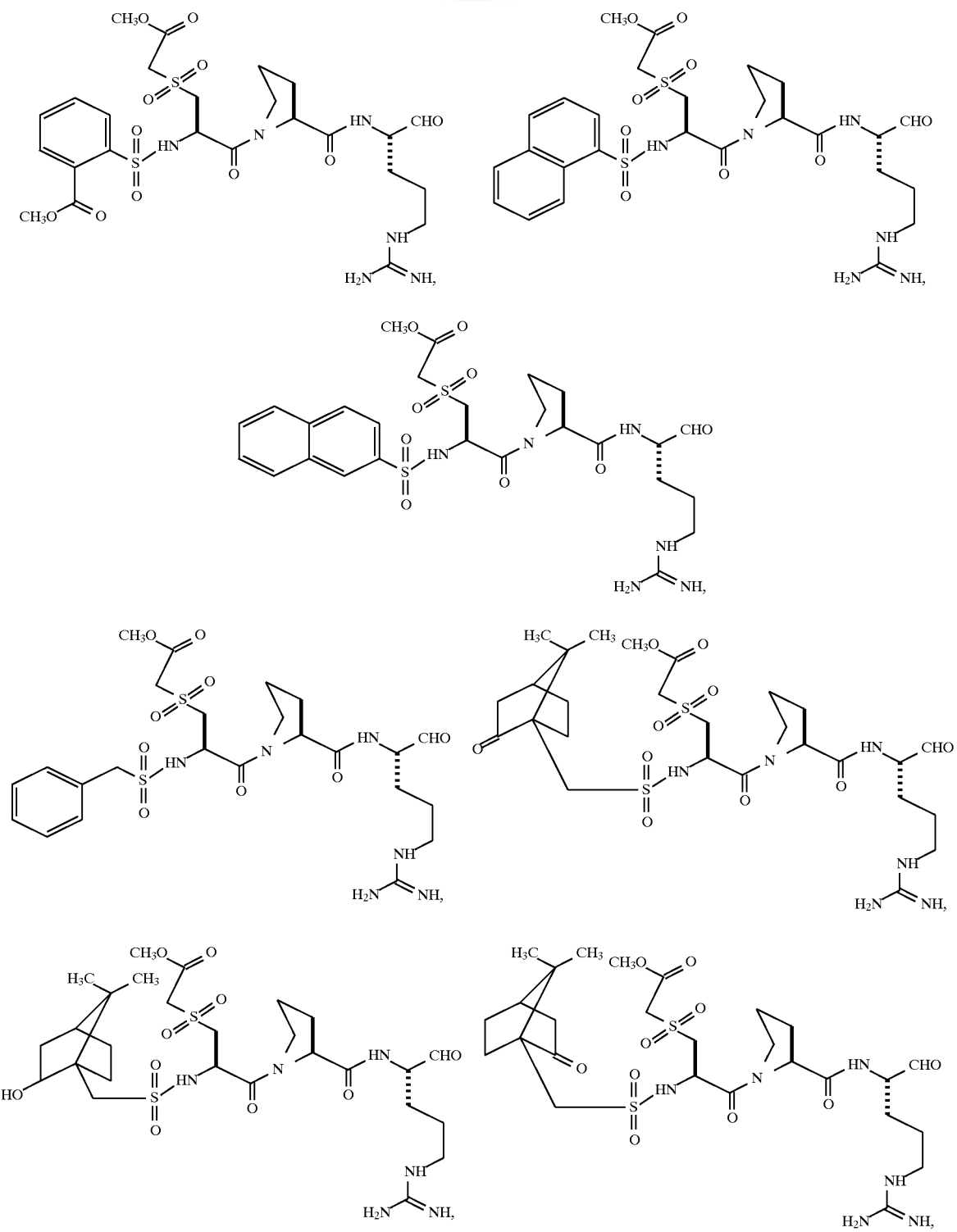

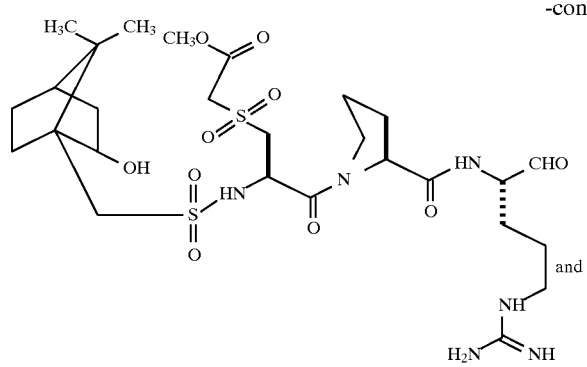
and
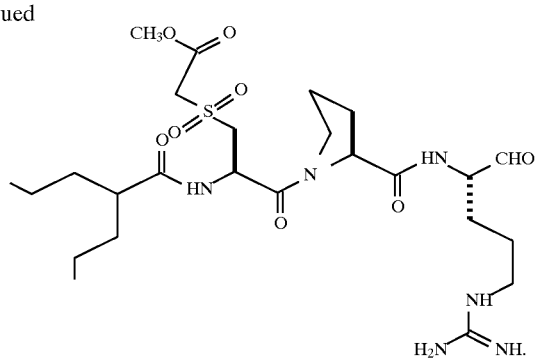

Also preferred are compounds having a substituted alkylene aryl group attached to the sulfur of the P3 amino acid. Especially preferred compounds include those of Examples 139 and 144.

Preparation of Preferred Compounds

The compounds of the present invention are synthesized by either solid or liquid phase methods. Under certain conditions, the liquid phase method disclosed herein is preferred.

Many of the starting materials used in either of these methods are readily available from chemical vendors as Aldrich, Sigma, Nova Biochemicals and the like.

During the synthesis of these compounds, the functional groups of the amino acid derivatives used in these methods are protected by blocking groups to prevent cross reaction during the coupling procedure. Examples of suitable blocking groups and their use are described in "The Peptides: Analysis, Synthesis, Biology", Academic Press, Vol. 3 (E. Gross & Meienhofer edit. 1981) and Vol. 9 (S. Udenfriend & J. Meienhofer edit. 1987), the disclosure of which are incorporated herein by reference.

The compounds of the present invention are synthesized by solid phase procedures described in the literature (see below) or by sequential chemical attachment of amino acid derivatives using the solid phase synthesis reagents and methods disclosed in the commonly assigned U.S. patent of Webb, T. R., U.S. Pat. No. 5,283,293 (issued Feb. 1, 1994), and the commonly assigned U.S. patent application of Webb, T. R., U.S. Ser. No. 07/807,474, filed Dec. 13, 1991, the disclosures of which are incorporated herein by reference.

Figure 1:
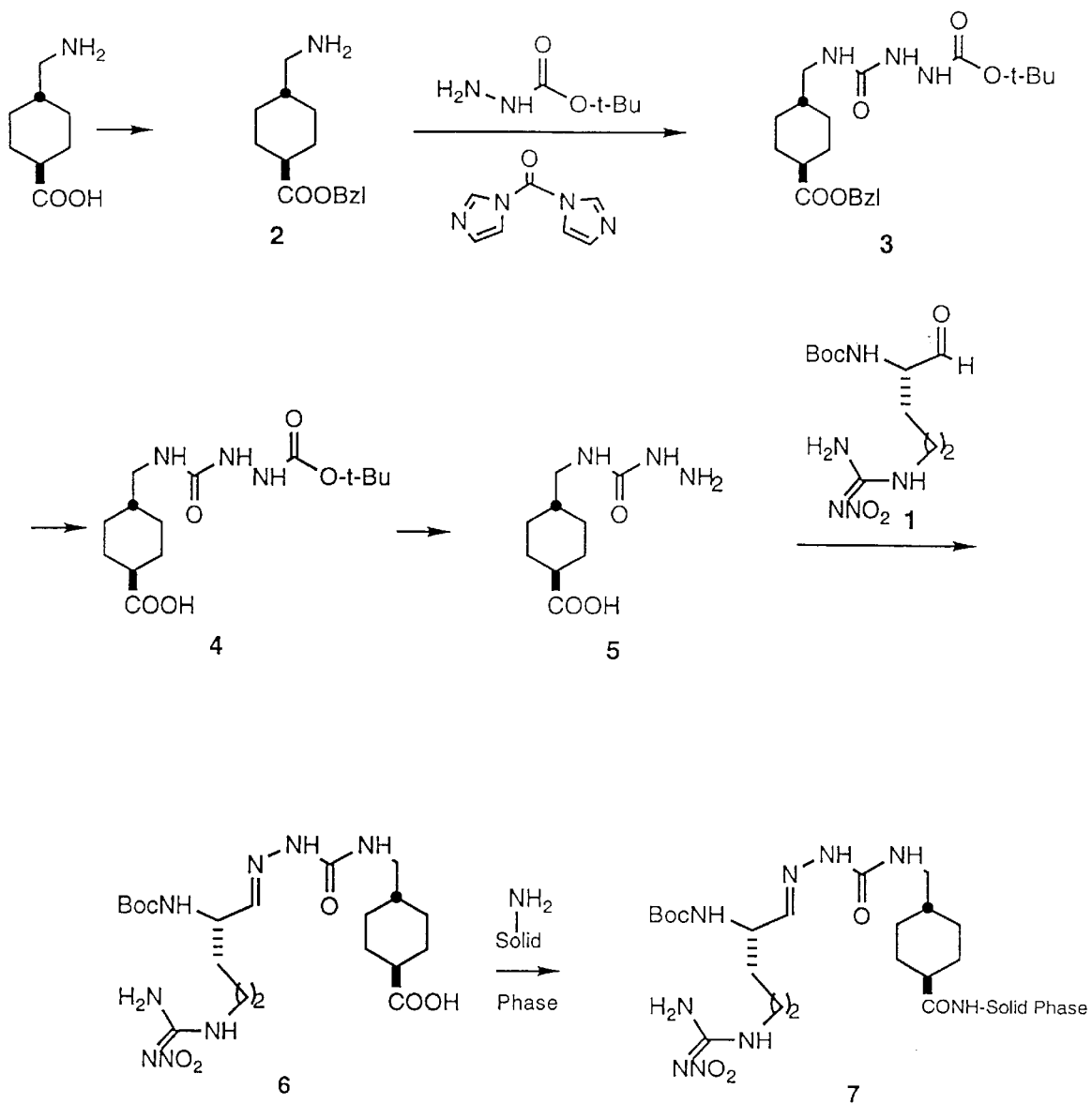
FIG. 1 depicts a reaction scheme describing a process for preparing a solid-phase reagent which may be used to make

FIG. 1 illustrates the synthesis of a solid phase reagent of Webb. This reagent is preferred for use in the solid phase method of Webb to make the compounds of the present invention. The details of how this reagent is made are provided in Examples 1 to 7.

Example 8 provides a preferred solid phase method to make the compounds of the present invention. In this method, the compound in its protected form is synthesized on a solid phase resin by the sequential coupling (using BOP or TBTU in combination with HOBt) of the amino acids or amino acid derivatives which comprise the sequence of the desired final compound. The compound is removed from the solid phase in the form of a deprotected semicarbazone by treatment with hydrofluoric acid/anisole. This treatment, in addition to removing the compound from the resin as a semicarbazone, deprotects by removing O-t-butyl and N-nitro protecting groups from the amino acid or amino acid side chain groups. The deprotected semicarbazone is then transformed by hydrolysis to a compound of the present invention by treatment with ethylacetoacetate in a pH 1 mixture of acetic acid, tetrahydrofuran and water. Examples 11, 18, 21, 24, 27, 40, 43, 46, 49, 56, 59, 66 and 69 are provided to further demonstrate the use of this solid phase synthesis method.

The peptide aldehydes of the present invention may also be synthesized by solution phase methods.

One preferred method is provided in Examples 28 through 33. In this method, N-Boc-$N^g$-nitro-L-arginine is first converted to N-Boc-$N^g$-nitro-L-argininol by treatment with borane-tetrahydrofuran complex. Next, N-Boc-$N^g$-nitro-L-argininol is converted to $N^g$-nitro-L-argininol by treatment with hydrochloric acid. Next, $N^g$-nitro-L-argininol having a free N-terminal amino group is coupled to a pre-synthesized dipeptide having a free C-terminal carboxyl group and a blocked N-terminal amino group to give dipeptide-$N^g$-nitro-L-argininol which is further converted to dipeptide-L-argininol by hydrogenation (on palladium on carbon). Finally, the dipeptide-L-argininol is converted to the compound of the present invention, dipeptide-L-argininal, by oxidation of the alcohol moiety of dipeptide-L-argininol to an aldehyde moiety using dichloroacetic acid and EDC in dimethylsulfoxide/toluene.

Another solution phase method for preparing peptide aldehydes is set forth in the commonly assigned and copending U.S. patent application Ser. No. 08/261,380 "Methods of Synthesis of Peptide Argininals" filed Jun. 17, 1994, the disclosure of which is incorporated herein by reference.

A preferred solution phase method for preparing peptide aldehydes of the present invention is depicted in FIG. 2 and specific Examples are set forth in Examples 123 to 144. According to this method, N-alpha-t-butoxycarbonyl-$N^g$-nitro arginine is converted to a $N^g$-nitro-L-argininal ethyl cyclol salt. The free alpha-amino of the cyclic argininal is then coupled to a pre-synthesized dipeptide having a free C-terminal carboxyl group and a blocked N-terminal amino group to give a dipeptide-nitro cycloargininal ethyl ether, which is converted to the dipeptide cycloargininal ethyl ether by hydrogenation using a suitable hydrogenation catalyst such as palladium on carbon. The hydrolysis of the cyclic argininal ring gives the product peptide argininal.

As depicted in FIG. 2, N-alpha-t-butoxycarbonyl-$N^g$-nitro-L-arginine A1 is converted to the corresponding N-alpha-t-butoxycarbonyl-$N^g$-nitro-arginine-(N-methyl, N-methoxyamide) A2 by a two step method. A solution of A1 in solvent, suitably tetrahydrofuran, is cooled and then N-methylpiperidine, followed by isobutyl chloroformate are added. To the resulting mixture, a cooled free base solution of N-methyl-O-methylhydroxylamine free base is slowly added. The free base solution is prepared in advance by treating a cooled mixture of N-methyl-O-methylhydroxylamine hydrochloride in solvent, suitably methylene chloride, with N-methylpiperidine. All procedures are carried out under nitrogen. The reaction is preferably carried out at about −5° C. After the reaction is complete as determined by thin layer chromatography, the product A2 is isolated by conventional procedures such as filtration, concentration under vacuum, column chromatography and the like.

The intermediate A2 is converted to N-alpha-t-butoxycarbonyl-$N^g$-nitro-L-argininal A3 by a two step procedure. To a cooled mixture of A2 in solvent, suitably tetrahydrofuran, a mixture of reducing agent, preferably lithium aluminum hydride, in solvent is added. The addition and reaction are preferably conducted at low temperature, preferably below −60° C. After the reaction is complete, the mixture is allowed to warm to about 0° C. and completeness of the reaction is confirmed (by, e.g., TLC). The mixture is then cooled again to about −70° C. and a solution of sodium bisulfate is slowly added. The temperature is maintained below −30° C. during the addition. After the reaction is complete, the reaction mixture is slowly allowed to warm to about 0° C. The product A3 is isolated by conventional procedures such as filtration, concentration under vacuum, washing, extraction, chromatography and the like.

Intermediate A3 is converted to the corresponding N-alpha-t-butoxycarbonyl-$N^g$-nitro-L-argininal ethyl cyclol A4 by treatment of an ethanolic solution of A3 with hydrochloric acid. The reaction may be conveniently carried out at room temperature. The ethylcyclol product A4 is isolated by conventional procedures such as column chromatography and evaporation under vacuum.

The ethyl cyclol intermediate A4 is preferably converted to its salt form, suitably its trifluoroacetate or, more preferably its hydrochloride from A5 by methods such as treatment with trifluoroacetic acid/methylene chloride (for the trifluoroacetate salt) or ethanol saturated with hydrogen chloride (for the hydrochloride salt).

The ethyl cyclol salt A5 is then coupled to N-protected dipeptide intermediate A6. Preparation of suitable dipeptide intermediates and deprotection of the FMOC-protected intermediate A10 to give A6 having a free carboxyl is described and exemplified, by Examples 128 to 136 and 140 to 141. Intermediates A6 and A5 are coupled by adding to a cooled (about 0° C.) solution of A6, HBTU and HOBT in solvent, preferably DMF/acetonitrile, A5 and 4-methylmorpholine. For convenience, the reaction is conducted at room temperature. The product A7 is isolated by conventional procedures such as evaporation under vacuum, washing, extraction, drying, chromatography and the like.

Compound A7 is converted to A8 by catalytic hydrogenation using a suitable hydrogenation catalyst such as palladium on carbon, followed by isolation of the product using conventional procedures such as filtration, vacuum evaporation, lyophilization and the like.

Compound A8 is converted to product A9 by hydrolysis of the argininal cyclol to give the argininal. Preferred means of hydrolyzing include treatment with aqueous acid. Preferred aqueous acids, include hydrochloric acid, $HPF_6$, methanesulfonic acid, perchloric acid, sulfuric acid, trifluoroacetic acid, trifluoromethanesulfonic acid, toluenesulfonic acid and the like. The hydrolysis reaction is quenched by addition of sodium acetate solution; and isolated by conventional procedures, conveniently by reverse phase HPLC.

Other methods for the solution synthesis of peptide aldehydes have been reported. For example, see McConnell et al., supra; at 87 and references therein; Bajusz et al., J. Med. Chem., 33: 1729 (1990); Kawamura et al., Chem. Pharm. Bull., 17: 1902 (1969), and Someno et al., Chem. Pharm. Bull., 34: 1748 (1986).

According to another aspect, the present invention is directed to pharmaceutically acceptable salts of the compounds of formula (IA). "Pharmaceutically acceptable salt" includes within its definition salts of the compounds of the present invention derived from the combination of such compounds and an organic or inorganic acid. In practice, the use of the salt form amounts to use of the base form. The compounds of the present invention are useful in both free base and salt form, with both forms being considered as being within the scope of the present invention. These salts include acid addition salts, for example, salts of hydrochloric acid, hydrobromic acid, acetic acid, benzene sulfonic acid and other suitable acid addition salts.

Selection of Preferred Compounds

The compounds of the present invention are screened for their ability to inhibit thrombin or factor Xa and plasmin as set forth below. Certain of the preferred compounds are distinguished by their ability to inhibit thrombin, while not substantially inhibiting plasmin. With respect to thrombin and plasmin and as used herein, the term "not substantially inhibiting" means that the $IC_{50}$ (or $K_i$) for plasmin for a given compound is greater than or equal to its $IC_{50}$ (or $K_i$, respectively) for thrombin.

Alternatively, certain of the preferred compounds are distinguished by their ability to inhibit factor Xa, while not substantially inhibiting plasmin. With respect to factor Xa and plasmin and as used herein, the term "not substantially inhibiting" means that the ICSO (or $K_i$) for plasmin for a given compound is greater than or equal to its $IC_{50}$ (or $K_i$, respectively) for factor Xa.

The compounds of the present invention are dissolved in buffer to give solutions containing concentrations such that assay concentrations range from 0 to 100 micromolar. In the assays for thrombin and plasmin, a chromogenic synthetic substrate is added to a solution containing test compound and the enzyme of interest and the residual catalytic activity of that enzyme is determined spectrophotometrically. Likewise, in the assays for factor Xa and plasmin, a chromogenic synthetic substrate is added to a solution containing test compound and the enzyme of interest and the residual catalytic activity of that enzyme is determined spectrophotometrically. The $IC_{50}$ of a compound of the present invention is determined from the rate of substrate turnover caused by the specific enzyme being measured. $IC_{50}$ is that concentration of test compound giving 50% inhibition of the rate of substrate turnover. Likewise, the $K_i$ of a compound of the present invention is determined from the rate of substrate turnover caused by the specific enzyme being measured at various enzyme concentrations. $K_i$ is that concentration of test compound giving 50% inhibition of the rate of substrate turnover. Example A and B provides an exemplar of the in vitro assays used to select the compounds of the present invention.

Preferred compounds of the present invention have an $IC_{50}$ (or $K_i$) of 0.001 to 200 nM in the thrombin assay, and preferably the $IC_{50}$ (or $K_i$) for plasmin will not be less than the $IC_{50}$ (or $K_i$) for thrombin. More preferred are compounds having an $IC_{50}$ (or $K_i$) of 0.001 to 100 nM in the thrombin assay. Especially preferred are compounds having an $IC_{50}$ (or $K_i$) of about 0.001 to 20 nM in the thrombin assay and having a quotient of ($IC_{50}$ for plasmin)/($IC_{50}$ for thrombin) [or ($K_i$ for plasmin)/($K_i$ for thrombin)], of about 2 to 100,000, preferably 10 to 100,000, and more preferably 100 to 100,000.

Alternatively, preferred compounds of the present invention have an $IC_{50}$ ($K_i$) of 0.001 to 200 nM in the factor Xa assay, and preferably the $IC_{50}$ ($K_i$) for plasmin will not be less than the $IC_{50}$ ($K_i$) for factor Xa. More preferred are compounds having an $IC_{50}$ ($K_i$) of 0.001 to 100 nM in the factor Xa assay. Especially preferred are compounds having an $IC_{50}$ ($K_i$) of about 0.001 to 20 nM in the factor Xa assay and having a quotient of ($IC_{50}$ for plasmin)/($IC_{50}$ for factor Xa) [or ($K_i$ for plasmin)/($K_i$ for factor Xa)], of about 2 to 100,000, preferably 10 to 100,000, and more preferably 100 to 100,000.

Pharmaceutical Compositions

In another aspect, the present invention encompasses pharmaceutical compositions prepared for storage or administration which comprise a therapeutically effective amount of a compound of the present invention in a pharmaceutically acceptable carrier.

The "therapeutically effective amount" of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which as noted those skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use are well known in the pharmaceutical art, and are described, for example, in *Remington's Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixers for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutcial compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxilliary substances, such as wetting agents, pH buffering agents, and the like. If desired, absorption enhancing preparations (e.g., liposomes) may be utilized.

Utility and Methods

Compounds of the present invention when made and selected as disclosed are useful as potent inhibitors of thrombin in vitro and in vivo. Alternatively, compounds of the present invention when made and selected as disclosed are useful as potent inhibitors of factor Xa in vitro and in vivo. As such, these compounds are useful as in vitro diagnostic reagents to prevent the clotting of blood and as in vivo pharmaceutical agents to prevent thrombosis in mammals suspected of having a condition characterized by abnormal thrombosis.

The compounds of the present invention are useful as in vitro diagnostic reagents for inhibiting clotting in blood drawing tubes. The use of stoppered test tubes having a vaccum therein as a means to draw blood obtained by venipuncture into the tube is well known in the medical arts. Kasten, B. L., "Specimen Collection", *Laboratory Test Handbood*, 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of factor Xa or thrombin, and as such, can be incorporated into blood collection tubes to prevent clotting of the mammalian blood drawn into them.

The compounds of the present invention are used alone, in combination of other compounds of the present invention, or in combination with other known inhibitors of clotting, in the blood collection tubes. The amount to be added to such tubes is that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are added to blood collection tubes in such amounts that, when combined with 2 to 10 mL of mammalian blood, the concentration of such compounds will be sufficient to inhibit clot formation. Typically, the required concentration will be about 1 to 10,000 nM, with 10 to 1000 nM being preferred.

The compounds of the present invention are useful as a pharmaceutical agent for preventing thrombosis in a mammal suspected of having a condition characterized by abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The present invention includes methods for preventing a condition in a mammal suspected of having a condition characterized by abnormal thrombosis, comprising administering to said mammal a therapeutically effective amount of a compound or a pharmaceutical composition of the present invention.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including parenterally, intravenously, subcutaneously, intramuscularly, colonically, rectally, nasally or intraperitoneally, employing a variety of dosage forms. Administration is preferably parenteral, such as intravenous on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a therapeutically effective amount of the compounds or pharmaceutical compositions of the present invention will vary depending upon the age, weight and mammalian species treated, the particular compounds employed, the particular mode of administration and the desired affects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts. Typically, administration of the compounds or pharmaceutical composition of the present invention is commenced at lower dosage levels, with dosage levels being increased until the desired effect of preventing in vivo thrombosis is achieved which would define a therapeutically effective amount. For the compounds of the present invention, alone or as part of a pharmaceutical composition, such doses are between about 0.01 mg/kg and 100 mg/kg body weight, preferably between about 0.01 and 10 mg/kg, body weight.

To assist in understanding, the present invention will now be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Preparation of alpha-N-t-butoxycarbonyl-$N^g$-nitroargininal

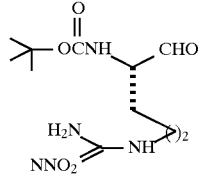

A. Procedure 1

The following procedure for the synthesis of alpha-t-butoxycarbonyl-$N^g$-nitro-argininal, the title compound, is an example of a general procedure for the preparation of Boc-amino acid aldehydes, see Patel et al., Biochim. Biophys. Acta, 748, 321–330 (1983).

In 200 mL dry THF, 12.7 g Boc-$N^g$-nitro-arginine (40 mmoles) and 7.0 g carbonyldiimidazole (CDI; 43 mmoles) were added at room temperature and allowed to stir for 30 minutes. The reaction mixture was cooled to −78° C. and 35 mL of a solution of LiAlH$_4$ (1M in THF) were added dropwise over thirty minutes. The reaction was allowed to stir for an additional hour at −78° C. Next, 18 mL of acetone were added and this mixture was quickly added to 400 mL of 1N HCl. The mixture was extracted twice with 100 mL of ethyl acetate. The ethyl acetate washes were combined and then washed two times each with 100 mL water, 100 mL saturated NaHCO$_3$ and 100 mL saturated NaCl. The solution was dried (MgSO$_4$) and concentrated to a foam. The crude weight of the title compound was 6.36 g (21 mmole; yield 52%).

B. Procedure 2

Alternatively, the title compound was synthesized by a modification of the procedure of Fehrentz, J. A. and Castro, B., Synthesis, 676 (1983).

11.4 mL of N-methyl piperidine was slowly added to a stirred suspension of 8.42 g (94 mmole) of N,O-dimethylhydroxylamine hydrochloride in 75 mL dichloromethane which had been cooled to about 0° C. The solution was allowed to stir for 20 minutes which gave the free hydroxylamine, then was kept cold for use in the next step.

In a separate flask, 30.0 g (94 mmole) of Boc-$N^g$-nitroarginine was dissolved by heating in about 1400 mL of THF, then the mixture was cooled under nitrogen to 0° C. 11.4 mL of N-methylpiperidine and 12.14 mL (94 mmole) of isobutylchloroformate was added and the mixture stirred for 10 minutes. The free hydroxylamine prepared above was added all at once and the reaction mixture was allowed to warm to room temperature, then stirred overnight.

The resulting precipitate was filtered off, then washed with 200 mL of THF. After concentrating the filtrates to about 150 mL under vacuum, 200 mL of ethyl acetate was added, followed by ice to cool the solution. The cooled ethyl acetate phase was washed with two 75 mL portions of 0.2N hydrochloric acid, two 75 mL portions of 0.5N sodium hydroxide, one portion of 75 mL of brine, then the organic phase was dried over MgSO$_4$. Upon concentration in vacuum, 22.7 g (70% yield) of solid Boc-$N^g$-nitroarginine N-methyl-O-methylcarboxamide was recovered. Thin layer chromatographic analysis in 9:1 dichloromethane/methanol (silica gel) showed one spot.

A flask was placed under a nitrogen atmosphere and cooled to −50° C., then charged with 70 mL (70 mmole) of 1N lithium aluminum hydride (in THF) and 500 mL of dry THF. 50 mL of a solution containing 66 mmole of Boc-$N^g$-nitroarginine N-methyl-O-methylcarboxamide in dry THF was slowly added while the temperature of the reaction mixture was maintained at −50° C. After allowing the reaction mixture to warm to 0° C. by removal of the cooling, it was recooled to −30° C., at which temperature, 100 mL (0.2 mole) of 2N potassium bisulfate was added with stirring over about a 10 to 15 minute period. The reaction mixture was then allowed to stir at room temperature for 2 hours. After filtering off the precipitate, the filtrate was concentrated to 100 mL under vacuum. The concentrate was poured into 800 mL ethyl acetate, then was successively washed with two 50 mL portions of 1N hydrochloric acid, two 50 mL portions of saturated sodium bicarbonate, one 50 mL portion of brine. The combined aqueous extracts were extracted with 3–100 mL portions of ethyl acetate. All of the ethyl acetate washes were combined, then was dried over MgSO₄. The mixture was concentrated under vacuum to yield 18.5 g (95%) of the title compound.

Example 2

Preparation of trans-4-(aminomethyl)-cyclohexane carboxylic acid benzyl ester para-touluenesulfonate salt

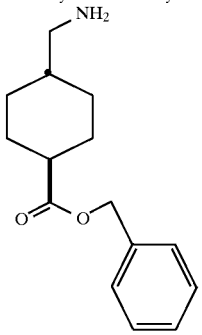

50 g (0.318 moles) of trans-4-(aminomethyl)cyclohexane carboxylic acid, 61.7 g (0.324 moles) p-toluenesulfonic acid, 250 mL (2.4 moles) benzyl alcohol and 250 mL toluene were combined and stirred. The mixture was refluxed for 24 hours and the liberated water was removed azeotropically by means of a Dean-Stark apparatus. A clear solution was obtained after 5 hours of refluxing. The solution was allowed to cool to room temperature, and the product crystallized. The mixture was vacuum filtered, washed with ether and dried in a vacuum oven to give 128.12 g (96% yield.). Reference: Greenstein, Jesse P.; Winitz, Milton. *Chemistry of the Amino Acids*. vol. 2, (1986), 942. ¹H NMR (CD₃OD) d 1.05 (m, 2H), 1.43 (m, 2H), 1.59 (m, 1H), 1.85 (m, 2H), 2.03 (m, 2H), 2.33 (m, 1H), 2.35 (s, 3H), 2.75 (d, 2H), 5.09 (s, 2H), 7.23 (d, 2H), 7.32 (m, 5H), 7.69 (d, 2H). M.P. 154°–156° C.

Example 3

Preparation of 1-t-butoxycarbonyl-semicarbazidyl-trans-4-methyl cyclohexane carboxylic acid benzyl ester

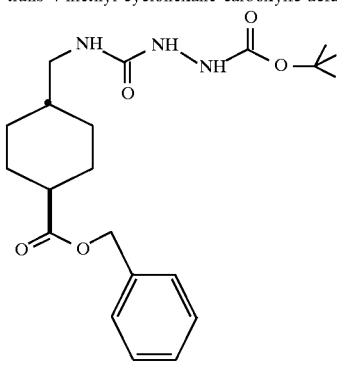

3.24 g (0.02 moles) carbonyldiimidazole (CDI) were dissolved in 45 mL of dimethylformamide (DMF) at room temperature under nitrogen. A solution of 2.48 g (0.02 moles) t-butyl carbazate in 45 mL DMF was added dropwise. Next 8.38 g (0.02 moles) of solid benzyl ester of Example 2 was added, followed by the dropwise addition of 3.06 mL of triethylamine (TEA) over a 30 minute period. The reaction was allowed to stir at room temperature under nitrogen for one hour. Water (100 mL) was added and this mixture was extracted three times with 50 mL of ethyl acetate. The ethyl acetate layers were combined and extracted two times each with 75 mL 1N HCl, H₂O, NaHCO₃, NaCl and dried with MgSO₄. The mixture was filtered and the solution was concentrated to give an oil. This material could be purified by recrystallization from ethyl acetate/hexanes (M.P.=106°–108° C.) or used directly in the next step. ¹H NMR (CDCl₃) d 0.94 (m, 2H), 1.42 (m, 2H), 1.45 (s, 9H), 1.81 (m, 2H), 2.02 (m, 2H), 2.27 (m, 1H), 3.17 (t, 2H), 5.09 (s, 2H), 5.51 (t, 1H), 6.46 (s, 2H), 7.34 (m, 4H).

Example 4

Preparation of 1-(t-butoxycarbonyl)-3-semicarbazidyl-trans-4-methyl-cyclohexane carboxylic acid

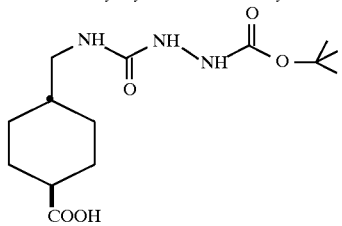

To the crude Boc-benzyl ester of Example 3, 250 mL of methanol (MeOH) and 500 mg of 10% palladium on carbon were added. After shaking on the hydrogenator for one hour at 5 psi, the mixture was filtered with Celite through a fine fritted filter. The solution was concentrated to a foam, dichloromethane was added and a precipitate formed. The mixture was kept 5° C. for 65 hours. The crystallized material was filtered with ether and 4.0 g of crude product were obtained (12.7 mmoles; yield 62% overall yield from the compound of Example 2) ¹H NMR (CD₃OD), d 0.96, (m, 2H), 1.42 (m, 2H), 1.46 (s, 9H), 1.82 (m, 2H), 1.97 (m, 2H), 2.18 (m, 1H), 3.0 (t, 2H). M.P.=185°–189° C.

Example 5

Preparation of semicarbazidyl-trans-4-methyl cyclohexane carboxylic acid trifluoroacetate salt

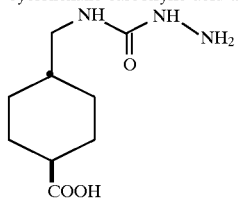

315 mg (1 mmole) of compound of Example 4 was added to 10 mL of trifluoroacetic acid (TFA) at 0° C. and the resulting solution was allowed to stir for 30 minutes. After this time the solution was added dropwise to 75 mL of diethyl ether. A precipitate formed, and the mixture was filtered and washed with diethyl ether. Weight of crude product was 254 mg, 0.77 mmoles; yield (77%). ¹H NMR (CD₃OD), d 1.0 (m, 2H), 1.38 (m, 2H), 1.43 (m, 1H), 1.84 (m, 2H), 2.01 (m, 2H), 2.22 (m, 1H), 3.04 (d, 2H). M.P.= 154°–156° C.

Example 6

Preparation of alpha-(t-butoxycarbonyl)-N^g-nitro
argininal-semicarbazonyl-trans-4-methyl-cyclohexane
carboxylic acid

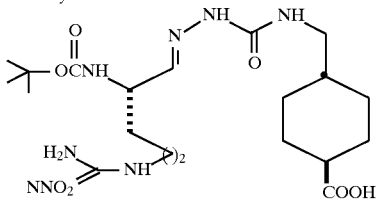

A solution of 13.7 g (41.6 mmoles) of the compound of Example 5, 18.0 g (~59 mmoles) of crude compound of Example 1 in 135 mL ethanol containing 45 mL of water, was treated with 9.41 g (69 mmoles) of sodium acetate (NaOAc) and refluxed for one hour. This solution was allowed to cool and then poured into 0.1N HCl and extracted three times with ethyl acetate. The combined organic phase was washed with water, then brine, dried (MgSO$_4$) and concentrated to a small volume. This cloudy mixture was allowed to set overnight at 5° C. to precipitate the product, which was isolated by filtration and dried under vacuum. This gave 9.9 g, 47% yield based on the amount of the compound of Example 5 used. $^1$H NMR (CD$_3$OD) d 1.0 (m, 2H), 1.43 (s, 9H), 1.45–2.20 (m, 13H), 3.09 (d, 2H), 3.30 (m, 2H), 4.18 (bs, 1H), 7.10 (d, 1H). M.P.=162°–163° C.

Example 7

Synthesis of Semicarbazone Solid Phase

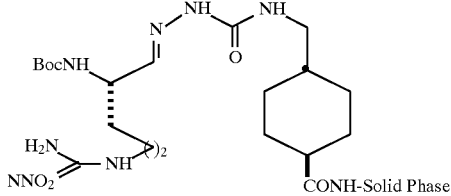

The title resin, a solid phase reagent, was prepared by coupling of the compound of Example 6 to methyl-benzhydralamine (MBHA) resin as follows.

MBHA resin (0.8 g, 0.5 mmoles amino groups) was placed in a reaction vessel and washed successively one time with DCM, three times with DMF, two times with 10% DIEA/DMF, and four times with DMF. Each wash is done by adding 10 mL of solvent to the resin, agitating the mixture for 1–2 minutes, and then draining the solvent.

The washed MBHA resin was placed in a reaction vessel and 5 mL of DMF was added. To this mixture, NMM (0.102 mL, 1 mmole), BOP (443 mg, 1 mmole) and the compound of Example 6 (500 mg, 1 mmole) was added. The mixture was then mixed on a rotating wheel for 16 hours. After this time, the resin was filtered off and washed successively three times with DMF, two times with 10% DIEA/DMF and three times with DMF. The resin was then washed successively one time with DCM, one time with methanol and one time with diethyl ether to yield the title resin. Each wash was again done by adding 10 mL of solvent to the resin, agitating the mixture for 1–2 minutes, and then draining the solvent.

The title resin showed a 98–99% coupling yield by ninhydrin. The yield was calculated on the basis of the mmoles/g of amino groups on the starting MBHA resin.

Example 8

Solid Phase Synthesis

The compounds of the present invention may be made by the solid-phase synthesis method as described in this example. This synthesis method is carried out in three stages—coupling, cleavage and hydrolysis.

Washing of the resin is common step in this procedure. Accordingly, unless otherwise specified, a wash is defined as the adding 5–10 mL of a specified solvent to the resin, agitating the mixture for 1–2 minutes, and then draining the solvent away from the resin.

A. Coupling

In the first stage of the present method, specified intermediates are coupled to the resin of Example 7 in the following manner:

1. The resin of Example 7 (0.5 g, 0.25 mmole alpha-amino groups) is placed in a reaction vessel and washed three times with DCM.

2. The alpha-amino groups of the resin are deprotected by twice immersing the resin in 5–10 mL of 50% TFA in DCM, with first time for 5 minutes and the second time for 30 minutes. The resin is then washed two times with DMF, two times with DCM, and two times with DMF.

3. The deprotected resin is neutralized by immersing the resin in 5–10 mL of 5% DIEA in DMF for 7 minutes. The resin is then washed two times with DMF, two times with DCM, and two times with DMF.

4. The deprotected resin is combined with 5 mL of DMF and then 1.0 mmole of amino acid, amino acid analog, peptide or peptide analog (which has a free C-terminal carboxy group, is protected by a Boc group or otherwise blocked at the N-terminal amino group, and suitably protected at all other reactive functionalities), TBTU (0.321 mg, 1.0 mmole), HOBt (0.135 mg, 1.0 mmole), NMM (0.11 mL, 1.0 mmole) and 3 mL of DMF, then the mixture is agitated for three hours. BOP (0.442 mg, 1.0 mmole) may be substituted for the TBTU.

5. If further amino acids, amino acid analogs, peptides or peptide analogs are to be sequentially coupled, steps 2–4 is repeated until the desired compound is achieved.

6. The resin is separated from the DMF solution and is washed three times with DMF, three times with DCM, three times with methanol, and three times with diethyl ether. The resin is then dried under vacuum.

B. Cleavage

In the second stage of the present method, the desired compound in the form of a semicarbazone intermediate is cleaved from the resin.

The dried resin (0.50 g) from Step A is placed in a reaction vessel and anisole (0.5 mL) is added. Thiocresol (0.1 mL) is additionally added for the cleavage of certain specified compounds of the present invention. After cooling the reaction vessel to −20° C., gaseous hydrofluoric acid (12.0 mL) is distilled into the reaction mixture with stirring.

After stirring for 30 minutes at −20° C., the reaction mixture is warmed to −10° C. and stirred for an additional 2 hours at this temperature. After this time, the reaction mixture is warmed to 0° C. and the hydrofluoric acid is distilled off with a stream of N$_2$. The resin is then washed twice with diethyl ether.

The title compound is extracted from the resin by successively washing the resin with 0.1M ammonium bicarbonate (50 mL) and water (100 mL), which are then combined and extracted three times with diethyl ether using 25 mL of the solvent for each extraction. The extracted aqueous solution is frozen and lyophilized to give the crude semicarbazone of title product.

C. Hydrolysis

In the third stage of the present method, the semicarbazone intermediate is hydrolyzed to the compound of the present invention.

Crude semicarbazone (0.25 mmole) from Step B is placed in a reaction vessel, followed by 6 mL acetic acid, 12 mL THF and 6 mL of water (adjusted to pH 1 with trifluoroacetic acid). Stirring is commenced and 1 mL of ethyl acetoacetate is added. Additional 1 mL portions of ethyl acetoacetate are added every 1–8 hours until the semicarbazone is hydrolyzed to the title compound. The reaction mixture is then reduced to dryness under vaccum to give crude title compound.

The crude title compound is purified by high pressure liquid chromatography, using a reverse-phase column containing a C-18 resin comprised of 10 micron-size gel particles with a 300 angstrom pore size. The column is eluted with a water-acetonitrile (both containing 0.1% trifluoroacetic acid) gradient, where the gradient is run from 5% to 40% acetonitrile. The column fractions are analyzed by analytical high pressure liquid chromatography using a reverse phase C-18 column and the same gradient system. The fractions containing pure product are pooled, then lyophilized to yield the title product.

Example 9

Preparation of L-methionine sulfone-L-proline-O-benzyl ester hydrochloride salt

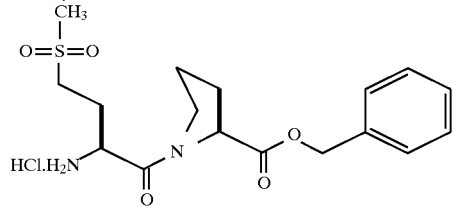

A. Procedure 1

N-Boc-L-methionine sulfone-L-proline-O-benzyl ester was prepared by adding to a solution of N-Boc-L-methioninesulfone (14.0 g, 50.0 mmole) in dichloromethane (150 mL) at 0° C., HOBt (10.1 g, 75 mmole) followed by DCC (11.33 g, 55.0 mmole). The mixture was stirred for 10 minutes, and then proline benzyl ester hydrochloride salt (50.0 mmole, 12.0 g) was added followed by NMM (100 mmole, 10.9 mL). The resulting mixture was stirred in an ice bath and allowed to come to room temperature over 12 hours. The mixture was filtered to remove dicyclohexylurea and ethyl acetate (300 mL) is added. The organic phase was then added to a separatory funnel and washed with saturated aqueous sodium bicarbonate, brine and then 1M aqueous HCl. The organic phase was dried over magnesium sulfate and then filtered. The organic phase was then reduced on a rotary evaporator under vacuum and then on a high vacuum line to remove traces of solvent to provide 23.5 g of a white solid (100%). Rf=0.34 (silica, 5:95 methanol/chloroform).

To a solution of N-Boc-L-methionine sulfone-L-proline-O-benzyl ester (23.5 g, 50 mmole) in dry dioxane (300 mL) was added 100 mL of a 4M HCl/dioxane solution. The mixture was then stirred at room temperature for 1 hour until the starting material disappeared as shown by thin layer chromatography analysis (silica, 10% chloroform in methanol). Diethyl ether was added to the mixture to precipitate the title compound as a white hydrochloride salt. The mixture was filtered on a Büchner funnel and the solid was then dried under high vacuum to give 20.16 g (100%) of the title compound as a white solid.

B. Procedure 2

Alternatively, the title compound was synthesized by the following method.

To a solution of N-Boc-L-methionine sulfone (5 g, 20 mmole) in 80 mL of dry DMF was added L-proline-O-benzyl ester hydrochloride salt (4.8 g, 20 mmole) followed by BOP (8.9 g, 20 mmole) and NMM (5.5 mL, 20 mmole). The mixture was stirred for 16 hours at room temperature. The reaction mixture was dissolved in 600 mL of ethyl acetate and washed with 200 mL each of water, 1M aqueous HCl, water, saturated aqueous sodium bicarbonate and brine. The organic phase was dried over magnesium sulfate, filtered and the solvent removed under vacuum to yield an oil.

To the solution of the resulting oil in 20 mL dichloromethane, 100 mL of a 4M solution of HCl in dioxane was added. After stirring for 16 hours, the solvent was removed under vacuum. The resulting oil was precipitated using diethyl ether, filtered and dried under vacuum to provide 7.49 g (86% yield) of the title compound as a white solid. Thin layer chromatography analysis of the title compound showed a single spot with Rf=0.1 (silica, 1:9 methanol/dichloromethane).

Example 10

Preparation of N-(1-butanesulfonyl)-L-methioninesulfone-L-proline

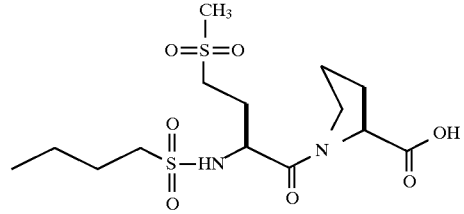

A 6.0 g (12.4 mmole) of the compound of Example 9 was reacted with 2.07 mL (16 mmole) of 1-butanesulfonylchloride and 5.0 mL (36 mmole) of triethylamine in dichloromethane from 0° C. to room temperature. The reaction mixture was poured into saturated aqueous bicarbonate and extracted with ethyl acetate (2×100 mL). The organic phase was washed with brine and 1M aqueous HCl. The organic phase was separated and dried over magnesium sulfate, filtered and reduced under vacuum to give 5.73 g of a viscous oil.

The oil was mixed with 2M potassium hydroxide (20 mL) and 100 mL methanol at room temperature for two hours. The methanol was reduced under vacuum and the aqueous solution was then washed with ether (2×50 mL) and then neutralized with 1M HCl to a pH of 1. The aqueous solution was then extracted with ethyl acetate (2×100 mL) and dried over MgSO$_4$, filtered and reduced under vacuum to give 2.85 g of the title compound as a viscous foamy solid. The overall yield was 60.5%.

Example 11

Preparation of N-(1-butanesulfonyl)-L-methioninesulfone-L-proline-L-argininal

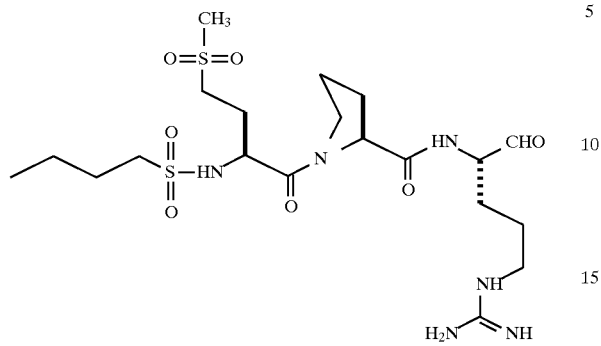

The title compound was prepared in the same manner as described in Example 8.

The compound of Example 10 was attached to the resin of Example 7. After cleavage of the title compound as a protected semicarbazone from the resin, the semicarbazone was hydrolyzed to give the title compound.

Fast atom bombardment mass spectrometry confirmed the theoretical molecular weight of 538.2.

Example 12

Preparation of cyclohexylmethylsulfonate sodium salt

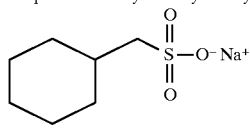

To a solution of sodium bisulfite (32 g, 307 mmole) in $H_2O$ (200 mL) was added cyclohexylmethyl bromide (21 mL, 150 mmole). The mixture was then stirred vigorously while heated at reflux for 48 hours. Upon cooling to room temperature, a white precipitate formed. The precipitate was collected on a Büchner funnel and washed with diethyl ether to wash away residual cyclohexylmethyl bromide. The white plate-like solid was dried under high vacuum overnight to provide 11.8 g (39%) of the title compound which had a m.p.>400° C.

Example 13

Preparation of cyclohexylmethyl sulfonyl chloride

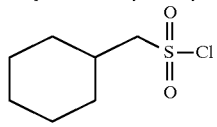

To the compound of Example 12 (4.0 g, 20 mmole) was added $POCl_3$ (15 mL) and the mixture heated at 100° C. for 48 hours. Upon cooling to room temperature the mixture was poured onto crushed ice and then the aqueous phase was extracted with ethyl acetate (2×100 mL). The combined organic extracts were then washed with saturated aqueous sodium bicarbonate (2×50 mL), brine (100 mL) and then dried over $MgSO_4$, filtered and the solvent was evaporated under vacuum to provide 3.46 g of the title compound as a light yellow oil. Thin layer chromatography analysis of the title compound showed a single spot with $R_f$=0.53 (silica, 4:1 hexanes/ethyl acetate).

Example 14

Preparation of N—Boc-L-methionine sulfone-O-benzyl ester

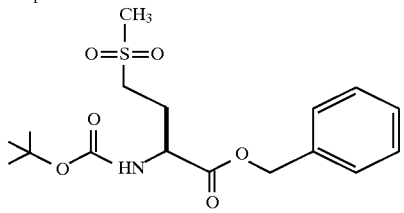

To a solution of N-Boc-L-methionine sulfone (50 g, 178 mmole) in dry THF (500 mL) which had been chilled to 0° C., carbonyl diimidazole (34.6 g, 214 mmole) was added in small portions. After 30 minutes, the mixture was warmed to room temperature for 2 hours until all of the $CO_2$ evolution ceased. After this time, benzyl alcohol (27.6 mL, 267 mmole) was added and the reaction stirred for 12 hours.

The reaction mixture was then reduced in volume under vacuum and the resulting residue was diluted with ethyl acetate (500 mL). The organic phase was then washed with saturated bicarbonate (1×100 mL), brine (100 mL), then saturated aqueous citric acid (1×100 mL), dried over $MgSO_4$, filtered and the solvent removed under vacuum to provide a white solid. The white solid was washed with a 1:1 mixture of diethyl ether/hexanes (300 mL) and filtered off on a Büchner funnel to provide 50.0 g (92%) of the title compound. Thin layer chromatography analysis of the title compound showed a single spot with $R_f$=0.18 (silica, 3:2 hexanes/ethyl acetate).

Example 15

Preparation of L-methionine sulfone-O-benzyl ester hydrochloride salt

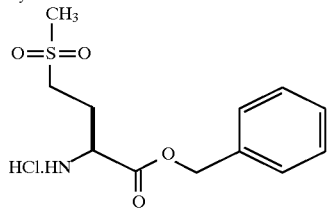

To the compound of Example 14 (50.0 g), 200 mL of a 4M solution of HCl in dioxine was added. The solid eventually dissolved over 2 hours and showed no starting material by thin layer chromatography. The solution was then reduced in volume under vacuum and the resulting solid was washed with diethyl ether to provide 55.0 g (100%) of the title compound as a white solid.

Example 16

Preparation of N-cyclohexylmethanesulfonyl-L-methionine sulfone-O-benzyl ester

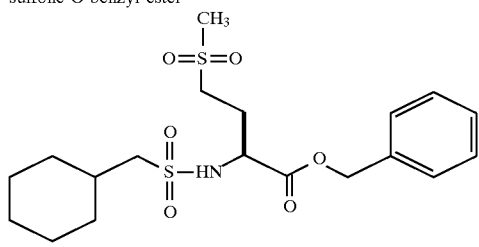

To a suspension of the compound of Example 15 (4.6 g, 15 mmole) in dry CH$_3$CN (35 mL) cooled to 0° C. in an ice bath, the compound of Example 13 (N-cyclohexylmethane sulfonyl chloride, 3.46 g, 17.6 mmole) as a solution in CH$_3$CN (10 mL) was added, followed by pyridine (3.8 mL, 45 mmole). The reaction was allowed to stir in the ice bath for 15 hours while slowly warming to room temperature. The solvent was evaporated under vacuum to give a residue.

The resulting residue was dissolved in ethyl acetate (200 mL) and the solution was washed with saturated aqueous bicarbonate (50 mL), brine (50 mL), saturated aqueous citric acid (50 mL), and dried over MgSO$_4$. The solution was filtered and evaporated under vacuum to provide 3.3 g of a yellow oil. This crude product was purified by silica gel flash chromatography to provide 1.63 g (25%) of the title compound as a clear viscous oil. Thin layer chromatography analysis of the title compound showed a single spot with R$_f$=0.29 (silica, 3:2 ethyl acetate/hexanes).

Example 17

Preparation of N-cyclohexylmethanesulfonyl-L-methionine sulfone

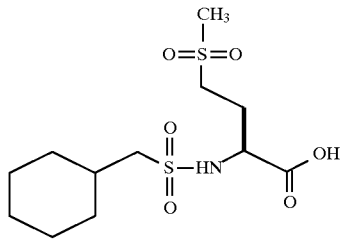

To a solution of the compound of Example 16 (1.6 g, 3.7 mmole) in CH$_3$OH (50 mL), 250 mg 10% palladium on carbon was added. This mixture was then subjected to atmospheric hydrogenation at room temperature for 12 hours. The reaction mixture was then filtered through a pad of celite and the solvent was evaporated under vacuum to provide the title compound (1.06 g, 88%) as a white solid. Thin layer chromatography analysis of the title compound showed a single spot with R$_f$=0.2 (silica, 9:1 chloroform/methanol).

Example 18

Preparation of N-cyclohexylmethanesulfonyl-L-methionine sulfone-L-proline-L-argininal

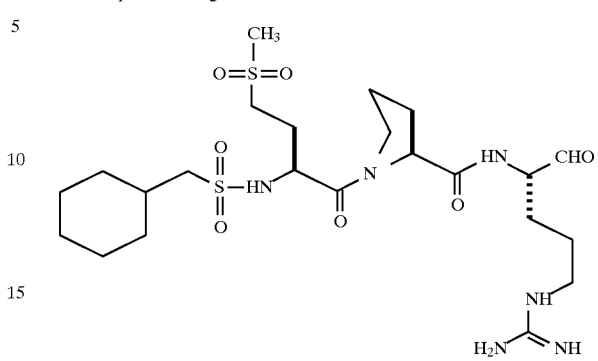

The title compound was prepared in the same manner as described in Example 8.

N-Boc-L-proline was first attached to the resin of Example 7, followed by the compound of Example 17. After cleavage of the title compound as a protected semicarbazone from the resin, the semicarbazone was hydrolyzed to give the title compound.

Fast atom bombardment mass spectrometry confirmed the theoretical molecular weight of 578.2.

Example 19

Preparation of N-(1-naphthylenesulfonyl)-L-methionine sulfone-L-proline-O-benzyl ester

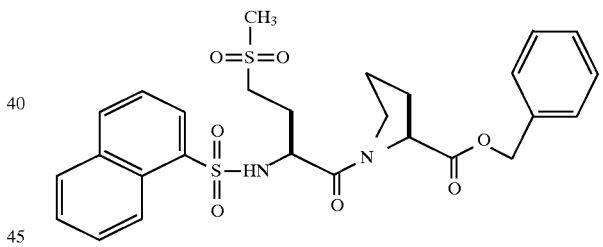

To a solution of the compound of Example 9 (3 g, 6.9 mmole) in 70 mL of dry acetonitrile, 1-naphthylenesulfonyl chloride (2.3 g, 10.3 mmole) was added followed by dry pyridine (4.1 mL, 34.4 mmole). After stirring for 16 hours at room temperature, the solvent was removed under vacuum and the resulting oil was dissolved in 500 mL ethyl acetate and washed with 100 mL each of water, 1M aqueous HCl, water, saturated aqueous sodium bicarbonate and brine. The organic phase was dried over MgSO$_4$, filtered and the solvent removed under vacuum to yield an oil.

The oil was filtered down a pad of silica (50 g), rinsing with two 500 mL portions of dichloromethane followed by three 500 mL portions of 1:9 methanol/dichloromethane. The appropriate fractions were concentrated under vacuum to provide 3.8 g (99% yield) of the title compound. Thin layer chromatography analysis of the title compound showed a single spot with Rf=0.5 (silica, 1:9 methanol/dichloromethane).

Example 20

Preparation of N-(1-naphthylenesulfonyl)-L-methionine sulfone-L-proline

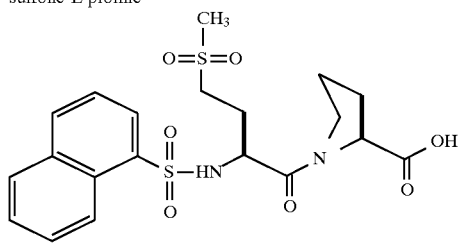

To a solution of the compound of Example 19 (3.8 g, 6.8 mmole) in 10 mL of THF and 250 mL of methanol under a nitrogen blanket, 10% palladium on carbon (2 g) was added. This mixture was hydrogenated at 1 atmosphere for 16 hours. The mixture was then filtered and concentrated under vacuum to provide 3 g (96% yield) of the title compound as a white solid. Thin layer chromatography analysis of the title compound showed a single spot with Rf=0.2 (1:9 methanol/dichloromethane).

Example 21

Preparation of N-(1-naphthylenesulfonyl)-L-methionine sulfone-L-proline-L-argininal

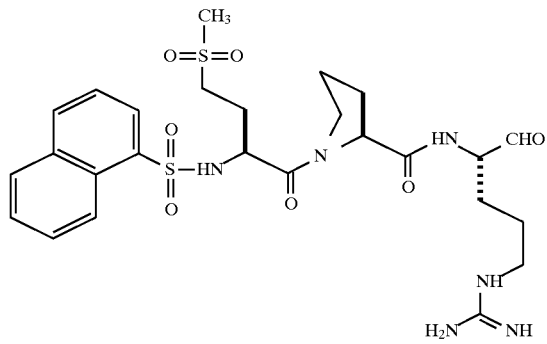

The title compound was prepared in the same manner as described in Example 8.

The compound of Example 20 was attached to the resin of Example 7. After cleavage of the title compound as a protected semicarbazone from the resin, the semicarbazone was hydrolyzed to give the title compound.

Fast atom bombardment mass spectrometry confirmed the theoretical molecular weight of 608.2.

Example 22

Preparation of N-(2-naphthylenesulfonyl)-L-methionine sulfone-L-proline-O-benzyl ester

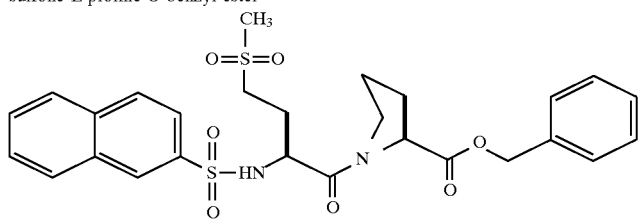

A 3 g (6.878 mmole) portion of the compound of Example 9 was added to 69 mL of acetonitrile. To this mixture, 2.34 g (10.3 mmole, 1.5 eq.) of 2-naphthylenesulfonylchloride and 4.20 g (4.12 mL, 34.4 mmole, 5 eq.) of pyridine was added and the mixture was stirred for 10 hours. The mixture was then concentrated under vacuum, diluted with ethyl acetate (500 mL) and washed with 1M HCl, water, aqueous sodium bicarbonate, and brine. The organic phase was dried over $MgSO_4$ and concentrated under vacuum. Thin layer chromatography (silica, 10% methanol in dichloromethane) showed some 2-naphthylsulfonylchloride. The mixture was then filtered down a plug of silica, eluting with dichloromethane (100 mL), then 10% methanol/dichloromethane (200 mL). Removal of the solvent under vacuum from the collected fractions gave 3.96 g of the title compound.

Example 23

Preparation of N-(2-naphthylenesulfonyl)-L-methionine sulfone-L-proline

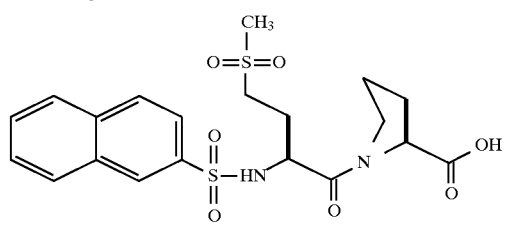

A 3.96 g (7.088 mmole) portion of the compound of Example 22 was dissolved in 250 mL of methanol with a trace of THF. To this solution, 2 g of 10% palladium on carbon was added under a nitrogen blanket. The mixture was then stirred under hydrogen at one atmosphere of pressure for 10 hours. After this time, thin layer chromatography (silica, 10% methanol in dichloromethane) showed no starting material. This solution was then filtered through a nylon filter and concentrated under vacuum to give 3.2 g (96%) of the title compound.

Example 24

Preparation of N-(2-naphthylenesulfonyl)-L-methionine sulfone-L-proline-L-argininal

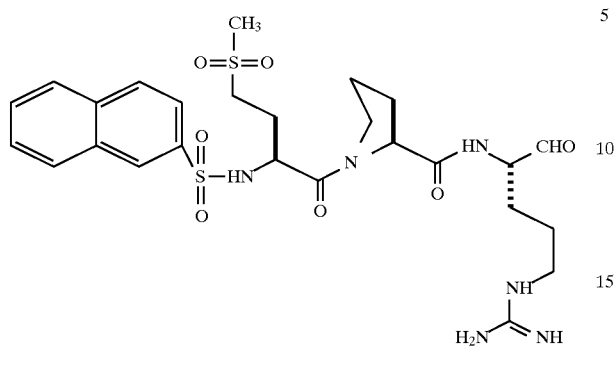

The title compound was prepared in the same manner as described in Example 8.

The compound of Example 23 was attached to the resin of Example 7. After cleavage of the title compound as a protected semicarbazone from the resin, the semicarbazone was hydrolyzed to give the title compound.

Fast atom bombardment mass spectrometry confirmed the theoretical molecular weight of 608.2.

Example 25

Preparation of N-benzylsulfonyl-L-methionine sulfone-L-proline-O-benzyl ester

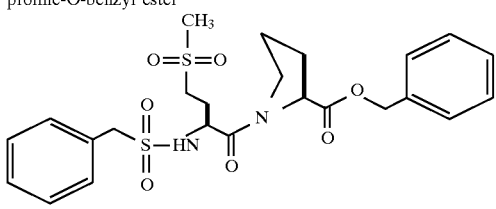

To a solution of the compound of Example 9 (20.0 mmole, 8.08 g) in dry acetonitrile (100 mL) cooled to 0° C., alpha-toluenesulfonylchloride (20.0 mmole, 3.8 g) was added all at once followed by pyridine (50.0 mmole, 4.2 mL). The mixture was then stirred in the ice bath for 12 hours eventually warming to room temperature.

The reaction mixture was reduced to a residue under vacuum. The residue was taken up ethyl acetate (300 mL) and washed with saturated aqueous sodium bicarbonate, brine, 1M aqueous HCl (100 mL), dried over MgSO$_4$, filtered and evaporated under vacuum to provide 8.8 g (100%) of the title compound as a foamy golden solid. Thin layer chromatography analysis of the title compound showed a single spot with Rf=0.31 (silica gel, 95:5 chloroform/methanol). The solid was filtered through a plug of silica gel (50 g) using ethyl acetate as eluent before hydrogenation to eliminate possible sulfur related impurities.

Example 26

Preparation of N-benzylsulfonyl-L-methionine sulfone-L-proline

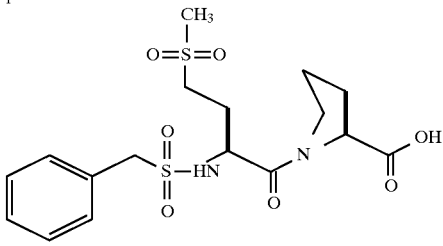

To a solution of the compound of Example 25 (8.8 g, 2 mmole) in methanol (300 mL), 1.0 g of 10% palladium on carbon was added. The mixture was then hydrogenated at 1 atmosphere of hydrogen gas and room temperature for 12 hours with stirring. The mixture was then filtered and the organic phase reduced under vacuum to provide 8.0 g (100%) of the title compound as a white foamy solid.

Example 27

Preparation of N-benzylsulfonyl-L-methionine sulfone-L-proline-L-arginal

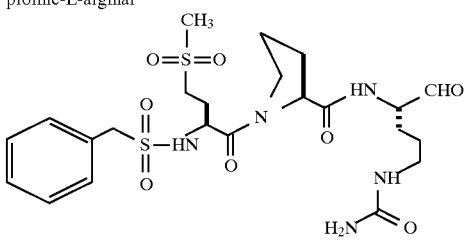

The title compound was prepared in the same manner as described in Example 8.

The compound of Example 26 was attached to the resin of Example 7. After cleavage of the title compound as a protected semicarbazone from the resin, the semicarbazone was hydrolyzed to give the title compound.

Fast atom bombardment mass spectrometry confirmed the theoretical molecular weight of 572.2.

Example 28

Preparation of N-Boc-N$^g$-nitro-argininol.

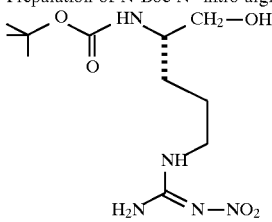

To a suspension of Boc-N$^g$-nitro-arginine (370 g, 1.15 moles) in 6 liters of dry THF at −78° C., borane.THF complex 1.0M (2.6 liters) was slowly added. The reaction temperature was controlled so that it did not exceed −60° C. After the addition was complete, the reaction was placed in a freezer at −20° C. overnight.

The following day, the greenish-yellow reaction mixture was cooled to −78° C. and slowly quenched with 3 liters of anhydrous methanol. Two hours after this quenching, the mixture was warmed to 25° C. and stirred for an additional 2 hours. The solvent is removed under vacuum to yield the title compound (360 g). This intermediate is used as is in coupling reactions and the major product had a Rf=0.28 (silica, 90:10 dichloromethane/methanol) by thin layer chromatography.

Example 29

Preparation of N-(2-propylpentanoyl)-L-methionine sulfone-L-proline-O-benzyl ester

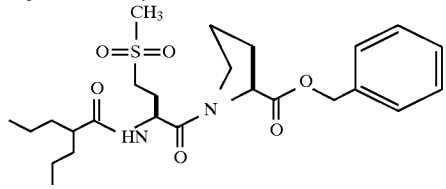

To a solution at 15° C. containing the compound of Example 9 (88.06 g, 0.178 mole), 2-propylpentanoic acid (33.45 mL, 0.2136 mole), BOP (94.5 g, 0.2136 mole) and 600 mL of dry DMF, NMM (117 mL, 1.068 mole) was slowly added. The reaction mixture was warmed slowly to 25° C. and then was stirred overnight.

On the following day, 1 liter of water was added to the reaction mixture and it was extracted 3 times with 500 mL of ethyl acetate. The organic extracts were combined and washed with 3–300 mL portions of 1.0N HCl, 3–300 mL portions of saturated sodium bicarbonate and 1–100 mL portion of brine. The organic phase was then dried over magnesium sulfate, filtered, and then the solvent was removed under vacuum to yield 84.6 g (96 %) of the title compound. Thin layer chromatography analysis of the title compound showed a single spot with Rf=0.35 (silica gel, 95:5 dichloromethane/methanol).

Example 30

Preparation of N-(2-propylpentanoyl)-L-methionine sulfone-L-proline

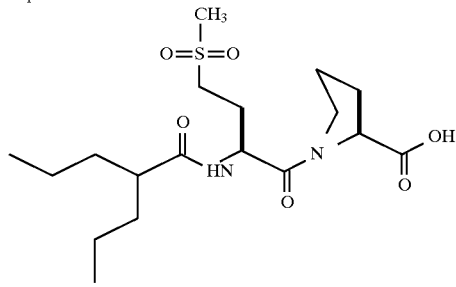

To a solution of the compound of Example 29 (37 g, 0.07495 mole) and 500 mL methanol, 3.7 g 10% palladium on carbon wet with dichloromethane was added. The mixture was hydrogenated in a Parr Hydrogenator at 25 psi for 7 hours, after which time the mixture was filtered and the solvent removed under vacuum to yield 29.71 g (98%) of the title compound as a white solid. Thin layer chromatography analysis of the title compound showed a single spot with Rf=0.15 (silica, 85:15 dichloromethane/methanol).

Example 31

Preparation of N-(2-propylpentanoyl)-L-methionine sulfone-L-proline-N$^g$-nitro-L-argininol

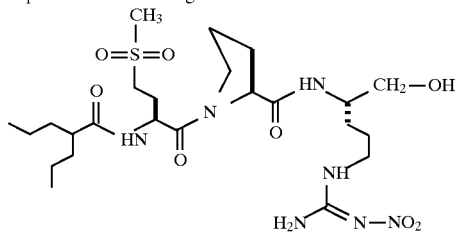

To a solution of compound of Example 28 (34 g, 0.1117 mole) in 500 mL of methanol at 0° C., 1.2 liters of saturated HCl/methanol solution was added. After 30 minutes, the ice bath was removed and the reaction mixture was allowed to stir for 2 hours. After this time, the solvent was removed under vacuum and the resulting solid was used as is without further purification.

The resulting solid was dissolved in 1 liter of acetonitrile. To this solution, the compound of Example 30 (49.56 g, 0.1225 mole) and BOP (59.11 g, 0.1337 mole) was added, followed by the slow addition of NMM (73.5 mL, 0.668 mole). The mixture was stirred overnight at room temperature. After this time, the solvent was removed under vacuum and the residue was chromatographed on silica gel eluting with a 100:0 to 90:10 gradient of dichloromethane and methanol. 40.5 g of the title compound as a white solid was isolated by evaporation of solvents from the collected fractions. Thin layer chromatography analysis of the title compound showed a single spot with Rf=0.38 (silica gel, 95:5 dichloromethane/methanol).

Example 32

Preparation of N-(2-propylpentanoyl)-L-methionine sulfone-L-proline-L-argininol

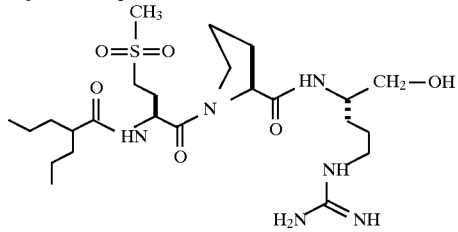

To a solution of the compound of Example 31 (6 g, 0.0101 mole), 3 mL of acetic acid and 100 mL methanol, 0.6 g 10% palladium on carbon wet with dichloromethane was added. This mixture was hydrogenated in a Parr Hydrogenator at 45 psi for 16 hours. After this time, the mixture was filtered and the organic phase was removed under vacuum to yield 4.7 g (77%) of the title compound as a glass. Thin layer chromatography analysis of the title compound showed a single spot with Rf=0.17 (silica gel, 85:15 dichloromethane/methanol).

Example 33

Preparation of N-(2-propylpentanoyl)-L-methionine sulfone-L-proline-L-argininal

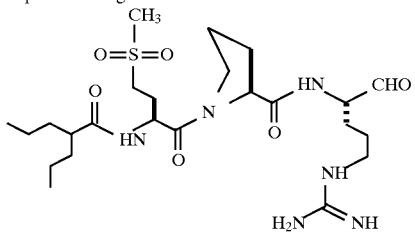

To a solution of the compound of Example 32 (5.4 g, 9.9 mmole), dichloroacetic acid (4.07 mL, 49.5 mmole), 75 mL of dimethyl sulfoxide and 75 mL of toluene at 0° C., EDC (18.93 g, 99 mmole) was added slowly. The ice bath was removed after 5 minutes and the reaction was allowed to warm to room temperature for 1.5 hours. After this time, the toluene was removed under vacuum and the resulting solution was diluted with 750 mL of HPLC-grade water and filtered. This solution was then chromatographed using a C-18 reverse phase column using a 30 minute gradient comprising 100:0 to 60:40 of HPLC-grade water/acetonitrile containing 0.1% trifluoroacetic acid. The fractions were combined and lyophilyzed to give 4.47 g (83.5%) of the title compound.

Fast atom bombardment mass spectrometry confirmed the theoretical molecular weight of 544.3.

Example 34

Preparation of S-methyl-L-cysteine

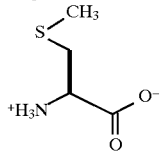

A 1.49 liter aqueous solution of commercially available (Aldrich) L-cysteine hydrochloride monohydrate (50.0 g, 284.5 mmole) and barium hydroxide octahydrate (94.24 g, 298.7 mmole), at room temperature, was treated with dimethyl sulfate (37.32 g, 295.9 mmole) added dropwise over 40 minutes. After stirring an additional 2 hours, concentrated sulfuric acid (29.27 g, 298.7 mmole) dissolved in 100 mL of de-ionized water was added in portions. The slurry was filtered and the filtrate concentrated to 70 mL under vacuum at 40° C. The solution was adjusted to pH 5–6 (pH papers) with concentrated ammonium hydroxide causing a precipitate to form. The slurry (140 mL aqueous volume) was diluted with 240 mL of ethanol, stirred and cooled at 3° C. The white solid was filtered, washed with cold 2:1 ethanol/water (50 mL) and dried under high vacuum at room temperature to give 33.3 g (86.6% yield) of the title compound.

Example 35

Preparation of N-Boc-S-methyl-L-cysteine

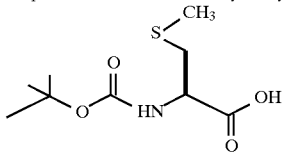

The compound of Example 34 (15.0 g, 110 mmole) was suspended in 130 mL of saturated sodium bicarbonate (approximately 1.1M). A solution of di-t-butyl dicarbonate (26.4 g, 121 mmole) in 60 mL of THF was added and vigorously stirred for 18 hours at room temperature.

The reaction mixture was extracted with diethyl ether (100 mL). The resulting aqueous phase was layered with ethyl acetate (200 mL) and acidified to pH 2 (pH papers) with 1N hydrochloric. The aqueous layer was further extracted with ethyl acetate (3×200 mL). The organic extracts were combined, washed with brine, dried with MgSO$_4$ and the solvent evaporated under vacuum to yield 21.2 mg of the title compound as a clear oil (81.9% crude yield). Thin layer chromatography analysis of the title compound showed a single spot with Rf=0.5 (silica; 90:10:2 dichloromethane/methanol/acetic acid).

Example 36

Preparation of N-Boc-S-methyl-L-cysteine-L-proline-O-benzyl ester

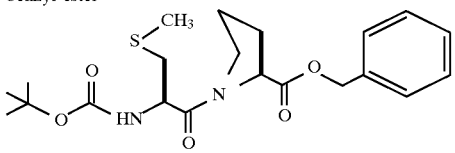

The compound of Example 35 (14.64 g, 62.2 mmole) and L-proline-O-benzyl ester hydrochloride (15.04 g, 62.2 mmole) were suspended in 135 mL of acetonitrile at 0° C., then BOP (27.51 g, 62.2 mmole) and NMM (18.9 g, 186.6 mmole) were added. The ice bath was removed after 30 minutes and the reaction was stirred for 18 hours at room temperature.

The reaction mixture solvent was evaporated at 25° C. under vacuum to give an oil which was dissolved in ethyl acetate (250 mL). This solution was successively washed with 1N hydrochloric acid (1×50 mL), saturated sodium bicarbonate (1×50 mL) and brine (1×50 mL), dried with MgSO$_4$. The solution was evaporated under vacuum to give crude product.

The crude product was purified by column chromatography on silica gel, eluting with 1:1 hexane/ethyl acetate. 21.9 g (83.3% yield) of the title compound was isolated as an amorphous solid by evaporating the solvent under vacuum from the column fractions. Thin layer chromatography analysis of the title compound showed a single spot with Rf=0.53 (silica, 3:2 ethyl acetate/hexane).

Example 37

Preparation of N-Boc-S-methyl-L-cysteine sulfone-L-proline-O-benzyl ester

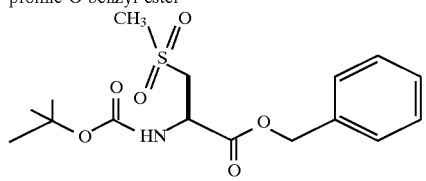

The compound of Example 36 (16.13 g, 38.18 mmole) was dissolved in 200 mL of glacial acetic acid and sodium perborate tetrahydrate (29.37 g, 190.9 mmole) was added and the mixture heated to 55° C. After 2.5 hours at this temperature, the reaction solution was diluted with 800 mL of brine, the aqueous layer was extracted with ethyl acetate (3×250 mL) and the combined organic extracts were dried with MgSO$_4$. This solution was filtered, evaporated under vacuum to yield a residue that was repeatedly azeotroped with toluene (200 mL) under vacuum to remove acetic acid. The residual slurry was suspended in ethyl acetate (200 mL), filtered and the solvent evaporated under vacuum to yield 17.4 g (100% yield) of the title compound as a white solid. Thin layer chromatography analysis of the title compound showed a single spot with Rf=0.25 (3:2 ethyl acetate/hexane).

Example 38

Preparation of N-(1-butanesulfonyl)-S-methyl-L-cysteine sulfone-L-proline-O-benzyl ester

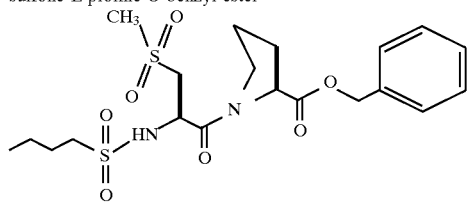

The compound of Example 37 (2.0 g, 4.4 mmole) was dissolved in 12 mL of 4N anhydrous hydrochloric acid/dioxane and was stirred for several hours at room temperature until all starting material was consumed. The hydrochloric acid/dioxane solution was then evaporated under vacuum to yield an oil. This oil was dissolved in acetonitrile and evaporated under vacuum. This was done three times.

The oil was suspended in 17 mL of acetonitrile, cooled to ice bath temperature, then 1-butanesulfonyl chloride (0.69 g, 4.4 mmole) and pyridine (1.04 g, 13.2 mmole) were added. The reaction was taken from the ice bath after 30 minutes and stirred at room temperature for 18 hours. The reaction mixture was evaporated under vacuum to give an oil. The oil was taken up in 200 mL ethyl acetate, and was washed successively with 1N hydrochloric acid (1×50 mL) saturated sodium bicarbonate 1×50 mL) and brine (1×50 mL). After drying with MgSO$_4$, the solvent was evaporated under vacuum to give crude product.

This crude product was purified by column chromatography silica gel eluting with 1:99; methanol/dichloromethane). Removal of the solvent from the column fractions yielded 1.25 g (59.8% yield) of the title compound as a solid. Thin layer chromatography analysis of the title compound showed a single spot with Rf=0.59 (silica; 95:5 dichloromethane/methanol).

Example 39

Preparation of N-(1-butanesulfonyl)-S-methyl-L-cysteine sulfone-L-proline

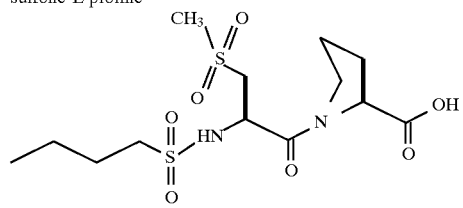

The compound of Example 38 (1.55 g, 2.45 mmole) was dissolved in THF (50 mL), 0.5 g of 10% palladium on carbon was added and the mixture was stirred under hydrogen gas at atmospheric pressure for 18 hours.

After the catalyst was filtered off the reaction mixture, the solvent was removed under vacuum and the resulting oil was taken up in a solution of saturated sodium bicarbonate. This solution was then extracted with ethyl acetate (1×150 mL) and the organic layer was decanted off. The remaining aqueous layer was layered with 100 mL of ethyl acetate and acidified with 1N hydrochloric acid to pH 2 (pH papers). After the phases separated, the organic layer was saved and the aqueous layer was then further extracted with ethyl acetate (3×100 mL).

The organic extracts were combined and washed with brine, dried with MgSO$_4$, filtered and evaporated under vacuum to give 0.77 g (yield 82.9%) of the title compound as a foamy solid. Thin layer chromatography analysis of the title compound showed a single spot with Rf=0.3 (silica; 90:10:2 dichloromethane/methanol/acetic acid).

Example 40

Preparation of N-(1-butanesulfonyl)-S-methyl-L-cysteine sulfone-L-proline-L-argininal

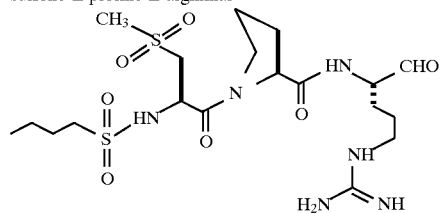

The title compound was prepared in the same manner as described in Example 8.

The compound of Example 39 was attached to the resin of Example 7. After cleavage of the title compound as a protected semicarbazone from the resin, the semicarbazone was hydrolyzed to give the title compound. 0.1 mL of thiocresol was additionally added to the anisole-HF cleavage mixture.

Fast atom bombardment mass spectrometry confirmed the theoretical molecular weight of 524.2.

Example 41

Preparation of N-(2-propylpentanoyl)-S-methyl-L-cysteine sulfone-L-proline-O-benzyl ester

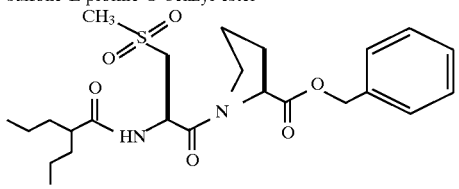

The compound of Example 37 (3.0 g, 4.66 mmole) was dissolved in 12 mL of 4N anhydrous hydrochloric acid/dioxane. The solution was stirred for several hours at room temperature until all starting material was consumed. The hydrochloric acid/dioxane solution was evaporated under vacuum. This oil was dissolved in acetonitrile and evaporated under vacuum. This was done three times.

The oil was suspended in 25 mL of acetonitrile, cooled to ice bath temperature, then 2-propylpentanoic acid (0.95 g, 6.6 mmole), BOP (2.92 g, 6.6 mmole) and NMM (2.0 g, 19,8 mmole) were added. The reaction was taken from the ice bath after 30 minutes and stirred at room temperature for 18 hours. The acetonitrile was evaporated under vacuum and the oil was taken up in ethyl acetate (200 mL) and washed successively with 1N hydrochloric acid (1×50 mL), saturated sodium bicarbonate (1×50 mL) and brine (1×50 mL). After drying with $MgSO_4$, the ethyl acetate was evaporated under vacuum to yield crude product.

The crude product was purified by column chromatography on silica gel, eluting with 1.5;98.5, methanol/dichloromethane). The solvent from the column fractions was evaporated under vacuum to yield 2.0 g (63.0% yield) of the title compound as an oil. Thin layer chromatography analysis of the title compound showed a single spot with Rf=0.43 (silica; 95:5:1 dichloromethane/methanol/acetic acid).

Example 42

Preparation of N-(2-propylpentanoyl)-S-methyl-L-cysteine sulfone-L-proline

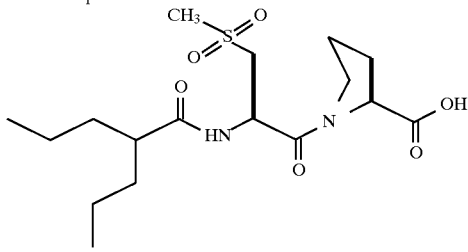

The compound of Example 41 (1.75 g, 3.64 mmole) was dissolved in THF (50 mL), 0.5 g of 10% palladium on carbon was added and the mixture was stirred under hydrogen gas at atmospheric pressure for 18 hours.

After the catalyst was filtered off the reaction mixture, the solvent was removed under vacuum and the resulting oil was taken up in a solution of saturated sodium bicarbonate. This solution was then extracted with ethyl acetate (1×150 mL) and the organic layer was decanted off. The remaining aqueous layer was layered with 100 mL of ethyl acetate and acidified with 1N hydrochloric acid to pH 2 (pH papers). After the phases separated, the organic layer was saved and the aqueous layer was then further extracted with ethyl acetate (3×100 mL).

The organic extracts were combined and washed with brine, dried with $MgSO_4$, filtered and evaporated under vacuum to give 0.90 g (63.1% yield) of the title compound as a foamy solid. Thin layer chromatography analysis of the title compound showed a single spot with Rf 0.3 (silica, 90:10:2 dichloromethane/methanol/acetic acid).

Example 43

Preparation of N-(2-propylpentanoyl)-S-methyl-L-cysteine sulfone-L-proline-L-argininal

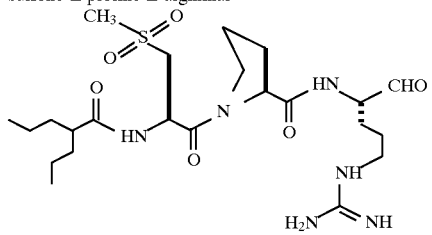

The title compound was prepared in the same manner as described in Example 8.

The compound of Example 42 was attached to the resin of Example 7. After cleavage of the title compound as a protected semicarbazone from the resin, the semicarbazone was hydrolyzed to give the title compound. 0.1 mL of thiocresol was additionally added to the anisole-HF cleavage mixture.

Fast atom bombardment mass spectrometry confirmed the theoretical molecular weight of 530.3.

Example 44

Preparation of N-(2-naphthalenesulfonyl)-S-methyl-L-cysteine sulfone-L-proline-O-benzyl ester

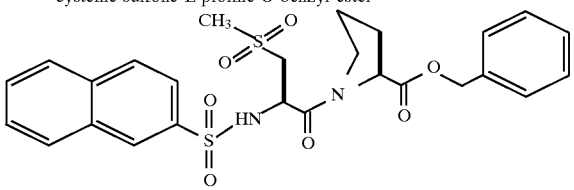

The compound of Example 37 (3.0 g, 6.6 mmole) was dissolved in 12 mL of 4N anhydrous hydrochloric acid/dioxane. The solution was stirred for several hours at room temperature until all starting material was consumed. The hydrochloric acid/dioxane solution was evaporated under vacuum. The resulting oil was dissolved in acetonitrile and evaporated under vacuum. This was done three times.

The remaining oil was suspended in 20 mL of acetonitrile, cooled to ice bath temperature, then 2-naphthalenesulfonyl chloride (0.1.49 g, 6.6 mmole) and pyridine (1.57 g, 19.8 mmole) were added. The reaction was taken from the ice bath after 30 minutes and stirred at room temperature for 18 hours. The reaction mixture was reduced in volume under vacuum to an oil. The oil was taken up in 200 mL ethyl acetate and washed successively with 1N hydrochloric acid (1×50 mL), saturated sodium bicarbonate 1×50 mL) and brine (1×50 mL). After drying with $MgSO_4$, the ethyl acetate was evaporated under vacuum to give crude product.

The crude product was purified by column chromatography on silica gel, eluting with 0.8:99.2 methanol/dichloromethane to yield 2.2 g (60.6% yield) of the title compound as a solid. Thin layer chromatography analysis of

Example 45

Preparation of N-(2-naphthalenesulfonyl)-S-methyl-L-cysteine sulfone-L-proline

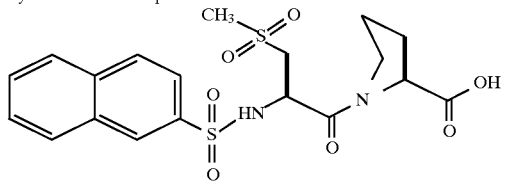

The compound of Example 44 (1.95 g, 3.58 mmole) was dissolved in THF (50 mL), 0.5 g of 10% palladium on carbon was added and the mixture was stirred under hydrogen gas at atmospheric pressure for 18 hours.

After the catalyst was filtered off the reaction mixture, the solvent was removed under vacuum and the resulting oil was taken up in a solution of saturated sodium bicarbonate. This solution was then extracted with ethyl acetate (1×150 mL) and the organic layer was decanted off. The remaining aqueous layer was layered with 100 mL of ethyl acetate and acidified with 1N hydrochloric acid to pH 2 (pH papers). After the phases separated, the organic layer was saved and the aqueous layer was then further extracted with ethyl acetate (3×100 mL).

The organic extracts were combined and washed with brine, dried with MgSO$_4$, filtered and evaporated under vacuum to give 0.95 g of a solid (yield 58.3%). Thin layer chromatography of the isolated material was performed, Rf 0.3 (silica, 90:10:2 dichloromethane/methanol/acetic acid).

Example 46

Preparation of N-(2-naphthalenesulfonyl)-S-methyl-L-cysteine sulfone-L-proline-L-argininal

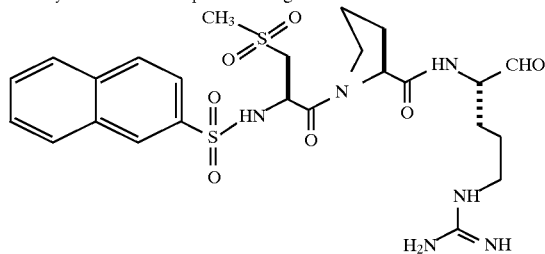

The title compound was prepared in the same manner as described in Example 8.

The compound of Example 45 was attached to the resin of Example 7. After cleavage of the title compound as a protected semicarbazone from the resin, the semicarbazone was hydrolyzed to give the title compound.

Fast atom bombardment mass spectrometry confirmed the theoretical molecular weight of 594.2.

Example 47

Preparation of N-(1-naphthalenesulfonyl)-S-methyl-L-cysteine sulfone-L-proline-O-benzyl ester

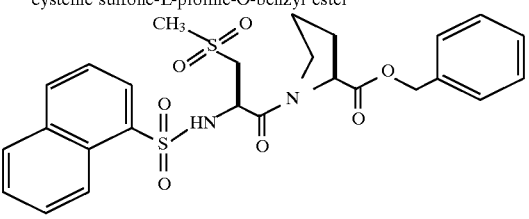

The compound of Example 37 (3.0 g, 6.6 mmole) was dissolved in 12 mL of 4N anhydrous hydrochloric acid/dioxane. The solution was stirred for several hours at room temperature until all starting material was consumed. The hydrochloric acid/dioxane solution was evaporated under vacuum to give an oil. The oil was dissolved in acetonitrile and evaporated under vacuum. This was done three times.

The remaining oil was suspended in 20 mL of acetonitrile, cooled to ice bath temperature, then 1-naphthalenesulfonyl chloride (0.1.49 g, 6.6 mmole) and pyridine (1.57 g, 19.8 mmole) were added. The reaction was taken from the ice bath after 30 minutes and stirred at room temperature for 18 hours. The reaction mixture was reduced in volume under vacuum to an oil. The oil was taken up in 200 mL ethyl acetate and washed successively with 1N hydrochloric acid (1×50 mL), saturated sodium bicarbonate 1×50 mL) and brine (1×50 mL). After drying with MgSO$_4$, the solvent was evaporated under vacuum to give crude product.

The crude product was purified by column chromatography on silica gel, eluting with 0.8:99.2 methanol/dichloromethane to yield 1.61 g (45% yield) of the title compound as a solid. Thin layer chromatography analysis of the title compound showed a single spot with Rf=0.50 (silica; 90:10:2 dichloromethane/methanol/acetic acid).

Example 48

Preparation of N-(1-naphthalenesulfonyl)-S-methyl-L-cysteine sulfone-L-proline

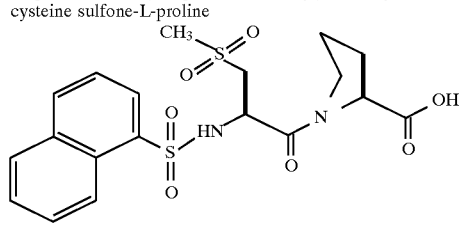

The compound of Example 47 (1.6 g, 2.94 mmole) was dissolved in THF (50 mL), 0.5 g of 10% palladium on carbon was added and the mixture was stirred under hydrogen gas at atmospheric pressure for 18 hours.

After the catalyst was filtered off the reaction mixture, the solvent was removed under vacuum and the resulting oil was taken up in a solution of saturated sodium bicarbonate. This solution was then extracted with ethyl acetate (1×150 mL) and the organic layer was decanted off. The remaining aqueous layer was layered with 100 mL of ethyl acetate and acidified with 1N hydrochloric acid to pH 2 (pH papers). After the phases separated, the organic layer was saved and the aqueous layer was then further extracted with ethyl acetate (3×100 mL).

The organic extracts were combined and washed with brine, dried with MgSO$_4$, filtered and evaporated under vacuum to give 1.07 g (80% yield) of the title compound. Thin layer chromatography analysis of the title compound showed a single spot with Rf=0.3 (silica; 90:10:2 dichloromethane/methanol/acetic acid).

Example 49

Preparation of N-(1-naphthalenesulfonyl)-S-methyl-L-cysteine sulfone-L-proline-L-argininal

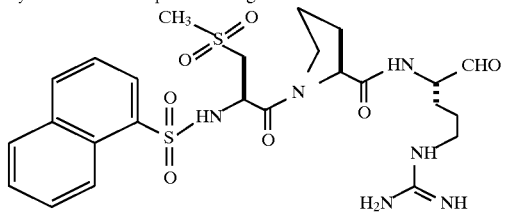

The title compound was prepared in the same manner as described in Example 8.

The compound of Example 48 [N-(1-naphthalenesulfonyl)-S-methyl-L-cysteine sulfone-L-proline] was attached to the resin of Example 7. After cleavage of the title compound as a protected semicarbazone from the resin, the semicarbazone was hydrolyzed to give the title compound. 0.1 mL of thiocresol was additionally added to the anisole-HF cleavage mixture.

Fast atom bombardment mass spectrometry confirmed the theoretical molecular weight of 594.2.

Example 50

Preparation of S-(t-butyl acetate)-L-cysteine

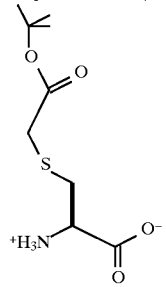

A 360 mL aqueous solution of commercially available (Aldrich) L-cysteine hydrochloride monohydrate (60.0 g, 341.7 mmole) and sodium hydroxide (27.33 g, 683.4 mmole), at room temperature, was treated with a solution of t-butyl bromoacetate (72.3 g, 370.6 mmole) in 130 mL of dioxane over 30 minutes. The reaction was stirred for 18 hours, during which time a thick precipitate formed. The solid was filtered off, washed with diethyl ether (100 mL) and dried under high vacuum at 40° C. to give 82.5 g (103.8% crude yield includes occluded inorganic salt) of the title compound.

Example 51

Preparation of N—Boc—S-(t-butyl acetate)-L-cysteine

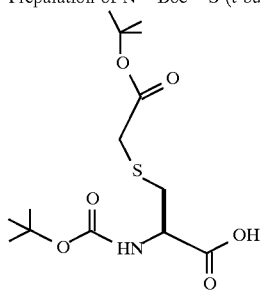

The compound of Example 50 (82.5 g, 341.7 mmole) and sodium bicarbonate (33.96 g, 404 mmole) were suspended in 600 mL of deionized water. A solution of di-t-butyl dicarbonate (80.88 g, 370 mmole) in 350 mL of dioxane was added and the slurry was stirred for 18 hours.

The slurry was extracted with diethyl ether (2×100 mL). The slurry was layered with ethyl acetate (200 mL) and acidified with 1N hydrochloric acid to pH 2 (pH papers). The resulting organic layer was saved and the remaining aqueous layer was further extracted with ethyl acetate (2×200 mL). The organic extracts were combined, washed with brine, dried with MgSO$_4$ and the solvent evaporated under vacuum to yield 84.3 g (74.6% yield) of the title compound as a clear oil. Thin layer chromatography analysis of the title compound showed a single spot with Rf=0.55, (silica; 90:10:2 dichloromethane/methanol/acetic acid).

Example 52

Preparation of N—Boc—S-(t-butyl acetate)-L-cysteine-L-proline-O-benzyl ester

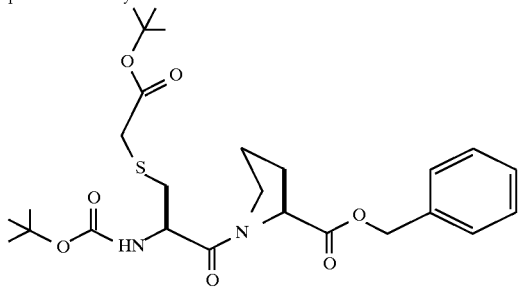

The compound of Example 51 (31.89 g, 95.06 mmole) and L-proline-O-benzyl ester hydrochloride (22.98 g, 95.06 mmole) were suspended in 140 mL of acetonitrile and 120 mL of DMF at 0° C., then BOP (42.0 g, 95.06 mmole) and NMM (28.84 g, 285.18 mmole) were added. The ice bath was removed after 30 minutes and the reaction was stirred for 18 hours at room temperature. The reaction mixture was reduced in volume under vacuum at 25° C. to give an oil. The oil was dissolved in ethyl acetate (250 mL), then successively washed with 1N hydrochloric acid (1×50 mL), saturated sodium bicarbonate (1×50 mL) and brine (1×50 mL). The organic layer was dried with MgSO$_4$ and evaporated under vacuum to give crude product.

The crude product was purified by column chromatography on silica gel, eluting with 55:45 hexane/ethyl acetate to yield 27.91 g (57.9% yield) of the title compound as an oil. Thin layer chromatography analysis of the title compound showed a single spot with Rf=0.65 (silica, 3:2 ethyl acetate/hexane).

Example 53

Preparation of N—Boc—S-(t-butyl acetate)-L-cysteine sulfone-L-proline-O-benzyl ester

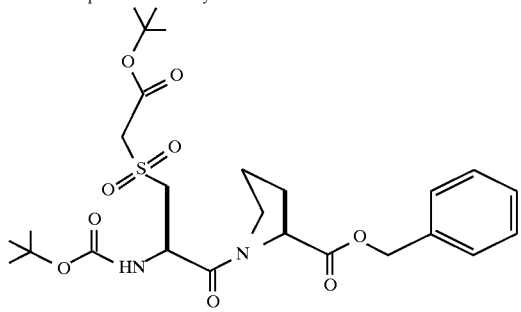

The compound of Example 52 (27.9 g, 55.07 mmole) was dissolved in 300 mL of glacial acetic acid, sodium perborate tetrahydrate (42.36 g, 275.35 mmole) was added and the mixture was heated to 55° C. After 2.5 hours at this temperature, the reaction mixture was diluted with 1 liter of brine, the aqueous layer was extracted with ethyl acetate (4×250 mL) and the combined organic extracts were dried with MgSO$_4$. This solution was filtered and evaporated under vacuum, then repeatedly azeotroped with toluene (200 mL) under vacuum to remove acetic acid. The residual slurry was dissolved in ethyl acetate (200 mL), filtered and the filtrate evaporated to yield 29.7 g (100% yield) of the title compound as a white solid. Thin layer chromatography analysis of the title compound showed a single spot with Rf=0.60 (silica, 3:2 ethyl acetate/hexane).

Example 54

Preparation of N-benzylsulfonyl-S-(t-butyl acetate)-L-cysteine sulfone-L-proline-O-benzyl ester

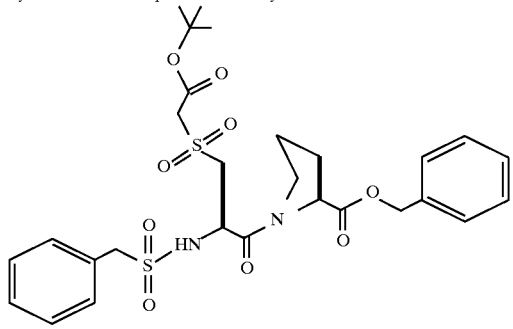

A solution of the compound of Example 53 (5.0 g, 9.28 mmole) in 105 mL of sieve-dried ethyl acetate was prepared. To this, 26 mL of 5.7N anhydrous hydrochloric acid/ethyl acetate (that had been generated in situ from acetyl chloride and methanol) was added. This mixture was stirred for several hours at room temperature until all starting material was consumed. The mixture was evaporated under vacuum and the resulting oil was dissolved in acetonitrile and then evaporated under vacuum. This was done three times.

The remaining oil was suspended in 35 mL of acetonitrile, cooled to ice bath temperature, then benzylsulfonyl chloride (2.12 g, 11.14 mmole) and pyridine (2.93 g, 37.12 mmole) were added. The reaction was removed from the ice bath after 30 minutes and allowed stirred at room temperature for 18 hours. The reaction mixture was reduced in volume under vacuum to an oil. The oil was taken up in 200 mL ethyl acetate and washed successively with 1N hydrochloric acid (1×50 mL), saturated sodium bicarbonate (1×50 mL) and brine (1×50 mL). After drying with MgSO$_4$, the organic layer was evaporated under vacuum to give crude product.

The crude product was purified by column chromatography on silica gel, eluting with 3:2 hexane/ethyl acetate to yield 2.85 g (51.8% yield) of the title compound as a solid. Thin layer chromatography analysis of the title compound showed a single spot with Rf=0.30 (silica, 3:2 ethyl acetate/hexane).

Example 55

Preparation of N-benzylsulfonyl-S-(t-butyl acetate)-L-cysteine sulfone-L-proline

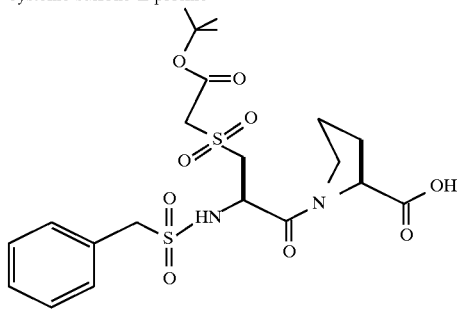

The compound of Example 54 (3.85 g, 4.81 mmole) was dissolved in THF (50 mL), 0.5 g of 10% palladium on carbon was added and the mixture was stirred under hydrogen gas at atmospheric pressure for 18 hours.

After the catalyst was filtered off the reaction mixture, the solvent was removed under vacuum and the resulting oil was taken up in a solution of saturated sodium bicarbonate. This solution was then extracted with ethyl acetate (1×150 mL) and the organic layer was decanted off. The remaining aqueous layer was layered with 100 mL of ethyl acetate and acidified with 1N hydrochloric acid to pH 2 (pH papers). After the phases separated, the organic layer was saved and the aqueous layer was then further extracted with ethyl acetate (3×100 mL).

The organic extracts were combined and washed with brine, dried with MgSO$_4$, filtered and evaporated under vacuum to give 2.1 g (yield 86.9%) of the title compound as a foamy solid. Thin layer chromatography analysis of the title compound showed a single spot with Rf=0.35 (silica, 90:10:2 dichloromethane/methanol/acetic acid).

Example 56

Preparation of N-benzylsulfonyl-S-(carboxymethyl)-L-cysteine sulfone-L-proline-L-argininal

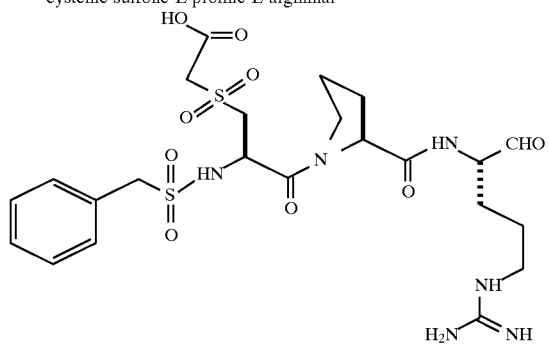

The title compound was prepared in the same manner as described in Example 8.

The compound of Example 55 was attached to the resin of Example 7. After cleavage of the title compound as a protected semicarbazone from the resin, the semicarbazone was hydrolyzed to give the title compound.

Fast atom bombardment mass spectrometry confirmed the theoretical molecular weight of 602.

Example 57

Preparation of N-(2-propylpentanoyl)-S-(t-butyl acetate)-L-cysteine sulfone-L-proline-O-benzyl ester

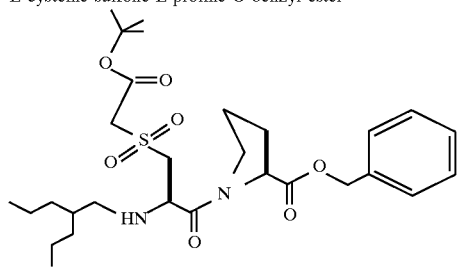

A solution of the compound of Example 53 (5.0 g, 9.28 mmole) in 105 mL of sieve-dried ethyl acetate was prepared. To this, 26 mL of 5.7N anhydrous hydrochloric acid/ethyl acetate (that had been generated in situ from acetyl chloride and methanol) was added. This mixture was stirred for several hours at room temperature until all starting material was consumed. The mixture was evaporated under vacuum and the resulting oil was dissolved in acetonitrile and then evaporated under vacuum. This was done three times.

The remaining oil was suspended in 35 mL of acetonitrile, cooled to ice bath temperature, then 2-propylpentanoic acid (1.60 g, 11.4 mmole), BOP (4.10 g, 9.28 mmole) and NMM (3.75 g, 37.1 mmole) were added. The reaction was removed from the ice bath after 30 minutes and allowed stirred at room temperature for 18 hours. The reaction mixture was reduced in volume under vacuum to an oil. The oil was taken us in 200 mL ethyl acetate and washed successively with 1N hydrochloric acid (1×50 mL), saturated sodium bicarbonate (1×50 mL) and brine (1×50 mL). After drying with MgSO$_4$, the organic layer was evaporated under vacuum to give crude product.

The crude product was purified by column chromatography on silica gel, eluting with 3:2 hexane/ethyl acetate to yield 1.81 g (34.5% yield) of the title compound as a solid. Thin layer chromatography analysis of the title compound showed a single spot with Rf=0.50 (silica, 3:2 ethyl acetate/hexane).

Example 58

Preparation of N-(2-propylpentanoyl)-S-(t-butyl acetate)-L-cysteine sulfone-L-proline

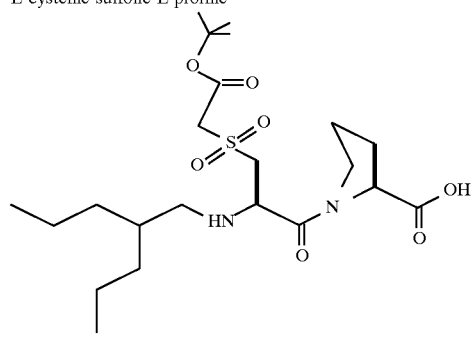

The compound of Example 57 (1.81 g, 3.2 mmole) was dissolved in THF (50 mL), 0.5 g of 10% palladium on carbon was added and the mixture was stirred under hydrogen gas at atmospheric pressure for 18 hours.

After the catalyst was filtered off the reaction mixture, the solvent was removed under vacuum and the resulting oil was taken up in a solution of saturated sodium bicarbonate. This solution was then extracted with ethyl acetate (1×150 mL) and the organic layer was decanted off. The remaining aqueous layer was layered with 100 mL of ethyl acetate and acidified with 1N hydrochloric acid to pH 2 (pH papers). After the phases separated, the organic layer was saved and the aqueous layer was then further extracted with ethyl acetate (3×100 mL).

The organic extracts were combined and washed with brine, dried with MgSO$_4$, filtered and evaporated under vacuum to give 1.30 g (yield 85.6%) of the title compound as a foamy solid. Thin layer chromatography analysis of the title compound showed a single spot with Rf=0.35 (silica, 90:10:2 dichloromethane/methanol/acetic acid).

Example 59

Preparation of N-(2-propylpentanoyl)-S-(carboxymethyl)-L-cysteine sulfone-L-proline-L-argininal

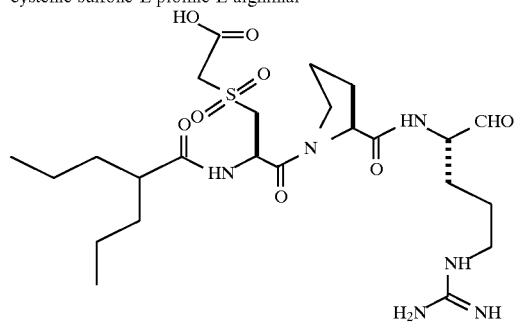

The title compound was prepared in the same manner as described in Example 8.

The compound of Example 58 was attached to the resin of Example 7. After cleavage of the title compound as a protected semicarbazone from the resin, the semicarbazone was hydrolyzed to give the title compound.

Fast atom bombardment mass spectrometry confirmed the theoretical molecular weight of 574.

Example 60

Preparation of S-(methyl acetate)-L-cysteine

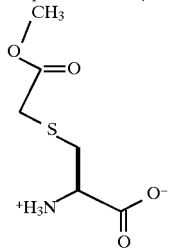

A 70 mL aqueous solution of commercially available (Aldrich) L-cysteine hydrochloride monohydrate (25.0 g, 140 mmole) and sodium hydroxide (11.2 g, 280 mmole) at room temperature was treated with a solution of methyl bromoacetate (25.7 g, 168 mmole) in 70 mL of dioxane over 30 minutes. After stirring for 18 hours, the solution was extracted with diethyl ether (2×50 mL) and evaporated under vacuum at 35° C. to give the title compound as a solid. This was used in the next reaction without further purification.

Example 61

Preparation of N—Boc—S-(methyl acetate)-L-cysteine

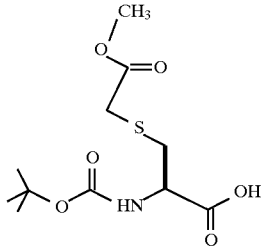

The compound of Example 60 (27.0 g, 140 mmole) was suspended in 155 mL of saturated sodium bicarbonate (approximately 1.1M). A solution of di-t-butyl dicarbonate (35.15 g, 161 mmole) in 75 mL of THF was added and the mixture was vigorously stirred for 18 hours at room temperature.

The reaction mixture was extracted with diethyl ether (100 mL) and the organic phase decanted off. The aqueous phase was then layered with ethyl acetate (200 mL) and was acidified to pH 2 (pH papers) with 1N hydrochloric acid. After the layers were separated, the organic layer was saved and the aqueous layer was extracted with ethyl acetate (3×100 mL). The organic extracts were combined and washed with brine, dried with MgSO4 and the solvent was evaporated under vacuum to yield 20.66 g (50% crude yield) of the title compound as a clear oil. Thin layer chromatography analysis of the title compound showed a single spot with Rf=0.5 (silica, 90:10:2 dichloromethane/methanol/acetic acid).

Example 62

Preparation of N—Boc—S-(methyl acetate)-L-cysteine-L-proline-O-benzyl ester

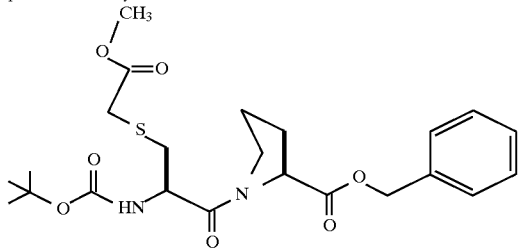

The compound of Example 61 (20.69 g, 70.5 mmole) and L-proline-O-benzyl ester hydrochloride (16.92 g, 70.5 mmole) were suspended in 140 mL of acetonitrile at 0° C., then BOP (30.96 g, 70.5 mmole) and NMM (21.2 g, 211 mmole) were added. The ice bath was removed after 30 minutes and the reaction was stirred for 18 hours at room temperature. The reaction mixture was reduced in volume at 25° C. under vacuum to give an oil. The oil was dissolved in ethyl acetate (250 mL), then successively washed with 1N hydrochloric acid (1×50 mL), saturated sodium bicarbonate (1×50 mL) and brine (1×50 mL). The organic layer was dried with MgSO4 and evaporated under vacuum to give crude product.

This crude product was purified by column chromatography on silica gel, eluting with 99:1 dichloromethane/methanol to yield 15.6 g (46.0% yield) of the title compound as an oil. Thin layer chromatography analysis of the title compound showed a single spot with Rf=0.50 (silica, 95:5 dichloromethane/methanol).

Example 63

Preparation of N—Boc—S-(methyl acetate)-L-cysteine sulfone-L-proline-O-benzyl ester

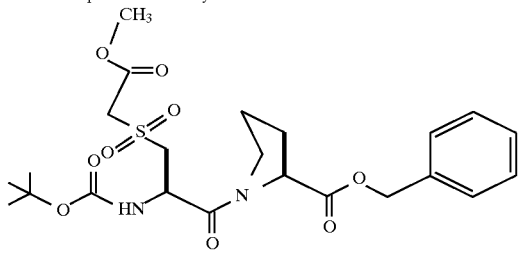

The compound of Example 62 (15.16 g, 31.55 mmole) was dissolved in 165 mL of glacial acetic acid, sodium perborate tetrahydrate (24.27 g, 157.75 mmole) was added and the mixture was heated to 55° C. After 2.5 hours at this temperature, the reaction solution was diluted with 700 mL of brine, the aqueous layer was extracted with ethyl acetate (3×250 mL) and the combined organic phases were dried with MgSO4. This solution was filtered and evaporated under vacuum, then repeatedly azeotroped with toluene (200 mL) under vacuum to remove acetic acid. The residual slurry was dissolved in ethyl acetate (200 mL), filtered and the filtrate evaporated under vacuum to yield 15.95 g (98.6% yield) of the title compound as an oil. Thin layer chromatography analysis of the title compound showed a single spot with Rf=0.30 (silica, 3:2 ethyl acetate/hexane).

Example 64

Preparation of N-benzylsulfonyl-S-(methyl acetate)-L-cysteine sulfone-L-proline-O-benzyl ester

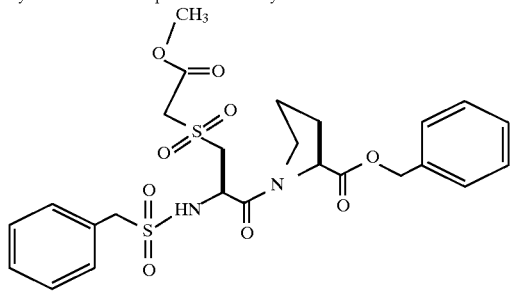

The compound of Example 63 (5.66 g, 10.9 mmole) was dissolved in 18 mL of 4N anhydrous hydrochloric acid/dioxane. The solution was stirred for several hours at room temperature until all starting material was consumed. The hydrochloric acid/dioxane solution was evaporated under vacuum to give an oil. The oil was dissolved in acetonitrile and evaporated under vacuum. This was done three times.

The remaining oil was suspended in 25 mL of acetonitrile, cooled to ice bath temperature, then benzylsulfonyl chloride (2.5 g, 13.1 mmole) and pyridine (2.6 g, 32.8 mmole) were added. The reaction was taken from the ice bath after 30 minutes and stirred at room temperature for 18 hours. The acetonitrile was evaporated under vacuum and the resulting oil was taken up in 200 mL ethyl acetate and washed successively with 1N hydrochloric acid (1×50 mL), saturated sodium bicarbonate 1×50 mL) and brine (1×50 mL). After drying with MgSO$_4$, the solvent was evaporated under vacuum to give crude product.

The crude product was purified by column chromatography on silica gel, eluting with 1:1 hexane/ethyl acetate to yield 2.9 g (46.9% yield) of the title compound as solid. Thin layer chromatography analysis of the title compound showed a single spot with Rf=0.27 (silica; 3:2 ethyl acetate/hexane).

Example 65

Preparation of N-benzylsulfonyl-S-(methyl acetate)-L-cysteine sulfone-L-proline

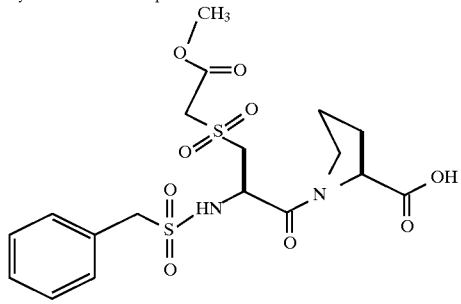

The compound of Example 64 (2.9 g, 5.12 mmole) was dissolved in THF (50 mL), 0.5 g of 10% palladium on carbon was added and the mixture was stirred under hydrogen gas at atmospheric pressure for 18 hours.

After the catalyst was filtered off the reaction mixture, the solvent was removed under vacuum and the resulting oil was taken up in a solution of saturated sodium bicarbonate. This solution was then extracted with ethyl acetate (1×150 mL) and the organic layer was decanted off. The remaining aqueous layer was layered with 100 mL of ethyl acetate and acidified with 1N hydrochloric acid to pH 2 (pH papers). After the phases separated, the organic layer was saved and the aqueous layer was then further extracted with ethyl acetate (3×100 mL).

The organic extracts were combined and washed with brine, dried with MgSO$_4$, filtered and evaporated under vacuum to give 2.17 g (yield 88.9%) of the title compound as a foamy solid. Thin layer chromatography analysis of the title compound showed a single spot with Rf=0.40 (silica, 90:10:2 dichloromethane/methanol/acetic acid).

Example 66

Preparation of N-benzylsulfonyl-S-(methyl acetate)-L-cysteine sulfone-L-proline-L-argininal

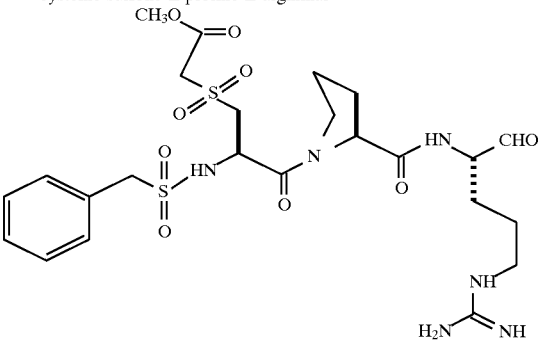

The title compound is prepared in the same manner as described in Example 8.

The compound of Example 65 is attached to the resin of Example 7. The title compound as a protected semicarbazone is then be cleaved from the resin and the semicarbazone is hydrolyzed to give the title compound.

Example 67

Preparation of N-(2-naphthylenesulfonyl)-S-(methyl acetate)-L-cysteine sulfone-L-proline-O-benzyl ester

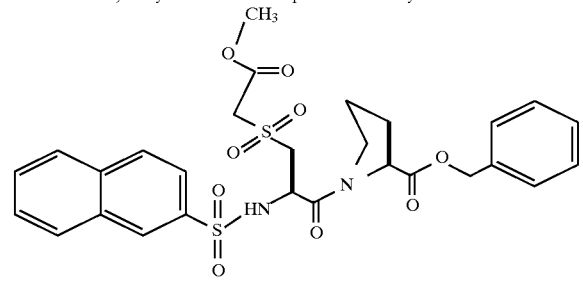

The compound of Example 63 (4.8 g, 9.37 mmole) was dissolved in 18 mL of 4N anhydrous hydrochloric acid/dioxane. The solution was stirred for several hours at room temperature until all starting material was consumed. The hydrochloric acid/dioxane solution was evaporated under vacuum to give an oil. The oil was dissolved in acetonitrile and evaporated under vacuum. This was done three times.

The remaining oil was suspended in 35 mL of acetonitrile, cooled to ice bath temperature, then 2-naphthylenesulfonyl chloride (2.55 g, 11.2 mmole) and pyridine (2.2 g, 28.1 mmole) were added. The reaction was taken from the ice bath after 30 minutes and stirred at room temperature for 18 hours. The acetonitrile was evaporated under vacuum and the resulting oil was taken up in 200 mL ethyl acetate and washed successively with 1N hydrochloric acid (1×50 mL), saturated sodium bicarbonate 1×50 mL) and brine (1×50 mL). After drying with MgSO₄, the solvent was evaporated under vacuum to give crude product.

The crude product was purified by column chromatography on silica gel, eluting with 99.25:0.75 dichloromethane/methanol to yield 3.9 g (69.0% yield) of the title compound as solid. Thin layer chromatography analysis of the title compound showed a single spot with Rf=0.35 (silica; 3:2 ethyl acetate/hexane).

Example 68

Preparation of N-(2-naphthylenesulfonyl)-S-(methyl acetate)-L-cysteine sulfone-L-proline

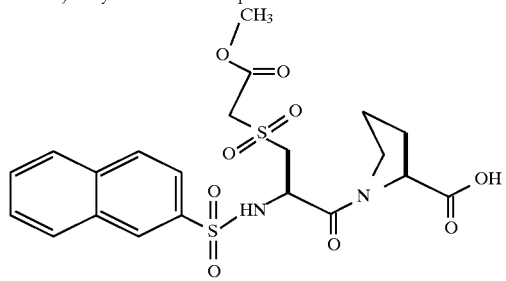

The compound of Example 67 (3.90 g, 6.47 mmole) was dissolved in THF (50 mL), 0.5 g of 10% palladium on carbon was added and the mixture was stirred under hydrogen gas at atmospheric pressure for 18 hours.

After the catalyst was filtered off the reaction mixture, the solvent was removed under vacuum and the resulting oil was taken up in a solution of saturated sodium bicarbonate. This solution was then extracted with ethyl acetate (1×150 mL) and the organic layer was decanted off. The remaining aqueous layer was layered with 100 mL of ethyl acetate and acidified with 1N hydrochloric acid to pH 2 (pH papers). After the phases separated, the organic layer was saved and the aqueous layer was then further extracted with ethyl acetate (3×100 mL).

The organic extracts were combined and washed with brine, dried with MgSO₄, filtered and evaporated under vacuum to give 2.84 g (yield 85.8%) of the title compound as a foamy solid. Thin layer chromatography analysis of the title compound showed a single spot with Rf=0.40 (silica, 90:10:2 dichloromethane/methanol/acetic acid).

Example 69

Preparation of N-(2-naphthylenesulfonyl)-S-(methyl acetate)-L-cysteine sulfone-L-proline-L-argininal

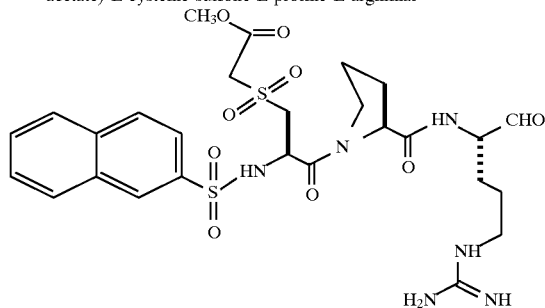

The title compound was prepared in the same manner as described in Example 8.

The compound of Example 68 [N-(2-naphthylenesulfonyl)-S-(methyl acetate)-L-cysteine sulfone-L-proline] was attached to the resin of Example 7. After cleavage of the title compound as a protected semicarbazone from the resin, the semicarbazone was hydrolyzed to give the title compound.

Fast atom bombardment mass spectrometry confirmed the theoretical molecular weight of 652.

Example 70

Preparation of S-(cyanomethyl)-L-cysteine

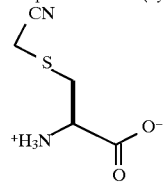

A 360 mL aqueous solution of commercially available (Aldrich) L-cysteine hydrochloride monohydrate (60.0 g, 341.7 mmole) and sodium hydroxide (27.33 g, 683.4 mmole), at room temperature, is treated with a solution of bromoacetonitrile (44.5 g, 370.6 mmole) in 130 mL of dioxane over 30 minutes. The reaction is stirred for 18 hours, during which time a thick precipitate will form. The solid is filtered off, washed with diethyl ether (100 mL) and dried under high vacuum at 40° C. to give the title compound.

Example 71

Preparation of N—Boc—S-(cyanomethyl)-L-cysteine

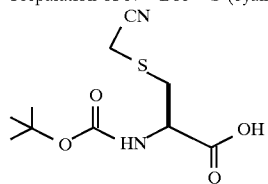

The compound of Example 70 (54.7 g, 341.7 mmole) and sodium bicarbonate (33.96 g, 404 mmole) are suspended in 600 mL of deionized water. A solution of di-t-butyl dicarbonate (80.88 g, 370 mmole) in 350 mL of dioxane is added and the slurry is stirred for 18 hours.

The slurry is extracted with diethyl ether (2×100 mL). The slurry is layered with ethyl acetate (200 mL) and acidified with 1N hydrochloric acid to pH 2 (pH papers). The resulting organic layer is saved and the remaining aqueous layer is further extracted with ethyl acetate (2×200 mL). The organic extracts are combined, washed with brine, dried with MgSO₄ and the solvent evaporated under vacuum to give the title compound.

Example 72

Preparation of N—Boc—S-(cyanomethyl)-L-cysteine-L-proline-O-benzyl ester

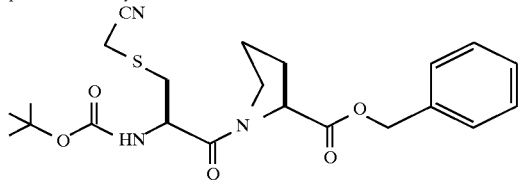

The compound of Example 71 (24.72, 95.06 mmole) and L-proline-O-benzyl ester hydrochloride (22.98 g, 95.06 mmole) are suspended in 140 mL of acetonitrile and 120 mL of DMF at 0° C., then BOP (42.0 g, 95.06 mmole) and NMM (28.84 g, 285.18 mmole) are added. The ice bath is removed after 30 minutes and the reaction is stirred for 18 hours at room temperature. The reaction mixture is reduced in volume under vacuum at 25° C. to give a residue. The residue is taken up in 200 mL ethyl acetate, and is washed successively with 1N hydrochloric acid (1×50 mL) saturated sodium bicarbonate 1×50 mL) and brine (1×50 mL). After drying with MgSO$_4$, the solvent is evaporated under vacuum to give the title compound.

Example 73

Preparation of N—Boc—S-(cyanomethyl)-L-cysteine sulfone-L-proline-O-benzyl ester

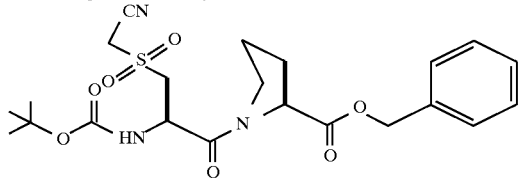

The compound of Example 72 (23.96 g, 55.07 nmole) is dissolved in 300 mL of glacial acetic acid, sodium perborate tetrahydrate (42.36 g, 275.35 mmole) is added and the mixture is heated to 55° C. After 2.5 hours at this temperature, the reaction mixture is diluted with 1 liter of brine, the aqueous layer is extracted with ethyl acetate (4×250 mL) and the combined organic extracts are dried with MgSO$_4$. This solution is filtered and evaporated under vacuum, then repeatedly azeotroped with toluene (200 mL) under vacuum to remove acetic acid. The residue is dissolved in ethyl acetate (200 mL), filtered and the filtrate is evaporated under vacuum to give the title compound.

Example 74

Preparation of N-benzylsulfonyl-S-(cyanomethyl)-L-cysteine sulfone-L-proline-O-benzyl ester

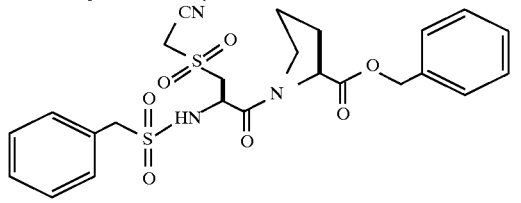

A solution of the compound of Example 73 (4.3 g, 9.28 mmole) in 105 mL of sieve-dried ethyl acetate is prepared. To this, 26 mL of 5.7N anhydrous hydrochloric acid/ethyl acetate (that is generated in situ from acetyl chloride and methanol) is added. This mixture is stirred for several hours at room temperature until all starting material is consumed. The mixture is evaporated under vacuum and the residue is dissolved in acetonitrile and then evaporated under vacuum. This was done three times to give a further residue.

The residue is suspended in 35 mL of acetonitrile, cooled to ice bath temperature, then benzylsulfonyl chloride (2.12 g, 11.14 mmole) and pyridine (2.93 g, 37.12 mmole) are added. The reaction is removed from the ice bath after 30 minutes and allowed to stir at room temperature for 18 hours. The reaction mixture is reduced in volume under vacuum to a residue which is taken up in 200 mL ethyl acetate and washed successively with 1N hydrochloric acid (1×50 mL), saturated sodium bicarbonate (1×50 mL) and brine (1×50 mL). After drying with MgSO$_4$, the solvent is evaporated under vacuum to give the title compound.

Example 75

Preparation of N-benzylsulfonyl-S-(tetrazol-5-yl)-L-cysteine methyl sulfone-L-proline-O-benzyl ester

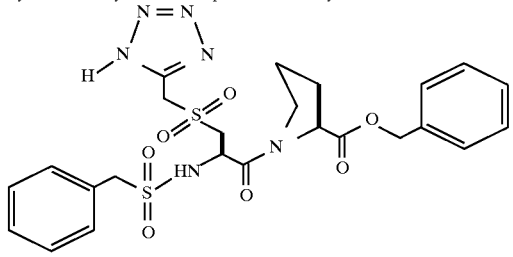

To the compound of Example 74 (5.3 g, 10.0 mmole) which is dissolved in 20 mL of THF is added tributyltin azide (4.71 g, 15.0 mmole). The reaction mixture is refluxed for three days. The reaction mixture is allowed to cool and the volatiles are removed under vacuum. The residue is dissolved in 50 mL of saturated sodium bicarbonate and is washed with ethyl acetate (3×25 mL). The aqueous phase is then acidified to pH 3 with 1N hydrochloric acid, then is extracted with ethyl acetate (3×75 mL). The combined organic extracts are dried over MgSO4 and the solvent is removed under vacuum to give the title compound.

Example 76

Preparation of N-benzylsulfonyl-S-(tetrazol-5-yl)-L-cysteine methyl sulfone-L-proline

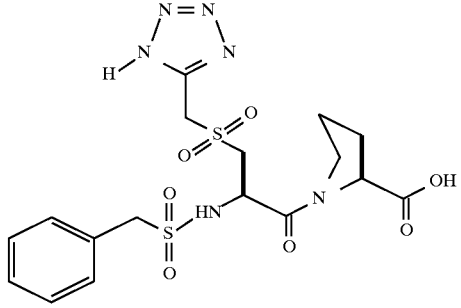

The compound of Example 75 (2.77 g, 4.81 mmole) is dissolved in THF (50 mL), 0.5 g of 10% palladium on carbon is added and the mixture is stirred under hydrogen gas at atmospheric pressure for 18 hours.

After the catalyst is filtered off the reaction mixture, the solvent is removed under vacuum and the resulting residue is taken up in a solution of saturated sodium bicarbonate. This solution is then extracted with ethyl acetate (1×150 mL) and the organic layer is decanted off. The remaining aqueous layer is layered with 100 mL of ethyl acetate and acidified with 1N hydrochloric acid to pH 2 (pH papers). After the phases separate, the organic layer is saved and the aqueous layer is then further extracted with ethyl acetate (3×100 mL).

The organic extracts are combined and washed with brine, dried with MgSO$_4$, filtered and evaporated under vacuum to give the title compound.

Example 77

Preparation of N-benzylsulfonyl-S-(tetrazol-5-yl)-L-cysteine methyl sulfone-L-proline-L-argininal

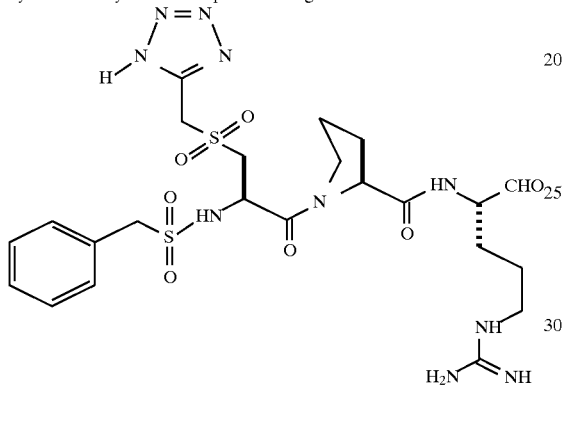

The title compound is prepared in the same manner as described in Example 8.

The compound of Example 76 is attached to the resin of Example 7. The title compound is cleaved from the resin as a protected semicarbazone. The semicarbazone is hydrolyzed to give the title compound.

Example 78

Preparation of N—Boc—L-2-azetidinecarboxylic acid

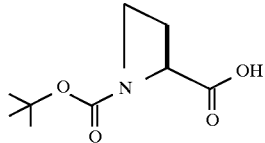

L-2-azetidinecarboxylic acid (34.5 g, 341.7 mmole) and sodium bicarbonate (33.96 g, 404 mmole) are suspended in 600 mL of deionized water. A solution of di-t-butyl dicarbonate (80.88 g, 370 mmole) in 350 mL of dioxane is added and the slurry is stirred for 18 hours.

The slurry is extracted with diethyl ether (2×100 mL). The slurry is layered with ethyl acetate (200 mL) and acidified with 1N hydrochloric acid to pH 2 (pH papers). The resulting organic layer is saved and the remaining aqueous layer is further extracted with ethyl acetate (2×200 mL). The organic extracts are combined, washed with brine, dried with MgSO$_4$ and the solvent evaporated under vacuum to give the title compound.

Example 79

Preparation of N—Boc—L-2-azetidinecarboxylic acid-O-benzyl ester

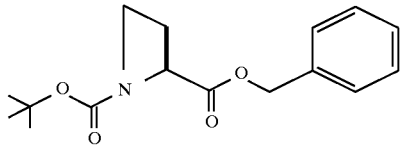

To a solution of compound of Example 78 (178 mmole) in dry THF (500 mL) which is chilled to 0° C., carbonyl diimidazole (34.6 g, 214 mmole) is added in small portions. After 30 minutes, the mixture is warmed to room temperature for 2 hours until all of the CO$_2$ evolution ceases. After this time, benzyl alcohol (27.6 mL, 267 mmole) is added and the reaction is stirred for 12 hours.

The reaction mixture is then reduced in volume under vacuum and the residue is diluted with ethyl acetate (500 mL). The organic phase are washed with saturated bicarbonate (1×100 mL), brine (100 mL), saturated aqueous citric acid (1×100 mL), dried over MgSO$_4$, filtered and the solvent is removed under vacuum to give the title compound.

Example 80

Preparation of L-2-azetidinecarboxylic acid-O-benzyl ester hydrochloride salt

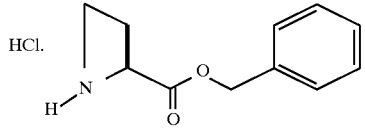

The compound of Example 79 (50.0 g) is dissolved in 200 mL of a 4M solution of HCl in dioxine. The reaction mixture is stirred 2 hours. The solution is reduced in volume under vacuum. The resulting solid is washed with diethyl ether to give the title compound.

Example 81

Preparation of L-methionine sulfone-L-2-azetidinecarboxylic acid-O-benzyl ester hydrochloride salt

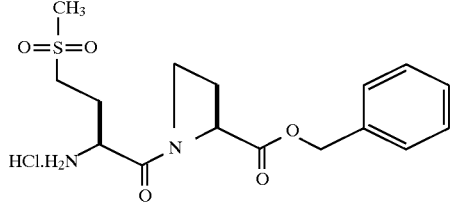

A. Procedure 1

N-Boc-L-methionine sulfone-L-2-azetidinecarboxylic acid-O-benzyl ester is prepared by adding to a solution of N-Boc-L-methioninesulfone (14.0 g, 50.0 mmole) in dichloromethane (150 mL) at 0° C., HOBt (10.1 g, 75 mmole) followed by DCC (11.33 g, 55.0 mmole). The mixture is stirred for 10 minutes, and then the compound of Example 80 (50.0 mmole) is added followed by NMM (100 mmole, 10.9 mL). The resulting mixture is stirred in an ice bath and is allowed to come to room temperature over 12 hours. The mixture is filtered to remove dicyclohexylurea and ethyl acetate (300 mL) is added. The organic phase is then added to a separatory funnel and is washed with saturated aqueous sodium bicarbonate, brine and then 1M aqueous HCl. The organic phase is dried over magnesium sulfate and then is filtered. The organic phase is reduced on a rotary evaporator under vacuum and then on a high vacuum line to remove traces of solvent to give N-Boc-L-methionine sulfone-L-2-azetidinecarboxylic acid-O-benzyl ester.

To a solution of N-Boc-L-methionine sulfone-L-2-azetidinecarboxylic acid-O-benzyl ester (50 mmole) in dry dioxane (300 mL) is added 100 mL of a 4M HCl/dioxane solution. The mixture is then stirred at room temperature for 1 hour until the starting material disappears. Diethyl ether is added to the mixture to precipitate the title compound. The mixture is filtered off on a Buchner funnel and dried under high vacuum to give the title compound.

B. Procedure 2

Alternatively, the title compound is synthesized by the following method.

To a solution of N-Boc-L-methionine sulfone (5 g, 20 mmole) in 80 mL of dry DMF is added compound of Example 80 (20 mmole) followed by BOP (8.9 g, 20 mmole) and NMM (5.5 mL, 20 mmole). The mixture is stirred for 16 hours at room temperature. The reaction mixture is dissolved in 600 mL of ethyl acetate and is washed with 200 mL each of water, 1M aqueous HCl, water, saturated aqueous sodium bicarbonate and brine. The organic phase is dried over magnesium sulfate, filtered and the solvent is removed under vacuum to give a residue.

To the solution of the residue in 20 mL dichloromethane, 100 mL of a 4M solution of HCl in dioxane is added. After stirring for 16 hours, the solvent is removed under vacuum. The resulting residue is precipitated using diethyl ether, filtered and dried under vacuum to give the title compound.

Example 82

Preparation of N-(1-butanesulfonyl)-L-methioninesulfone-L-2-azetidinecarboxylic acid

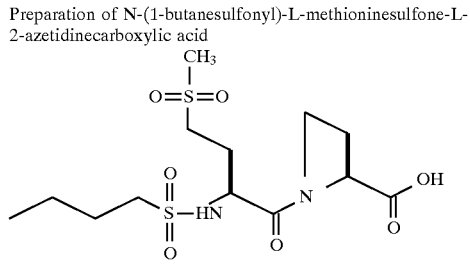

The compound of Example 81 (12.4 mmole) is reacted with 2.07 mL (16 mmole) of 1-butanesulfonylchloride and 5.0 mL (36 mmole) of triethylamine in dichloromethane from 0° C. to room temperature. The reaction mixture is poured into saturated aqueous bicarbonate and extracted with ethyl acetate (2×100 mL). The organic phase is washed with brine and 1M aqueous HCl. The organic phase is separated and dried over magnesium sulfate, filtered and reduced under vacuum to give a residue.

The residue is mixed with 2M potassium hydroxide (20 mL) and 100 mL methanol at room temperature for two hours. The methanol is reduced under vacuum and the aqueous solution is then washed with ether (2×50 mL) and then neutralized with 1M HCl to a pH of 1. The aqueous solution is extracted with ethyl acetate (2×100 mL), dried over MgSO₄, filtered and reduced under vacuum to give the title compound.

Example 83

Preparation of N-(1-butanesulfonyl)-L-methioninesulfone-L-2-azetidinecarboxylic acid-L-argininal

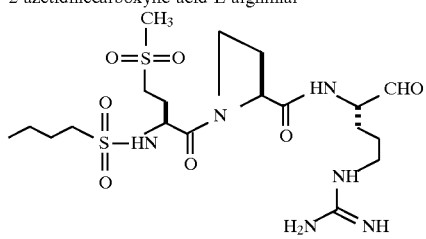

The title compound is prepared in the same manner as described in Example 8.

The compound of Example 82 is attached to the resin of Example 7. The title compound is cleaved from the resin as a protected semicarbazone. The semicarbazone is hydrolyzed to give the title compound.

Example 84

Preparation of N-(2-naphthylenesulfonyl)-L-methionine sulfone-L-2-azetidinecarboxylic acid-O-benzyl ester

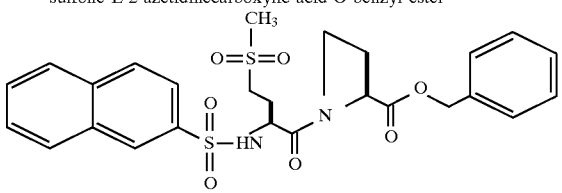

The compound of Example 81 (6.9 mmole) is added to 69 mL of acetonitrile. To this mixture, 2.34 g (10.3 mmole, 1.5 eq.) of 2-naphthylenesulfonylchloride and 4.20 g (4.12 mL, 34.4 mmole, 5 eq.) of pyridine are added and the mixture is stirred for 10 hours. The mixture is then concentrated under vacuum, diluted with ethyl acetate (500 mL) and washed with 1M HCl, water, aqueous sodium bicarbonate, and brine. The organic phase is dried over MgSO₄ and concentrated under vacuum to give a residue. The residue is then filtered down a plug of silica, eluting with dichloromethane (100 mL), then 10% methanol/dichloromethane (200 mL) to give the title compound.

Example 85

Preparation of N-(2-naphthylenesulfonyl)-L-methionine sulfone-L-2-azetidinecarboxylic acid

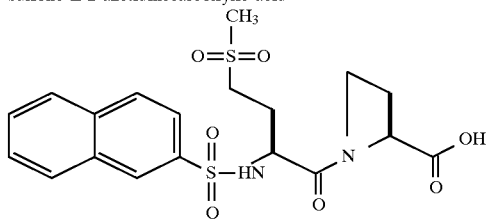

The compound of Example 84 (7.1 mmole) is dissolved in 250 mL of methanol with a trace of THF. To this solution, 2 g of 10% palladium on carbon is added under a nitrogen blanket. The mixture is then stirred under hydrogen at one atmosphere of pressure for 10 hours. The mixture is filtered through a nylon filter and concentrated under vacuum to give the title compound.

Example 86

Preparation of N-(2-naphthylenesulfonyl)-L-methionine sulfone-L-2-azetidinecarboxylic acid-L-argininal

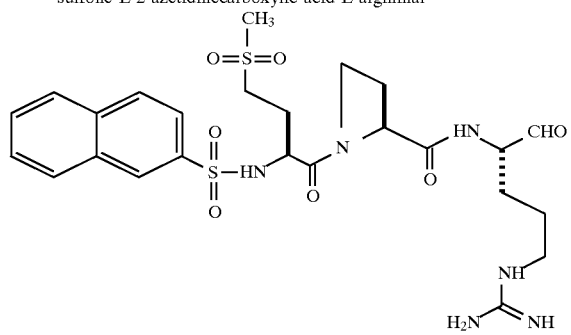

The title compound is prepared in the same manner as described in Example 8.

The compound of Example 85 is attached to the resin of Example 7. The title compound is cleaved from the resin as a protected semicarbazone. The semicarbazone is hydrolyzed to give the title compound.

Example 87

Preparation of N-benzylsulfonyl-L-methionine sulfone-L-2-azetidinecarboxylic acid-O-benzyl ester

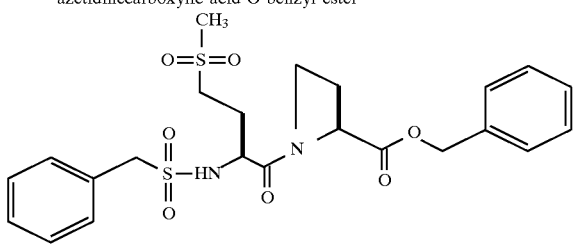

To a solution of the compound of Example 81 (20.0 mmole) in dry acetonitrile (100 mL) cooled to 0° C., alpha-toluenesulfonylchloride (20.0 mmole, 3.8 g) is added all at once followed by pyridine (50.0 mmole, 4.2 mL). The mixture is then stirred in the ice bath for 12 hours during which time the mixture is allowed to warm to room temperature.

The reaction mixture is reduced to a residue under vacuum. The residue is taken up ethyl acetate (300 mL) and washed with saturated aqueous sodium bicarbonate, brine, 1M aqueous HCl (100 mL), dried over MgSO$_4$, filtered and evaporated under vacuum to give the title compound. The solid is filtered through a plug of silica gel (50 g) using ethyl acetate as eluent before hydrogenation to eliminate possible sulfur related impurities.

Example 88

Preparation of N-benzylsulfonyl-L-methionine sulfone-L-2-azetidinecarboxylic acid

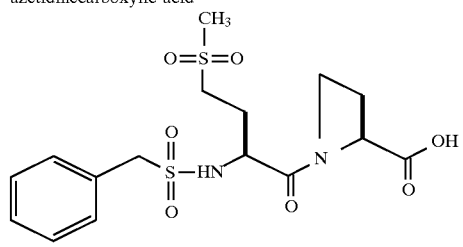

To a solution of the compound of Example 87 (20 mmole) in methanol (300 mL), 1.0 g of 10% palladium on carbon is added. The mixture is then hydrogenated at 1 atmosphere of hydrogen gas at room temperature for 12 hours with stirring. The mixture is filtered and reduced under vacuum to give the title compound.

Example 89

Preparation of N-benzylsulfonyl-L-methionine sulfone-L-2-azetidinecarboxylic acid-L-argininal

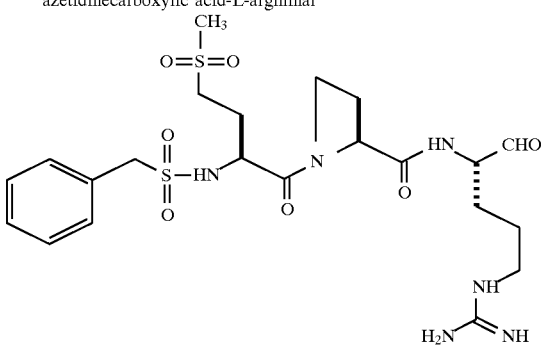

The title compound is prepared in the same manner as described in Example 8.

The compound of Example 88 is attached to the resin of Example 7. The title compound is cleaved from the resin as a protected semicarbazone. The semicarbazone is hydrolyzed to give the title compound.

Example 90

Preparation of N-(2-propylpentanoyl)-L-methionine sulfone-L-2-azetidinecarboxylic acid-O-benzyl ester

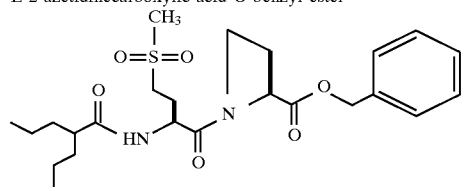

The compound of Example 81 (4.66 mmole) is dissolved in 12 mL of 4N anhydrous hydrochloric acid/dioxane. The solution is stirred for several hours at room temperature until all starting material is consumed. The hydrochloric acid/dioxane solution is evaporated under vacuum to give a residue. The residue is dissolved in acetonitrile and evaporated under vacuum. This is done three times to give a residue.

The residue is suspended in 25 mL of acetonitrile, cooled to ice bath temperature, then 2-propylpentanoic acid (0.95 g, 6.6 mmole), BOP (2.92 g, 6.6 mmole) and NMM (2.0 g, 19,8 mmole) are added. The reaction is taken from the ice bath after 30 minutes and stirred at room temperature for 18 hours. The acetonitrile is evaporated under vacuum and the residue is taken up in ethyl acetate (200 mL) and washed successively with 1N hydrochloric acid (1×50 mL), saturated sodium bicarbonate (1×50 mL) and brine (1×50 mL). After drying with MgSO$_4$, the ethyl acetate is evaporated under vacuum to yield crude product.

The crude product is purified by column chromatography on silica gel to give the title compound.

Example 91

Preparation of N-(2-propylpentanoyl)-L-methionine sulfone-L-2-azetidinecarboxylic acid

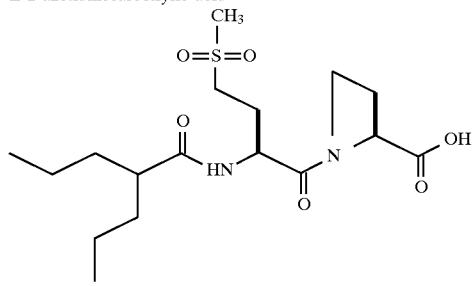

The compound of Example 90 (3.64 mmole) is dissolved in THF (50 mL), 0.5 g of 10% palladium on carbon is added and the mixture is stirred under hydrogen gas at atmospheric pressure for 18 hours.

After the catalyst is filtered from the reaction mixture, the solvent is removed under vacuum and the residue is taken up in a solution of saturated sodium bicarbonate. This solution is then extracted with ethyl acetate (1×150 mL) and the organic layer is decanted off. The remaining aqueous layer is layered with 100 mL of ethyl acetate and acidified with 1N hydrochloric acid to pH 2 (pH papers). After the phases separate, the organic layer is saved and the aqueous layer is then further extracted with ethyl acetate (3×100 mL).

The organic extracts are combined and washed with brine, dried with MgSO$_4$, filtered and evaporated under vacuum to give the title compound.

Example 92

Preparation of N-(2-propylpentanoyl)-L-methionine sulfone-L-2-azetidinecarboxylic acid-L-argininal

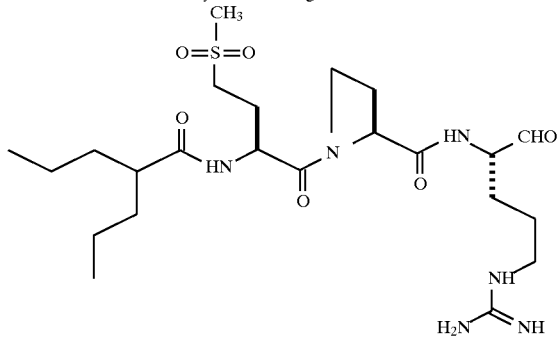

The title compound is prepared in the same manner as described in Example 8.

The compound of Example 91 is attached to the resin of Example 7. The title compound is cleaved from the resin as a protected semicarbazone. The semicarbazone is hydrolyzed to give the title compound. 0.1 mL of thiocresol is additionally added to the anisole-HF cleavage mixture.

Example 93

Preparation of N—Boc—S-methyl-L-cysteine-L-2-azetidinecarboxylic acid-O-benzyl ester

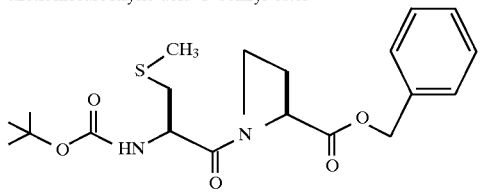

The compound of Example 35 [N-Boc-S-methyl-L-cysteine] (14.64 g, 62.2 mmole) and the compound of Example 80 [L-2-azetidinecarboxylic acid-O-benzyl ester] (62.2 mmole) are suspended in 135 mL of acetonitrile at 0° C., then BOP (27.51 g, 62.2 mmole) and NNM (18.9 g, 186.6 mmole) are added. The ice bath is removed after 30 minutes and the reaction is stirred for 18 hours at room temperature.

The solvent from reaction mixture is evaporated at 25° C. under vacuum to give a residue which is dissolved in ethyl acetate (250 mL). This solution is successively washed with 1N hydrochloric acid (1×50 mL), saturated sodium bicarbonate (1×50 mL) and brine (1×50 mL), and then is dried with MgSO$_4$. The solvent is evaporated under vacuum to give crude product.

The crude product is purified by column chromatography on silica gel to give the title compound.

Example 94

Preparation of N—Boc—S-methyl-L-cysteine sulfone-L-2-azetidinecarboxylic acid-O-benzyl ester

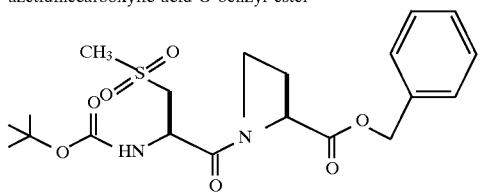

The compound of Example 93 (38.2 mmole) is dissolved in 200 mL of glacial acetic acid and sodium perborate tetrahydrate (29.37 g, 190.9 mmole) is added and the mixture is heated to 55° C. After 2.5 hours, at this temperature, the reaction solution is diluted with 800 mL of brine, the aqueous layer is extracted with ethyl acetate (3×250 mL) and the combined organic extracts are dried with MgSO$_4$. This solution is filtered, evaporated under vacuum to yield a residue that is repeatedly azeotroped with toluene (200 mL) under vacuum to remove acetic acid. The residual slurry is suspended in ethyl acetate (200 mL), filtered and the solvent is evaporated under vacuum to give the title compound.

Example 95

Preparation of N-(1-butanesulfonyl)-S-methyl-L-cysteine sulfone-L-2-azetidinecarboxylic acid-O-benzyl ester

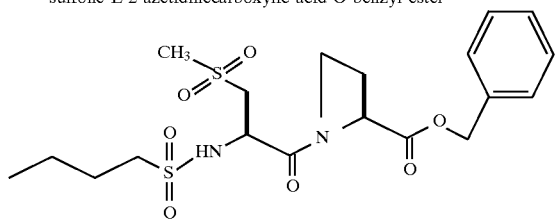

The compound of Example 94 (4.4 mmole) is dissolved in 12 mL of 4N anhydrous hydrochloric acid/dioxane and is stirred for several hours at room temperature until all starting material is consumed. The hydrochloric acid/dioxane solution is then evaporated under vacuum to yield a residue. This residue is dissolved in acetonitrile and evaporated under vacuum. This is done three times to give a further residue.

The residue is suspended in 17 mL of acetonitrile, cooled to ice bath temperature, then 1-butanesulfonyl chloride (0.69 g, 4.4 mmole) and pyridine (1.04 g, 13.2 mmole) are added. The reaction is taken from the ice bath after 30 minutes and is stirred at room temperature for 18 hours. The reaction mixture is evaporated under vacuum to give a residue. The residue is taken up in 200 mL ethyl acetate, and washed successively with 1N hydrochloric acid (1×50 mL) saturated sodium bicarbonate 1×50 mL) and brine (1×50 mL). After drying with MgSO$_4$, the solvent is evaporated under vacuum to give crude product.

The crude product is purified by column chromatography silica gel to give the title compound.

Example 96

Preparation of N-(1-butanesulfonyl)-S-methyl-L-cysteine sulfone-L-2-azetidinecarboxylic acid

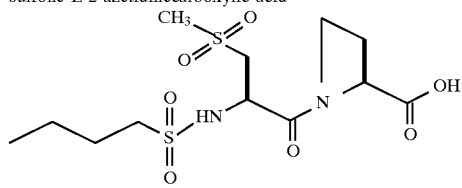

The compound of Example 95 (1.55 g, 2.45 mmole) is dissolved in THF (50 mL), 0.5 g of 10% palladium on carbon is added and the mixture is stirred under hydrogen gas at atmospheric pressure for 18 hours.

After the catalyst is filtered from the reaction mixture, the solvent is removed under vacuum and the residue is taken up in a solution of saturated sodium bicarbonate. This solution is then extracted with ethyl acetate (1×150 mL) and the organic layer is decanted off. The remaining aqueous layer is layered with 100 mL of ethyl acetate and acidified with 1N hydrochloric acid to pH 2 (pH papers). After the phases separate, the organic layer is saved and the aqueous layer is then further extracted with ethyl acetate (3×100 mL).

The organic extracts are combined and washed with brine, dried with MgSO$_4$, filtered and evaporated under vacuum to give the title compound.

Example 97

Preparation of N-(1-butanesulfonyl)-S-methyl-L-cysteine sulfone-L-2-azetidinecarboxylic acid-L-argininal

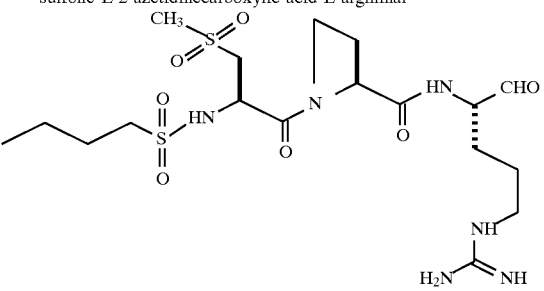

The title compound is prepared in the same manner as described in Example 8.

The compound of Example 96 is attached to the resin of Example 7. The title compound is cleaved from the resin as a protected semicarbazone. The semicarbazone is hydrolyzed to give the title compound. 0.1 mL of thiocresol is additionally added to the anisole-HF cleavage mixture.

Example 98

Preparation of N-(2-naphthalenesulfonyl)-S-methyl-L-cysteine sulfone-L-2-azetidinecarboxylic acid-O-benzyl ester

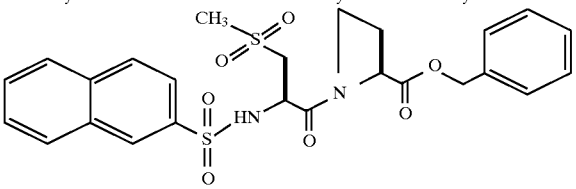

The compound of Example 94 (6.6 mmole) is dissolved in 12 mL of 4N anhydrous hydrochloric acid/dioxane. The solution is stirred for several hours at room temperature until all starting material is consumed. The hydrochloric acid/dioxane solution is evaporated under vacuum. The residue is dissolved in acetonitrile and evaporated under vacuum. This is done three times to give a further residue.

The residue is suspended in 20 mL of acetonitrile, cooled to ice bath temperature, then 2-naphthalenesulfonyl chloride (0.1.49 g, 6.6 mmole) and pyridine (1.57 g, 19.8 mmole) are added. The reaction is taken from the ice bath after 30 minutes and stirred at room temperature for 18 hours. The acetonitrile is evaporated under vacuum to give residue which is taken up in ethyl acetate (200 mL) and washed successively with 1N hydrochloric acid (1×50 mL), saturated sodium bicarbonate (1×50 mL) and brine (1×50 mL). The solution is dried with MgSO$_4$ and evaporated under vacuum will give crude product.

The crude product is purified by column chromatography on silica gel to give the title compound.

Example 99

Preparation of N-(2-naphthalenesulfonyl)-S-methyl-L-cysteine sulfone-L-2-azetidinecarboxylic acid

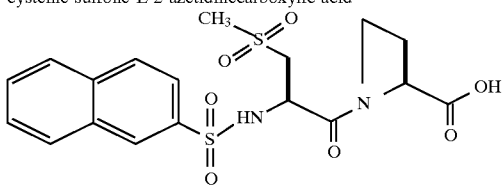

The compound of Example 98 (3.58 mmole) is dissolved in THF (50 mL), 0.5 g of 10% palladium on carbon is added and the mixture is stirred under hydrogen gas at atmospheric pressure for 18 hours.

After the catalyst is filtered off the reaction mixture, the solvent is removed under vacuum to give a residue. The residue is taken up in a solution of saturated sodium bicarbonate, extracted with ethyl acetate (1×150 mL) and the organic layer is decanted off. The remaining aqueous layer is layered with 100 mL of ethyl acetate and acidified with 1N hydrochloric acid to pH 2 (pH papers). After the phases separate, the organic layer is saved and the aqueous layer is then further extracted with ethyl acetate (3×100 mL).

The organic extracts are combined and washed with brine, dried with $MgSO_4$, filtered and evaporated under vacuum to give the title compound.

Example 100

Preparation of N-(2-naphthalenesulfonyl)-S-methyl-L-cysteine sulfone-L-2-azetidinecarboxylic acid-L-argininal

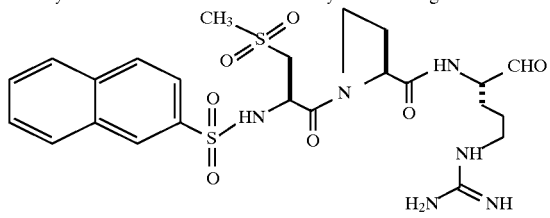

The title compound is prepared in the same manner as described in Example 8.

The compound of Example 99 is attached to the resin of Example 7. The title compound is cleaved from the resin as a protected semicarbazone. The semicarbazone is hydrolyzed to give the title compound.

Example 101

Preparation of N-benzylsulfonyl-S-methyl-L-cysteine sulfone-L-2-azetidinecarboxylic acid-O-benzyl ester

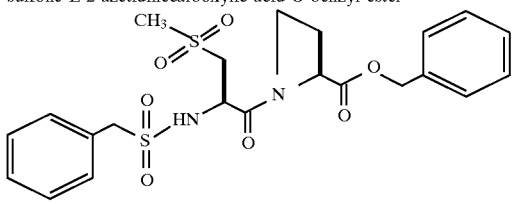

The compound of Example 94 (6.6 mmole) is dissolved in 12 mL of 4N anhydrous hydrochloric acid/dioxane. The solution is stirred for several hours at room temperature until all starting material is consumed. The hydrochloric acid/dioxane solution is evaporated under vacuum. The residue is dissolved in acetonitrile and evaporated under vacuum. This is done three times to yield a further residue.

The residue is suspended in 20 mL of acetonitrile, cooled to ice bath temperature, then alpha-toluenesulfonyl chloride (0.1.49 g, 6.6 mmole) and pyridine (1.57 g, 19.8 mmole) are added. The reaction is taken from the ice bath after 30 minutes and stirred at room temperature for 18 hours. The acetonitrile is evaporated under vacuum to give residue which is taken up in ethyl acetate (200 mL) and washed successively with 1N hydrochloric acid (1×50 mL), saturated sodium bicarbonate (1×50 mL) and brine (1×50 mL). The solution is dried with $MgSO_4$ and evaporated under vacuum to give crude product.

The crude product is purified by column chromatography on silica gel to give the title compound.

Example 102

Preparation of N-benzylsulfonyl-S-methyl-L-cysteine sulfone-L-2-azetidinecarboxylic acid

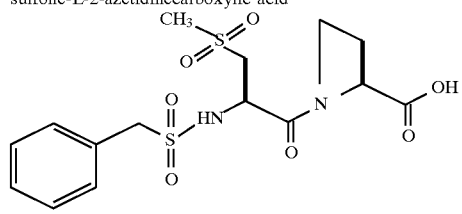

The compound of Example 101 (1.95 g, 3.58 mmole) is dissolved in THF (50 mL), 0.5 g of 10% palladium on carbon is added and the mixture is stirred under hydrogen gas at atmospheric pressure for 18 hours.

After the catalyst is filtered off the reaction mixture, the solvent is removed under vacuum and the residue is taken up in a solution of saturated sodium bicarbonate. This solution is then extracted with ethyl acetate (1×150 mL) and the organic layer is decanted off. The remaining aqueous layer is layered with 100 mL of ethyl acetate and acidified with 1N hydrochloric acid to pH 2 (pH papers). After the phases separate, the organic layer is saved and the aqueous layer is then further extracted with ethyl acetate (3×100 mL).

The organic extracts are combined and washed with brine, dried with $MgSO_4$, filtered and evaporated under vacuum to give the title compound.

Example 103

Preparation of N-benzylsulfonyl-S-methyl-L-cysteine sulfone-L-2-azetidinecarboxylic acid-L-argininal

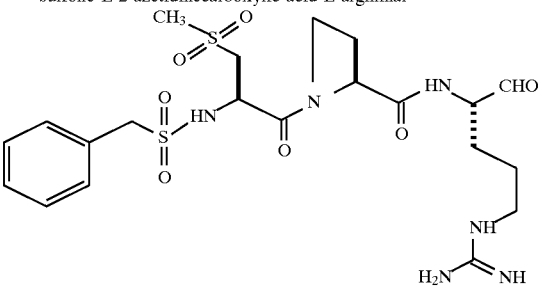

The title compound is prepared in the same manner as described in Example 8.

The compound of Example 102 is attached to the resin of Example 7. The title compound is cleaved from the resin as

Example 104

Preparation of N-(2-propylpentanoyl)-S-methyl-L-cysteine sulfone-L-2-azetidinecarboxylic acid-O-benzyl ester

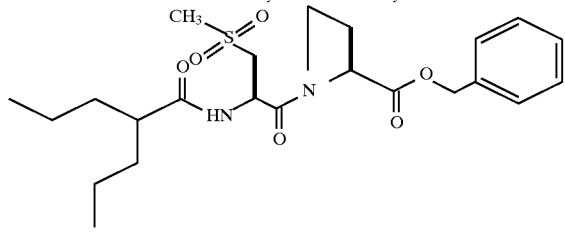

The compound of Example 94 (3.0 g, 4.66 mmole) is dissolved in 12 mL of 4N anhydrous hydrochloric acid/dioxane. The solution is stirred for several hours at room temperature until all starting material is consumed. The hydrochloric acid/dioxane solution is evaporated under vacuum to give a residue. This residue is dissolved in acetonitrile and evaporated under vacuum. This is done three times to yield a further residue.

The residue is suspended in 25 mL of acetonitrile, cooled to ice bath temperature, then 2-propylpentanoic acid (0.95 g, 6.6 mmole), BOP (2.92 g, 6.6 mmole) and NMM (2.0 g, 19,8 mmole) are added. The reaction is taken from the ice bath after 30 minutes and stirred at room temperature for 18 hours. The acetonitrile is evaporated under vacuum to give residue which is taken up in ethyl acetate (200 mL) and washed successively with 1N hydrochloric acid (1×50 mL), saturated sodium bicarbonate (1×50 mL) and brine (1×50 mL). The solution is dried with MgSO$_4$ and evaporated under vacuum to give crude product.

The crude product is purified by column chromatography on silica gel to give the title compound.

Example 105

Preparation of N-(2-propylpentanoyl)-S-methyl-L-cysteine sulfone-L-2-azetidinecarboxylic acid

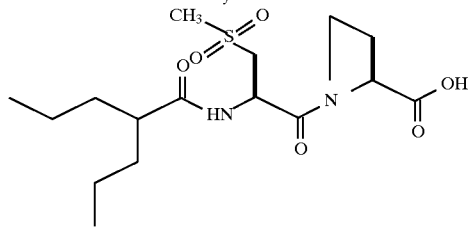

The compound of Example 104 (1.75 g, 3.64 mmole) is dissolved in THF (50 mL), 0.5 g of 10% palladium on carbon is added and the mixture is stirred under hydrogen gas at atmospheric pressure for 18 hours.

After the catalyst is filtered off the reaction mixture, the solvent is removed under vacuum and the residue is taken up in a solution of saturated sodium bicarbonate. This solution is then extracted with ethyl acetate (1×150 mL) and the organic layer is decanted off. The remaining aqueous layer is layered with 100 mL of ethyl acetate and acidified with 1N hydrochloric acid to pH 2 (pH papers). After the phases separate, the organic layer is saved and the aqueous layer is then further extracted with ethyl acetate (3×100 mL).

The organic extracts are combined and washed with brine, dried with MgSO$_4$, filtered and evaporated under vacuum to give the title compound.

Example 106

Preparation of N-(2-propylpentanoyl)-S-methyl-L-cysteine sulfone-L-2-azetidinecarboxylic acid-L-argininal

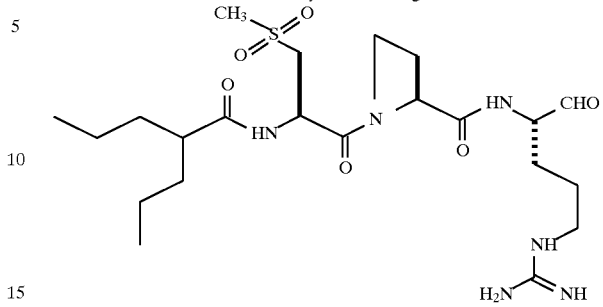

The title compound is prepared in the same manner as described in Example 8.

The compound of Example 105 is attached to the resin of Example 7. The title compound is cleaved from the resin as a protected semicarbazone. The semicarbazone is hydrolyzed to give the title compound. 0.1 mL of thiocresol is additionally added to the anisole-HF cleavage mixture.

Example 107

Preparation of N—Boc—S-(t-butyl acetate)-L-cysteine-L-2-azetidinecarboxylic acid-O-benzyl ester

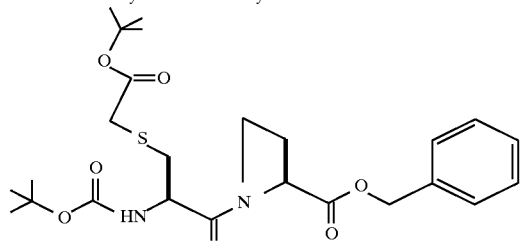

The compound of Example 51 (31.89 g, 95.06 mmole) and the compound of 80 (95.06 mmole) are suspended in 140 mL of acetonitrile and 120 mL of DMF at 0° C., then BOP (42.0 g, 95.06 mmole) and NMM (28.84 g, 285.18 mmole) are added.

The ice bath is removed after 30 minutes and the reaction is stirred for 18 hours at room temperature. The acetonitrile is evaporated under vacuum to give residue which is taken up in ethyl acetate (200 mL) and washed successively with 1N hydrochloric acid (1×50 mL), saturated sodium bicarbonate (1×50 mL) and brine (1×50 mL). The solution is dried with MgSO$_4$ and evaporated under vacuum to give crude product.

The crude product is purified by column chromatography on silica gel to give the title compound.

Example 108

Preparation of N—Boc—S-(t butyl acetate)-L-cysteine sulfone-L-2-azetidinecarboxylic acid-O-benzyl ester

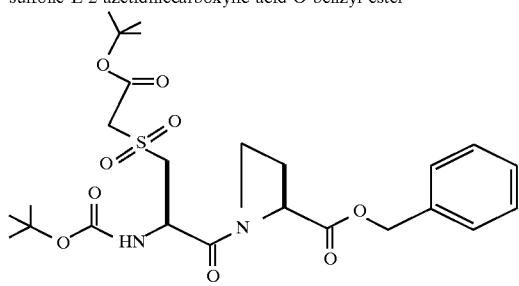

The compound of Example 107 (55.07 mmole) is dissolved in 300 mL of glacial acetic acid, sodium perborate tetrahydrate (42.36 g, 275.35 mmole) is added and the mixture is heated to 55° C. After 2.5 hours at this temperature, the reaction mixture is diluted with 1 liter of brine, the aqueous layer is extracted with ethyl acetate (4×250 mL) and the combined organic extracts are dried with $MgSO_4$. The solution is filtered and evaporated under vacuum, then is repeatedly azeotroped with toluene (200 mL) under vacuum to remove acetic acid. The residue is dissolved in ethyl acetate (200 mL), filtered and the filtrate is evaporated to give the title compound.

Example 109

Preparation of N-benzylsulfonyl-S(t-butyl acetate)-L-cysteine sulfone-L-2-azetidinecarboxylic acid-O-benzyl ester

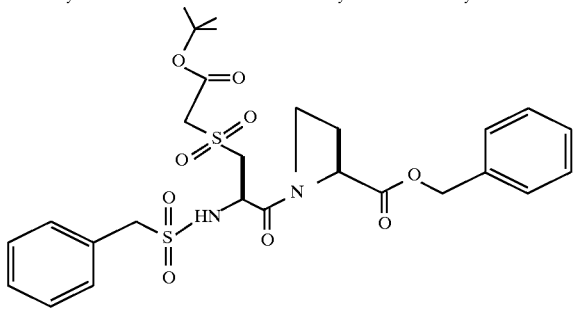

A solution of the compound of Example 108 (9.28 mmole) in 105 mL of sieve-dried ethyl acetate is prepared. To this, 26 mL of 5.7N anhydrous hydrochloric acid/ethyl acetate (that is generated in situ from acetyl chloride and methanol) is added. This mixture is stirred for several hours at room temperature until all starting material is consumed. The mixture is evaporated under vacuum and the residue is dissolved in acetonitrile and then this solvent is removed under vacuum. This is done three times to give a further residue.

The residue is suspended in 35 mL of acetonitrile, cooled to ice bath temperature, then benzylsulfonyl chloride (2.12 g, 11.14 mmole) and pyridine (2.93 g, 37.12 mmole) are added. The reaction is removed from the ice bath after 30 minutes and allowed stirred at room temperature for 18 hours. The acetonitrile is evaporated under vacuum to give a residue which is taken up in ethyl acetate (200 mL) and washed successively with 1N hydrochloric acid (1×50 mL), saturated sodium bicarbonate (1×50 mL) and brine (1×50 mL). The solution is dried with $MgSO_4$ and evaporated under vacuum to give crude product.

The crude product is purified by column chromatography on silica gel to give the title compound.

Example 110

Preparation of N-benzylsulfonyl-S-(t-butyl acetate)-L-cysteine sulfone-L-2-azetidinecarboxylic acid

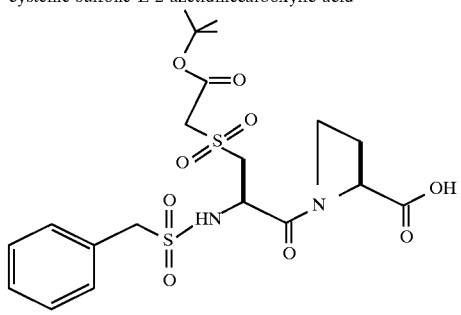

The compound of Example 109 (4.81 mmole) is dissolved in THF (50 mL), 0.5 g of 10% palladium on carbon is added and the mixture is stirred under hydrogen gas at atmospheric pressure for 18 hours.

After the catalyst is filtered off the reaction mixture, the solvent is removed under vacuum and the residue is taken up in a solution of saturated sodium bicarbonate. This solution is then extracted with ethyl acetate (1×150 mL) and the organic layer is decanted off. The remaining aqueous layer is layered with 100 mL of ethyl acetate and acidified with 1N hydrochloric acid to pH 2 (pH papers). After the phases separate, the organic layer is saved and the aqueous layer is then further extracted with ethyl acetate (3×100 mL).

The organic extracts are combined and washed with brine, dried with $MgSO_4$, filtered and evaporated under vacuum to give the title compound.

Example 111

Preparation of N-benzylsulfonyl-S-(carboxymethyl)-L-cysteine sulfone-L-2-azetidinecarboxylic acid-L-argininal

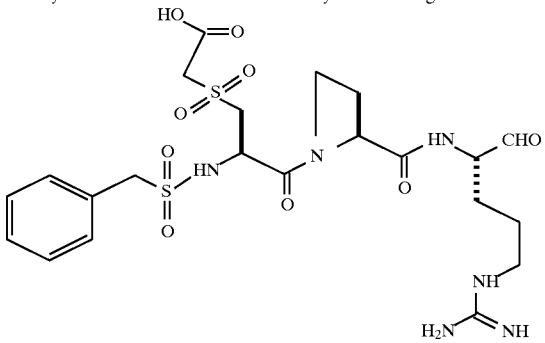

The title compound is prepared in the same manner as described in Example 8.

The compound of Example 110 is attached to the resin of Example 7. The title compound is cleaved from the resin as a protected semicarbazone. The semicarbazone is hydrolyzed to give the title compound.

Example 112

Preparation of N-(2-propylpentanoyl)-S-(t-butyl acetate)-L-cysteine sulfone-L-2-azetidinecarboxylic acid-O-benzyl ester

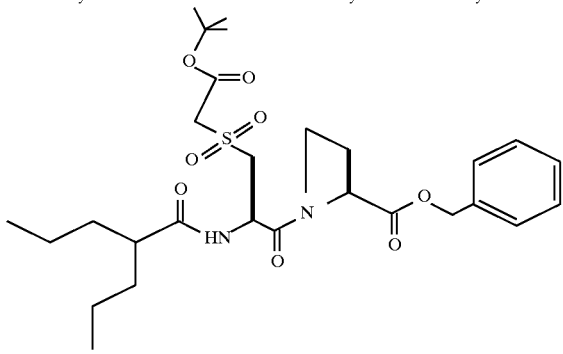

A solution of the compound of Example 108 (9.28 mmole) in 105 mL of sieve-dried ethyl acetate is prepared. To this, 26 mL of 5.7N anhydrous hydrochloric acid/ethyl acetate (that is generated in situ from acetyl chloride and methanol) is added. This mixture is stirred for several hours at room temperature until all starting material is consumed. The mixture is evaporated under vacuum and the residue is dissolved in acetonitrile and then this solvent is evaporated under vacuum. This is done three times to give a further residue.

The residue is suspended in 35 mL of acetonitrile, cooled to ice bath temperature, then 2-propylpentanoic acid (1.60 g, 11.4 mmole), BOP (4.10 g, 9.28 mmole) and NMM (3.75 g, 37.1 mmole) are added. The reaction is removed from the ice bath after 30 minutes and is allowed stir at room temperature for 18 hours. The reaction mixture is reduced in volume under vacuum to a residue. The residue is taken up in 200 mL ethyl acetate, and is washed successively with 1N hydrochloric acid (1×50 mL) saturated sodium bicarbonate 1×50 mL) and brine (1×50 mL). After drying with $MgSO_4$, the solvent is evaporated under vacuum to give crude product.

The crude product is purified by column chromatography on silica gel to give the title compound.

Example 113

Preparation of N-(2-propylpentanoyl)-S-(t-butyl acetate)-L-cysteine sulfone-L-2-azetidinecarboxylic acid

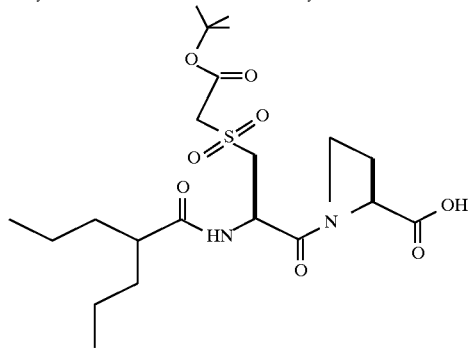

The compound of Example 112 (1.81 g, 3.2 mmole) is dissolved in THF (50 mL), 0.5 g of 10% palladium on carbon is added and the mixture is stirred under hydrogen gas at atmospheric pressure for 18 hours.

After the catalyst is filtered off the reaction mixture, the solvent is removed under vacuum and the residue is taken up in a solution of saturated sodium bicarbonate. This solution is then extracted with ethyl acetate (1×150 mL) and the organic layer is decanted off. The remaining aqueous layer is layered with 100 mL of ethyl acetate and acidified with 1N hydrochloric acid to pH 2 (pH papers). After the phases separate, the organic layer is saved and the aqueous layer is then further extracted with ethyl acetate (3×100 mL).

The organic extracts are combined and washed with brine, dried with $MgSO_4$, filtered and evaporated under vacuum to give the title compound.

Example 114

Preparation of N-(2-propylpentanoyl)-S-(carboxymethyl)-L-cysteine sulfone-L-2-azetidinecarboxylic acid-L-argininal

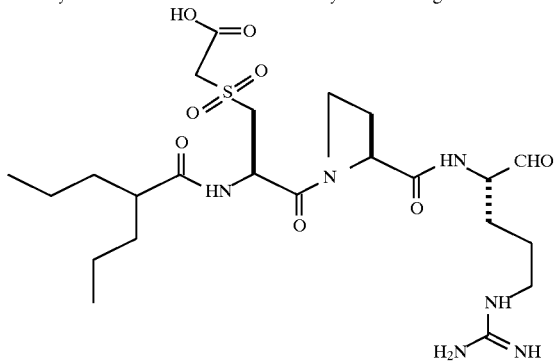

The title compound is prepared in the same manner as described in Example 8.

The compound of Example 113 is attached to the resin of Example 7. The title compound is cleaved from the resin as a protected semicarbazone. The semicarbazone is hydrolyzed to give the title compound.

Example 115

Preparation of N—Boc—S-(methyl acetate)-L-cysteine-L-2-azetidinecarboxylic acid-O-benzyl ester

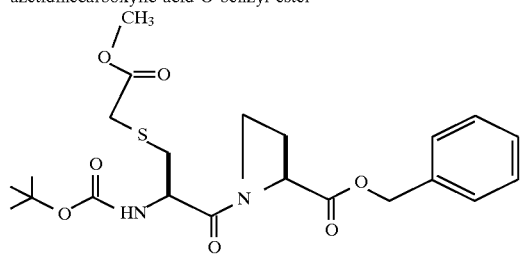

The compound of Example 61 (20.69 g, 70.5 mmole) and the compound of Example 80 (70.5 mmole) are suspended in 140 mL of acetonitrile at 0° C., then BOP (30.96 g, 70.5 mmole) and NMM (21.2 g, 211 mmole) are added. The ice bath is removed after 30 minutes and the reaction is stirred for 18 hours at room temperature. The reaction mixture is reduced in volume at 25° C. under vacuum to give a residue. The residue is taken up in 200 mL ethyl acetate, and is washed successively with 1N hydrochloric acid (1×50 mL) saturated sodium bicarbonate 1×50 mL) and brine (1×50 mL). After drying with $MgSO_4$, the solvent is evaporated under vacuum to give crude product.

This crude product is purified by column chromatography on silica gel to give the title compound.

Example 116

Preparation of N—Boc—S-(methyl acetate)-L-cysteine sulfone-L-2-azetidinecarboxylic acid-O-benzyl ester

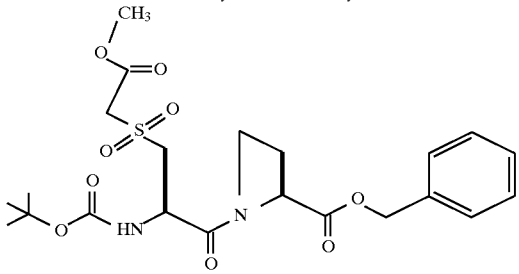

The compound of Example 115 (31.55 mmole) is dissolved in 165 mL of glacial acetic acid, sodium perborate tetrahydrate (24.27 g, 157.75 mmole) is added and the mixture is heated to 55° C. After 2.5 hours at this temperature, the reaction solution is diluted with 700 mL of brine, the aqueous layer is extracted with ethyl acetate (3×250 mL) and the combined organic phases are dried with MgSO$_4$. The solution is filtered and evaporated under vacuum, then is repeatedly azeotroped with toluene (200 mL) under vacuum to remove acetic acid. The residue is dissolved in ethyl acetate (200 mL), filtered and the filtrate is evaporated under vacuum to give the title compound.

Example 117

Preparation of N-(2-naphthylenesulfonyl)-S-(methyl acetate)-L-cysteine sulfone-L-2-azetidinecarboxylic acid-O-benzyl ester

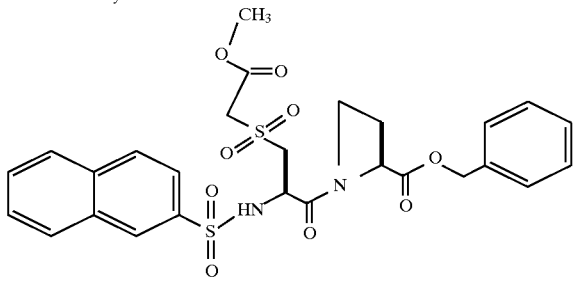

The compound of Example 116 (4.8 g, 9.37 mmole) is dissolved in 18 mL of 4N anhydrous hydrochloric acid/dioxane. The solution is stirred for several hours at room temperature until all starting material is consumed. The hydrochloric acid/dioxane solution is evaporated under vacuum to give a residue. The residue is dissolved in acetonitrile and evaporated under vacuum. This is done three times to give a further residue.

The residue is suspended in 35 mL of acetonitrile, cooled to ice bath temperature, then 2-naphthylenesulfonyl chloride (2.55 g, 11.2 mmole) and pyridine (2.2 g, 28.1 mmole) are added. The reaction is taken from the ice bath after 30 minutes and stirred at room temperature for 18 hours. The residue is taken up in 200 mL ethyl acetate, and is washed successively with 1N hydrochloric acid (1×50 mL) saturated sodium bicarbonate 1×50 mL) and brine (1×50 mL). After drying with MgSO$_4$, the solvent is evaporated under vacuum to give crude product.

The crude product is purified by column chromatography on silica gel to give the title compound.

Example 118

Preparation of N-(2-naphthylenesulfonyl)-S-(methyl acetate)-L-cysteine sulfone-L-2-azetidinecarboxylic acid

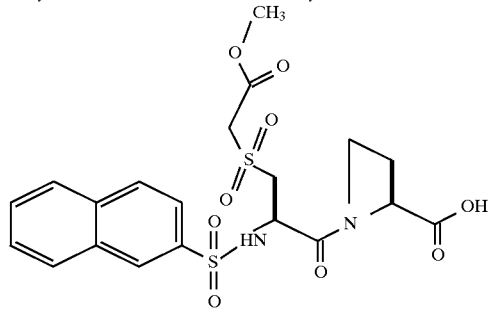

The compound of Example 117 (6.47 mmole) is dissolved in THF (50 mL), 0.5 g of 10% palladium on carbon is added and the mixture is stirred under hydrogen gas at atmospheric pressure for 18 hours.

After the catalyst is filtered off the reaction mixture, the solvent is removed under vacuum and the residue is taken up in a solution of saturated sodium bicarbonate. This solution is then extracted with ethyl acetate (1×150 mL) and the organic layer is decanted off. The remaining aqueous layer is layered with 100 mL of ethyl acetate and acidified with 1N hydrochloric acid to pH 2 (pH papers). After the phases separate, the organic layer is saved and the aqueous layer is then further extracted with ethyl acetate (3×100 mL).

The organic extracts are combined and washed with brine, dried with MgSO$_4$, filtered and evaporated under vacuum to give the title compound.

Example 119

Preparation of N-(2-naphthylenesulfonyl)-S-(methyl acetate)-L-cysteine sulfone-L-2-azetidinecarboxylic acid-L-argininal

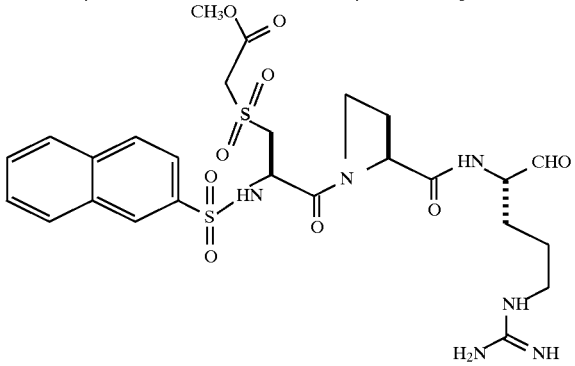

The title compound is prepared in the same manner as described in Example 8.

The compound of Example 118 is attached to the resin of Example 7. The title compound is cleaved from the resin as a protected semicarbazone. The semicarbazone is hydrolyzed to give the title compound.

Example 120

Preparation of N-benzylsulfonyl-S-(methyl acetate)-L-cysteine sulfone-L-2-azetidinecarboxylic acid-O-benzyl ester

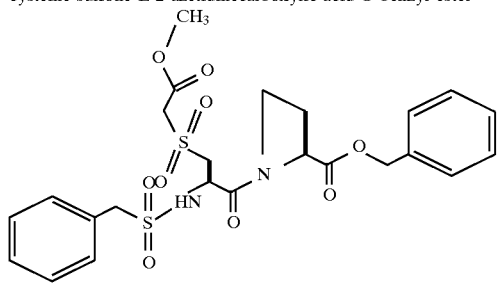

The compound of Example 116 (10.9 mmole) is dissolved in 18 mL of 4N anhydrous hydrochloric acid/dioxane. The solution is stirred for several hours at room temperature until all starting material is consumed. The hydrochloric acid/dioxane solution is evaporated under vacuum to give a residue. The residue is dissolved in acetonitrile and evaporated under vacuum. This is done three times to give a further residue.

The residue is suspended in 25 mL of acetonitrile, cooled to ice bath temperature, then benzylsulfonyl chloride (2.5 g, 13.1 mmole) and pyridine (2.6 g, 32.8 mmole) are added. The reaction is taken from the ice bath after 30 minutes and stirred at room temperature for 18 hours. The reaction mixture is reduced in volume under vacuum to a residue. The residue is taken up in 200 mL ethyl acetate, and is washed successively with 1N hydrochloric acid (1×50 mL) saturated sodium bicarbonate 1×50 mL) and brine (1×50 mL). After drying with MgSO$_4$, the solvent is evaporated under vacuum to give crude product.

The crude product is purified by column chromatography on silica gel to give the title compound.

Example 121

Preparation of N-benzylsulfonyl-S-(methyl acetate)-L-cysteine sulfone-L-2-azetidinecarboxylic acid

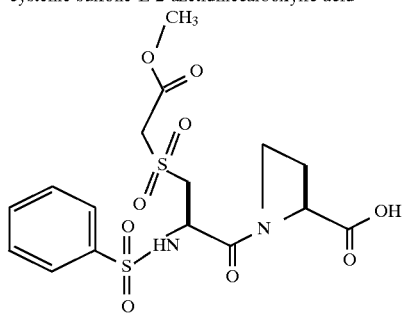

The compound of Example 120 (5.12 mmole) is dissolved in THF (50 mL), 0.5 g of 10% palladium on carbon is added and the mixture is stirred under hydrogen gas at atmospheric pressure for 18 hours.

After the catalyst is filtered off the reaction mixture, the solvent is removed under vacuum and the residue is taken up in a solution of saturated sodium bicarbonate. This solution is then extracted with ethyl acetate (1×150 mL) and the organic layer is decanted off. The remaining aqueous layer is layered with 100 mL of ethyl acetate and acidified with 1N hydrochloric acid to pH 2 (pH papers). After the phases separate, the organic layer is saved and the aqueous layer is then further extracted with ethyl acetate (3×100 mL).

The organic extracts are combined and washed with brine, dried with MgSO$_4$, filtered and evaporated under vacuum to give the title compound.

Example 122

Preparation of N-benzylsulfonyl-S-(methyl acetate)-L-cysteine sulfone-L-2-azetidinecarboxylic acid-L-argininal

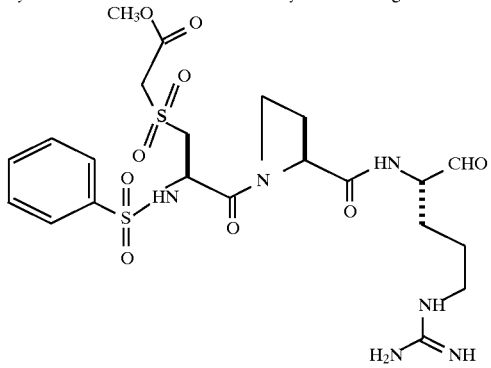

The title compound is prepared in the same manner as described in Example 8.

The compound of Example 121 is attached to the resin of Example 7. The title compound is cleaved from the resin as a protected semicarbazone. The semicarbazone is hydrolyzed to give the title compound.

Example 123

Preparation of N-alpha-t-butoxycarbonyl-N$^g$-nitro-L-arginine lactam.

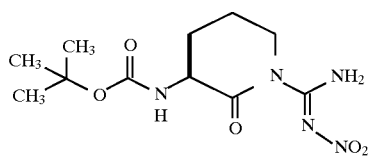

N-alpha-t-butoxycarbonyl-N$^g$-nitroarginine (2.00 g, 6.3 mmole) was dissolved in tetrahydrofuran (100 mL) by heating the solution to 50° C. The solution was allowed to cool to room temperature. N-methylpiperidine (0.84 mL, 6.9 mmole) was added, and the solution was cooled in an ice bath. Isobutylchloroformate (0.83 mL, 6.3 mmole) was added, and the reaction mixture was stirred at 0° C. for 6 hours. The reaction mixture was stirred for 18 hours while the ice in the dewar was allowed to melt overnight. The solvent was removed under vacuum. The crude product was dissolved in 20% ethyl acetate/dichloromethane (10 mL), and was purified by flash chromatography through a 3×5 cm column of silica gel using 20% ethyl acetate/dichloromethane as eluent. 125 mL of eluent was collected. The solvent was removed under vacuum to afford 1.39 g (74% crude yield) of the title compound as a white foam. Rf=0.44 (silica gel, 95:5, dichloromethane:isopropanol). Isobutanol was present as an impurity. This compound may be further purified by recrystallization from dichloromethane/hexanes or ethanol/water.

Example 124

Preparation of N-alpha-t-butoxycarbonyl-N$^g$-nitro-L-argininal.

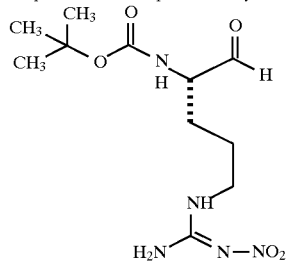

(a) Procedure 1

To a stirred solution of LiAlH$_4$ in tetrahydrofuran (3.8 mL of a 1.0M solution, 3.8 mmole), cooled in an ice bath, was added dropwise ethyl acetate (0.43 mL, 3.8 mmole) in tetrahydrofuran (5 mL). The solution was stirred for 30 minutes at 0° C. to preform LiAlH$_2$(OEt)$_2$.

The solution of this LiAlH$_2$(OEt)$_2$ was added dropwise to a stirred solution of compound of Example 123 (0.92 g, 3.1 mmole) in tetrahydrofuran (5 mL). After 30 minutes, the reaction was quenched with 1.0N aqueous hydrochloric acid/tetrahydrofuran (2 mL of a 1:1 mixture). 1.0N aqueous hydrochloric acid (20 mL) was added, and the solution was extracted three times with ethyl acetate (20 mL each). The combined organic layers were washed with water (5 mL), saturated sodium bicarbonate (5 mL) and twice with brine (2×5 mL), dried over anhydrous magnesium sulfate, filtered and the solvent was removed under vacuum to give 0.94 g (100% yield) of the title compound as an off-white solid.

(b) Procedure 2

Alternatively, the title compound was made by the procedures which follow.

(i) Preparation of N-alpha-t-butoxycarbonyl-N$^g$-nitro-L-arginine-(N,O-dimethyl)hydroxylamide A 12 liter four-necked round bottom flask equipped with an overhead stirring apparatus was flame dried under a strong stream of nitrogen. After the flask had cooled, 120.0 g of N-alpha-t-butoxycarbonyl-N$^g$-nitro-L-arginine (376 mmole, 1 equivalent) was added under a blanket of nitrogen followed by the addition of 6 liters of anhydrous tetrahydrofuran (Aldrich sure-seal) via cannula. The flask was then fitted with a thermometer and the resulting suspension was warmed to 50° C. with a heat gun while stirring. The reaction mixture was cooled to 5° C. with an ice bath and further cooled to -5° C. with an ice/acetone bath.

During the time it took for this solution to reach -50° C., 36.66 g of N,O-dimethylhydroxylamine hydrochloride (376 mmole, 1.0 equivalent) was weighed out in a 500 mL flask and suspended in 300 mL of dichloromethane. This suspension was sparged with nitrogen for 5 minutes, cooled to 0° C. and 46 mL of N-methylpiperidine (1.0 equivalent) was added via syringe under nitrogen. The mixture was sonicated briefly to insure complete dissolution/free base formation and recooled to 0° C. in an ice bath while still under nitrogen. The resulting solution of free base was used later.

When the above arginine solution had reached -5° C., 45 mL of N-methylpiperidine was added via syringe followed 5 minutes later by the addition of 46 mL of isobutyl chloroformate (0.95 equivalent) via syringe. The resulting solution was stirred for 15 minutes at -5° C. After this time, the free base solution of N,O-dimethylhydroxylamine generated above was added via cannula over about 15 minutes. Stirring was continued at -5° C. for another 1.5 hours at which time thin layer chromatography (silica gel, 1:10:90 acetic acid/methanol/dichloromethane) indicated that the reaction was complete. The reaction mixture was filtered while still cold, the salts washed with 400 mL of cold tetrahydrofuran and the filtrate concentrated under vacuum on a rotary evaporator to yield a yellow foam.

The crude intermediate was taken up in 300 mL of dichloromethane and applied to a column of silica gel (70–230 mesh, 7×50 cm). The column was first eluted with 2 liters of dichloromethane followed by 2 liters of 2% methanol in dichloromethane. This was followed by elution with 5% methanol in dichloromethane until all of the product had been eluted (the eluent was checked for UV activity and five one-liter fractions were collected once this UV activity was apparent). Fractions containing pure product were pooled and concentrated under vacuum and placed under a high vacuum overnight to yield 120.1 g (88% yield) of N-alpha-t-butoxycarbonyl-N$^g$-nitro-L-arginine-(N,O-dimethylhydroxylamide) as a light yellow foam. This foam was taken up in 300 mL of dichloromethane, 300 mL of toluene, and the volatiles were once again removed under vacuum to remove any residual water or methanol.

(ii) Preparation of N-alpha-t-butoxycarbonyl-N$^g$-nitro-L-argininal 120.1 g of N-alpha-t-butoxycarbonyl-N$^g$-nitro-L-arginine-(N,O-dimethylhydroxylamide) (the product of Step (i)) (331.4 mmole) was taken up in 2.8 liters of dry (Aldrich sure-seal) tetrahydrofuran and transferred to a dry 5 liter 4-necked round bottom flask equipped with a mechanical stirrer and a low temperature thermometer. The solution was cooled to -70° C. with a dry ice/acetone bath and 300 mL of 1M LiAlH$_4$ in tetrahydrofuran was added by cannula transfer directly from 100 mL Aldrich sure-seal bottles. An additional 50 mL of 1M LiAlH$_4$ in tetrahydrofuran was added via syringe (total 331 mL). During the additions, the reaction temperature was kept below -60° C. The reaction was stirred for 0.5 hours at -70° C., the cooling bath removed, and the reaction was slowly allowed to warm to 0° C. (about 2.5 hours). Between -30° C. and -20° C. a thick slurry resulted. When the reaction mixture obtained 0° C., a small aliquot was removed and partitioned between ethyl acetate/2M potassium bisulfate. The organic layer was then analyzed by thin layer chromatography (silica gel, ethyl acetate).

When the reaction was judged to be complete, it was cooled to -70° C. and 503 mL of 2M potassium bisulfate was added via dropping funnel at a slow enough rate to keep the reaction temperature below -30° C. The cooling bath was removed and the reaction mixture was allowed to come to 0° C. over the course of 2 hours at which time a white precipitate was filtered off. The solids were washed with 500 mL of cold tetrahydrofuran. The filtrate was concentrated under vacuum on a rotary evaporator until most of the tetrahydrofuran was removed and the remaining white sludge was mostly aqueous. The crude product was taken up in 1.5 liters of ethyl acetate and washed with 0.2M hydrochloric acid (2×200 mL). The hydrochloric acid extracts were back-extracted with 400 mL of ethyl acetate and the organics were combined and extracted with saturated sodium bicarbonate (2×200 mL). The bicarbonate extracts were also back-extracted with 400 mL of ethyl acetate. The organics were then combined and washed with brine (200 mL) followed by drying over anhydrous sodium sulfate. The solution was filtered, concentrated under vacuum on a rotary evaporator and placed on a high vacuum overnight to yield a white solid (89.0 g) of crude title compound. This was chromatographed on silica gel and eluted with a gradient of 0 to 10% methanol in dichloromethane. The pure fractions were combined and evaporated to yield the title compound as a white solid (75 g, 74%).

Example 125

Preparation of N-alpha-t-butoxycarbonyl-N$^g$-nitro-L-argininal ethyl cyclol.

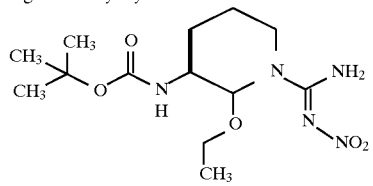

(a) Preparation A

N-alpha-t-butoxycarbonyl-N$^g$-nitro-L-argininal (Compound of Example 124) (41.60 g, 0.137 mole) was dissolved in ethanol (200 mL) and concentrated hydrochloric acid (1 mL) was added. After the reaction was complete by TLC (silica gel, 10% methanol in dichloromethane), the solvent was removed under vacuum. The crude product was purified by flash chromatography through a column of silica gel (230–400 mesh) using 0–10% ethyl acetate/dichloromethane as eluent. The combined fractions yielded 36.88 g (81%) of the title compound as pale yellow foam. R$_f$=0.62 (silica gel, 95:5, CH$_2$Cl$_2$:methanol).

(b) Preparation B

To a solution of N-alpha-t-butoxycarbonyl-N$^g$-nitro-L-argininal (the Compound of Example 124) (170 g., 0.561 mole) and 3 liters absolute ethanol, was added 3 mL concentrated hydrochloric acid. The reaction mixture was stirred overnight at 25° C. The solvent was removed under vacuum; the resulting solid was chromatographed on silica gel (70–239 mesh) and with a slow gradient of methylene chloride/ethyl acetate, 100:0 to 85:15. The pure fractions were combined and evaporated under vacuum to yield a white foam of N$^g$-nitro-L-argininal ethyl cyclol (100.48 g. 64%) and 58.20 g. of fixed fractions having small impurities. The TLC of the pure compound showed the expected 2 isomeric products in methylene chloride/ethyl acetate 85:15.

Example 126

Preparation of N$^g$-nitro-L-argininal ethyl cyclol, trifluoroacetate salt

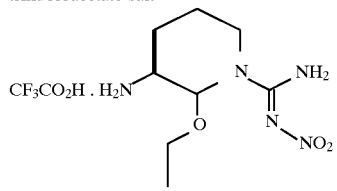

A portion of N$^g$-nitro-L-argininal ethyl cyclol (the Compound of Example 125 (1.26 g) was treated with 50% trifluoroacetic acid/dichloromethane (10 mL) for 35 minutes. The solution was added dropwise to diethyl ether (100 mL) while swirling. The resulting precipitate was filtered and washed with diethyl ether. The light yellow powder was dried under vacuum to yield (1.20g, 91%) of the title compound.

Example 127

Preparation of N$^g$-nitro-L-argininal ethyl cyclol, hydrochloride salt.

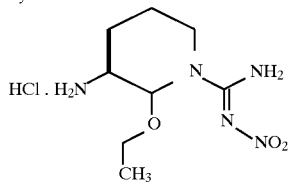

To a solution of N$^g$-nitro-L-argininalethyl cyclol (the Compound of Example 125) (35 g) in 500 mL of absolute ethanol at 0° C. was added slowly 500 mL of absolute ethanol saturated with HCl(g). This mixture was allowed to warm to 25° C. and progress of the reaction was checked by thin-layer chromatography. The appearance of a very polar product was the desired compound. Most of the HCl acid was removed with a stream of dry nitrogen and the organic solvent was removed under vacuum. The resulting 33 g of the title compound as a yellow-white solid was used without further purification.

Example 128

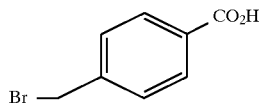

A 500 mL carbon tetrachloride solution of commercially available (Aldrich) p-toluic acid (20.0 g, 146.9 mmole) and AIBN (110 mg, a catalytic amount) was refluxed for 3 hours while exposed to a 250 watt Philips® heat lamp. The carbon tetrachloride was evaporated under vacuum to give crude product. The crude product was used without further purification to synthesize the compound of Example 129. NMR analysis indicates that the starting material was almost completely consumed (>95%). Thin layer chromatography analysis of the title compound showed a spot at Rf=0.34 (silica, 95:5:1 dichloromethane/methanol/acetic acid).

Example 129

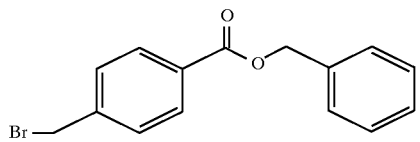

The crude material from Example 128 (50 g total, containing approximately 34 g of product, 158 mmole) was dissolved in 525 mL of tetrahydrofuran, then dicyclohexylcarbodiimide (35.9 g, 173.8 mmole), 4-dimethylaminopyridine (5.8 g, 47.4 mmole) and benzyl alcohol (51.3 g, 474 mmole) were added. The reaction was stirred for 18 hr. at room temperature. The resulting slurry was filtered and the tetrahydrofuran evaporated under vacuum.

The crude product was purified by column chromatography on silica gel, eluting with 40:60 ethyl acetate/hexane to yield 19.8 g (44.2% yield) of a white solid. Thin layer chromatography analysis of the title compound showed a single spot at Rf=0.73 (silica, 40:60 ethyl acetate/hexane).

Example 130

Preparation of S-(p-toluic acid-O-benzyl ester)-L-cysteine

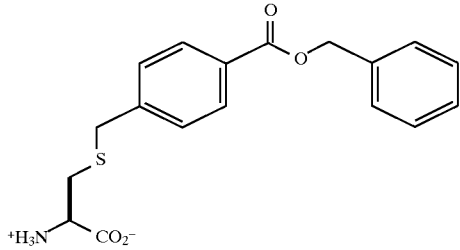

A 90 mL aqueous solution of commercially available (Aldrich) L-cysteine hydrochloride monohydrate (11.4 g, 64.9 mmole) and sodium hydroxide (5.19 g, 129.8), at room temperature, was treated with a solution of p-bromo toluic acid-O-benzyl ester (19.8 g, 64.9 mmole) in 170 mL of dioxane over 30 minutes. The reaction was stirred for 3 days at room temperature during which time a thick precipitate formed. The solid was filtered off, washed with 2:1 dioxane/water and dried under high vacuum at 40° C. to give 17.8 g (78.9% crude yield includes occluded salt) of the title compound.

Example 131

Preparation on N-Boc-S-(p-toluic acid-O-benzyl ester)-L-cysteine

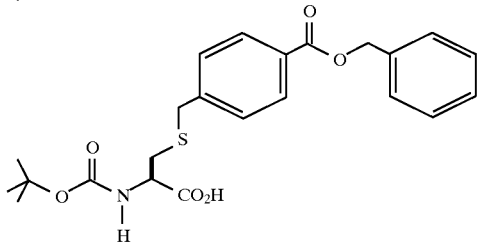

The compound of Example 130 (17.4 g, 50.1 mmole) was suspended in 70 mL of saturated sodium bicarbonate/30 mL of deionized water. A solution of di-tert-butyl dicarbonate (11.2 g, 51.4 mmole) in 125 mL of dioxane was added and the slurry stirred for 2 days at room temperature.

The slurry was extracted with diethyl ether (2×100 mL). The slurry was layered with ethyl acetate (200 mL) and acidified with 3N hydrochloric acid to pH 2 (as measured by pH paper). The resulting organic layer was saved and the remaining aqueous layer was further extracted with ethyl acetate (2×200 mL). The organic extracts were combined, washed with brine, dried with MgSO$_4$ and the solvent evaporated under vacuum to yield 19.0 g (84.6% yield) of the title compound as a clear oil. Thin layer chromatography analysis of the title compound showed a single spot with Rf=0.30 (silica, 95:5:1 dichloromethane/methanol/acetic acid).

Example 132

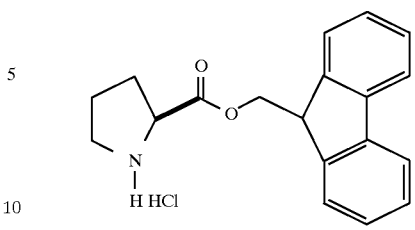

A 850 mL dichloromethane solution containing Boc-L-proline (49.8 g, 231.5 mmole) was treated with carbonyldiimidazole (37.5 g, 231.5 mmole) and stirred for 45 minutes at room temperature. The reagent 9-fluorenemethanol (50 g, 254.7 mmole) was added and the reaction stirred overnight at room temperature. The reaction solution was washed with 1N hydrochloric acid (1×350 mL), saturated sodium bicarbonate (1×350 mL) and brine (1×350 mL). The organic layer was dried with MgSO$_4$ and then filtered.

The organic layer was treated with 100 mL of 4N HCl in dioxane and stirred overnight at room temperature. Another 100 mL of 4N HCl in dioxane was added due to incomplete reaction, and stirred overnight at room temperature. The organic layer was concentrated under vacuum to a 200 mL volume, then layered with 400 mL of ethyl ether. The immiscible layers were stirred and the ether layer was decanted; this sequence was repeated twice more. Acetonitrile (100 mL) was added to the dichloromethane layer and the solvents were evaporated under vacuum to leave an oil. A semi-solid formed upon overnight standing. The solid was triturated with ethyl ether (3×150 mL), filtered and dried under vacuum to yield 63.6 g (83.3% yield) of the above-identified compound. NMR analysis was consistent with the desired product.

Example 133

Preparation of N—Boc—L-cysteine-S-(p-toluic acid-O-benzyl ester)-L-proline-FMOC

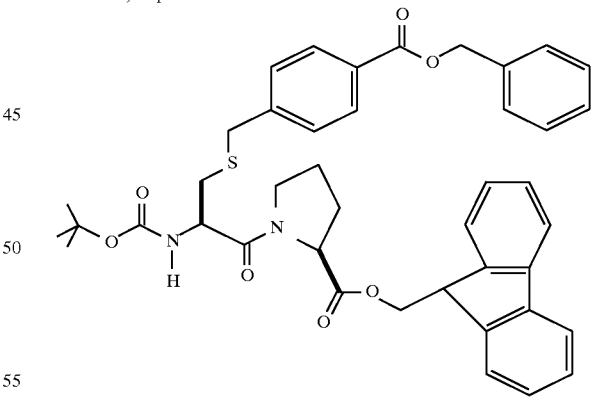

A 165 mL dimethylformamide solution containing the compound of Example 131 (18.4 g, 41.3 mmole) was treated with N-hydroxybenzotriazole (8.4 g, 62.0 mmole) and ethyl-3-(3-dimethylamino)-propyl carbodiimide hydrochloride (11.9 g, 62.0 mmole). After the reactants had dissolved, the reaction solution was charged with 2,4,6-collidine (25.0 g, 260.5 mmole) and L-proline-FMOC hydrochloride (13.6 g, 41.2 mmole) and stirred 18 hours at room temperature.

The reaction slurry was dissolved in 600 mL of ethyl acetate, then washed with 1N hydrochloric acid (1×200 mL), saturated sodium bicarbonate (1×200 mL) and brine (4×100 mL). The organic layer was dried with MgSO₄, filtered and evaporated under vacuum.

The crude product was purified by column chromatography on silica gel with 40:60 ethyl acetate/hexane to yield 15.5 g (52.0% yield) of a white foam. Thin layer chromatography analysis of the title compound showed a single spot with Rf=0.50 (silica, 40:60 ethyl acetate/hexane).

Example 134

Preparation of N—Boc—L-cysteine-S-sulfone-(p-(toluic acid-O-benzyl ester)-L-proline-FMOC

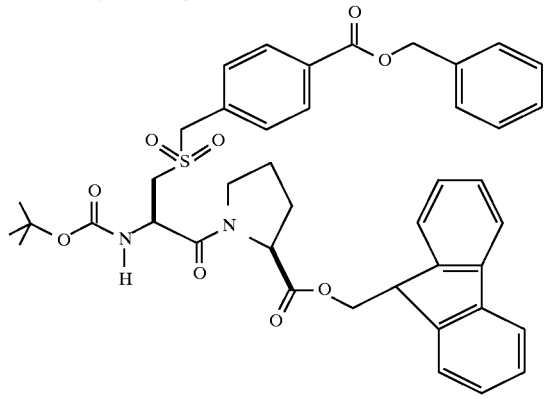

A bi-phasic solution of 40 mL carbon tetrachloride, 40 mL acetonitrile and 80 mL of deionized water containing the compound of Example 6 (14.6 g, 20.2 mmole) was treated with sodium periodate (13.0 g, 60.6 mmole) and ruthenium tri-chloride hydrate (0.03 g, 0.14 mmole). The mixture was stirred vigorously for 4 hours at room temperature.

The mixture was partitioned in water (600 mL) and ethyl ether (600 mL). The ether layer was washed with saturated sodium bicarbonate (150 mL), brine (150 mL), dried with MgSO₄ and evaporated under vacuum to yield 15.2 g (100% yield) of white solid. Thin layer chromatography analysis of the title compound showed a major spot with Rf=0.21 (40:60, ethyl acetate/hexane).

Example 135

Preparation of N-benzylsulfonamide-L-cysteine-S-sulfone-(p-toluic acid-O-benzyl ester)-L-proline-FMOC

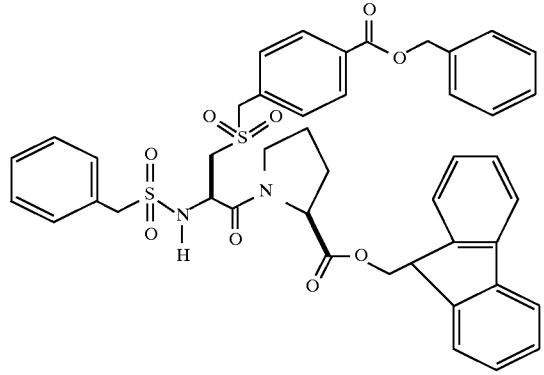

A solution of 5 mL of dichloromethane and 13 mL of 4N HCl in dioxane containing the compound of Example 134 (6.5 g, 8.6 mmole) was stirred at room temperature for 4 hours. The solvent was evaporated under vacuum, the residue was then evaporated from acetonitrile.

The amine hydrochloride salt was dissolved in 25 mL of dimethyl formamide/acetonitrile (1:2), cooled to 0° C. and charged with benzylsulfonyl chloride (2.0 g, 10.4 mmole) and 2,4,6-collidine (4.2 g, 34.5 mmole). The ice bath was taken away and the reaction was stirred for 3 days. The reaction mixture was reduced in volume at 25° C. to give an oil. The oil was dissolved in ethyl acetate (300 mL), then successively washed with 1N hydrochloric acid (1×100 mL), saturated sodium bicarbonate (1×100 mL) and brine (1×100 mL). The organic layer was dried with MgSO₄ and evaporated under vacuum to give crude product.

The crude product was purified by column chromatography on silica gel, eluting with 97:3 dichloromethane/ethyl acetate to yield 4.6 g (69.8% yield) of the title compound as a solid. Thin layer chromatography analysis of the title compound showed a single spot with Rf=0.50 (silica, 3:2 ethyl acetate/hexane).

Example 136

Preparation of N-benzylsulfonamide-L-cysteine-S-sulfone (p-toluic acid-O-benyl ester)-L-proline

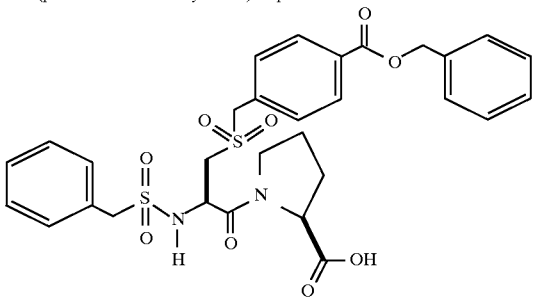

A 50 mL tetrahydrofuran solution containing the compound of Example 135 (4.05 g, 5.0 mmole) and piperidine (4.1 g, 48.0 mmole) was stirred at room temperature for 1.5 hours. The reaction was concentrated under vacuum and taken up in deionized water (70 ML). The aqueous layer was extracted with ethyl acetate (3×100 mL) to remove reaction side products, then layered with ethyl acetate (100 mL) and acidified to pH 2 (as measured by pH paper) with 3N hydrochloric acid. The ethyl acetate layer was removed and the aqueous layer was extracted with ethyl acetate (2×100 mL). The combined organic extract containing product was washed with brine (100 mL) and dried with MgSO₄. The ethyl acetate was removed under vacuum to yield 2.7 g (86.8% yield) of solid. Thin layer chromatography analysis of the title compound showed a single spot with Rf=0.50 (silica, 90:10:2 dichloromethane/methanol/acetic acid).

Example 137

Preparation of N-benzylsulfonamide-L-cysteine-S-sulfone (p-toluic acid-O-benzyl ester)-L-proline-nitro-cycloarginal (OEt)

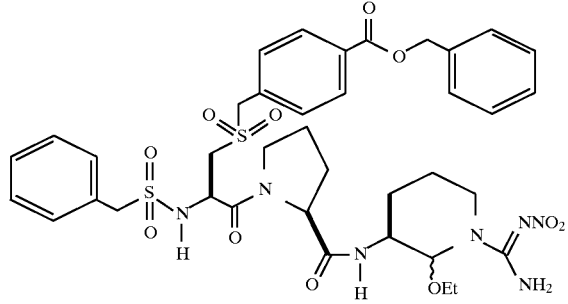

A 6.5 mL solution of DMF/acetonitrile (40:60) containing the compound of Example 136 (1.0 g, 1.6 mmole), HBTU (0.91 g, 2.4 mmole) and HOBT (0.33 g, 2.4 mmole) was stirred at 0° C. for 20 minutes, then charged with $N^g$-nitro-L-argininal ethyl cyclol hydrochloride (the compound of Example 127) (0.56 g, 2.1 mmole) and NMM (0.89 g, 8.8 mmole). The ice bath was removed and the reaction stirred for 2 days at room temperature.

The reaction mixture was reduced in volume at 25° C. to give an oil. The oil was dissolved in ethyl acetate (250 mL), then successively washed with 1N hydrochloric acid (1×50 mL), saturated sodium bicarbonate (1×50 mL) and brine (3×50 mL). The organic layer was dried with $MgSO_4$ and evaporated under vacuum to give crude product.

The crude product was purified by column chromatography on silica gel, eluting with 95:5 (dichloromethane/methanol) to yield 0.77 g (57% yield) of the title compound as a solid. Thin layer chromatography analysis of the title compound showed a single spot with Rf=0.36 (silica, 4/1/4 dichloromethane/methanol/hexane).

Example 138

Preparation of N-benzylsulfonamide-L-cysteine-S-sulfone (p-toluic acid)-L-proline-cycloarginal(OEt) TFA salt

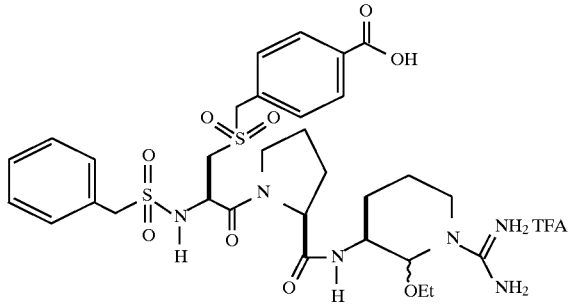

A 63 mL solution of methanol/water/acetic acid (50:10:3) containing the compound of Example 137 (0.74 g, 0.88 mmole) and 10% Pd/C catalyst (0.35 g) was hydrogenated on Parr shaker at 40 PSI hydrogen gas for 3 days at room temperature. At intermediate points, the reaction was filtered and charged with fresh catalyst. The slurry was filtered and concentrated under vacuum to a solid. The material was chromatographed by reverse phase HPLC (C-18, acetonitrile/0.1% TFA gradient) to remove impurities. The collected fractions of interest were pooled and lyophilized to yield 0.3 g (41.6% yield) of the above-identified compound as a white solid

Example 139

Preparation of N-benzylsulfonamide-L-cysteine-S-sulfone (p-toluic acid)-L-proline-arginal aldehyde.

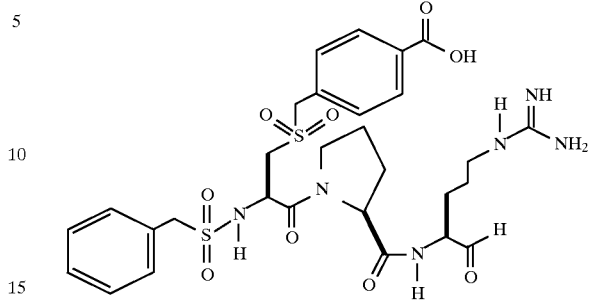

A 12 mL solution of acetonitrile/deionized water (50/50) cooled to 0° C. containing the compound of Example 138 (0.3 g, 0.37 mmole) was charged with 12 mL of cold 12N hydrochloric acid. The reaction was stirred at 0° C. for 30 minutes, then warmed to room temperature with a total stirring time of 4 hours. The reaction was cooled to 0° C. and quenched with 2.5M sodium acetate (100 mL) to pH 5 (as measured by pH paper). The title compound was isolated by reverse phase HPLC (C-18, acetonitrile/0.1% TFA) and recovered from the pooled fractions of interest by lyophilization. Fast atom bombardment mass spectrometry confirmed the theoretical molecular weight of 678.

Example 140

Preparation of N-2-propylpentylamide-L-cysteine-S-sulfone-(p-toluic acid-O-benzyl ester)-L-proline-FMOC

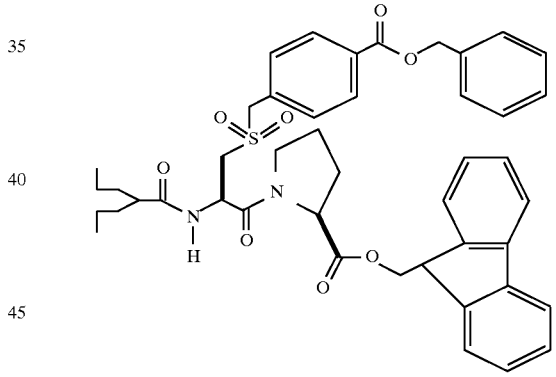

A solution of 5 mL of dichloromethane and 13 mL of 4N HCl in dioxane containing the compound of Example 134 (6.5 g, 8.6 mmole) was stirred at room temperature for 4 hours. The solvent was evaporated under vacuum, the residue was then evaporated from acetonitrile.

A 25 mL solution of dimethylformamide/acetonitrile (1:2) containing 2-propylpentanoic acid (1.86 g, 12.9 mmole) and BOP (3.8 g, 8.6 mmole) stirred at 0° C. for 30 minutes. The amine hydrochloride listed above was dissolved in a minimum amount of acetonitrile/DMF (about 5 mL) and added to the activated acid along with 2,4,6-collidine (4.2 g, 34.5 mmole). The ice bath was removed and the reaction was stirred at room temperature for 3 days. The reaction mixture was reduced in volume at 25° C. to give an oil. The oil was dissolved in ethyl acetate (300 mL), then successively washed with 1N hydrochloric acid (1×100 mL), saturated sodium bicarbonate (1×100 mL) and brine (1×100 mL). The organic layer was dried with $MgSO_4$ and evaporated under vacuum to give crude product.

The crude product was purified by column chromatography on silica gel, eluting with 65:35 hexane/ethyl acetate to yield 4.4 g (65.4% yield) of the title compound as a solid. Thin layer chromatography analysis of the title compound showed a single spot with Rf=0.52 (silica, 3:2 ethyl acetate/hexane).

Example 141

Preparation of N-2-propylpentylamide-L-cysteine-S-sulfone-(p-toluic acid-O-benzyl ester)-L-proline

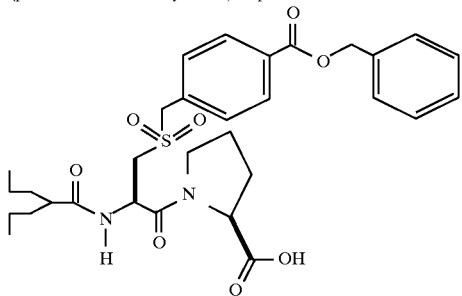

A 50 mL tetrahydrofuran solution containing the compound of Example 140 (4.0 g, 5.2 mmole) and piperidine (4.2 g, 49.5 mmole) was stirred at room temperature for 1.5 hours. The reaction was concentrated under vacuum and taken up in deionized water (70 mL). The aqueous layer was extracted with ethyl acetate (3×100 mL) to remove reaction side products, then layered with ethyl acetate (100 mL) and acidified to pH 2 (as measured by pH papers) with 3N hydrochloric acid. The ethyl acetate layer was removed and the aqueous layer was extracted with ethyl acetate (2×100 mL). The combined organic extract containing product was washed with brine (100 mL) and dried with MgSO$_4$. The ethyl acetate was removed under vacuum to yield 2.8 g (89.7% yield) of solid. Thin layer chromatography analysis of the title compound showed a single spot with Rf=0.50 (silica, 90:10:2 dichloromethane/methanol/acetic acid).

Example 142

Preparation of N-2-propylpentylamide-L-cysteine-S-sulfone (p-toluic acid-O-benzyl ester)-L-proline-nitro-cycloarginal(OEt)

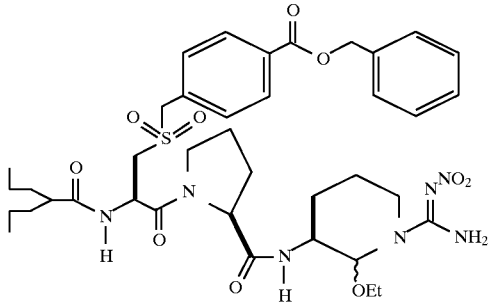

A 7.4 mL solution of DMF/acetonitrile (20:80) containing the compound of Example 141 (1.2 g, 3.0 mmole), HBTU (1.15 g, 3.0 mmole) and HOBT (0.41 g, 3.0 mmole) was stirred at 0° C. for 20 minutes then, charged with N$^g$-nitro-L-argininal ethyl cyclol hydrochloride (the compound of Example 127) (0.71 g, 2.6 mmole) and NMM (1.2 g, 11.6 mmole). The ice bath was removed and the reaction stirred for 2 days at room temperature. The reaction mixture was reduced in volume at 25° C. to give an oil. The oil was dissolved in ethyl acetate (250 mL), then successively washed with 1N hydrochloric acid (1×50 mL), saturated sodium bicarbonate (1×50 mL) and brine (3×50 mL). The organic layer was dried with MgSO$_4$ and evaporated under vacuum to give crude product.

The crude product was purified by column chromatography on silica gel, eluting with 4:1:4 dichloromethane/methanol/hexane to yield 1.3 g (79.9% yield) of the title compound as a solid. Thin layer chromatography analysis of the title compound showed a single spot with Rf=0.50 (silica 4:1:4 dichloromethane/methanol/hexane).

Example 143

Preparation of N-2-propylpentylamide-L-cysteine-S-sulfone-(p-toluic acid)-L-proline-cycloarginal(OEt) TFA salt

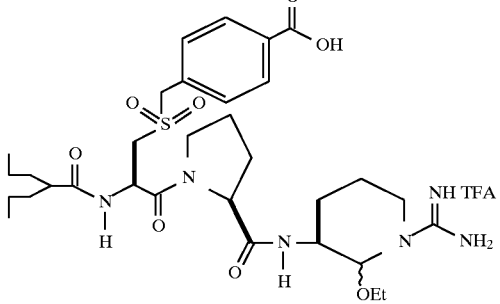

A 93 mL solution of methanol/water/acetic acid (75:15:3) containing the compound of Example 142 (1.3 g, 1.6 mmole) and 10% Pd/C catalyst (0.6 g) was hydrogenated on a Parr shaker at 40 PSI hydrogen gas for 10 days at room temperature. At intermediate points, the reaction was filtered and charged with fresh catalyst. The slurry was filtered and concentrated under vacuum to a solid. The material was chromatographed by reverse phase HPLC (C-18, acetonitrile/0.1% TFA gradient) to remove impurities. The collected fractions of interest were pooled and lyophilized to yield 0.12 g (15.1% yield) as a white solid.

Example 144

Preparation of N-2-propylpentylamide-L-cysteine-S-sulfone (p-toluic acid)-L-proline-arginal aldehyde

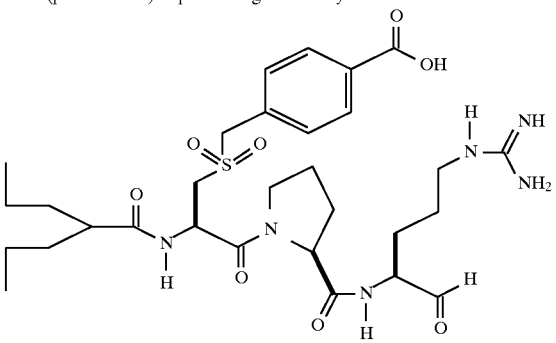

A 10 mL solution of acetonitrile/deionized water (50/50) cooled to 0° C. containing the compound of Example 143 (0.35 g, 0.44 mmole) was charged with 10 mL of cold 12 N hydrochloric acid. The reaction was stirred at 0° C. for 30 minutes, then warmed to room temperature with a total stirring time of 4 hours. The reaction was cooled to 0° C. and quenched with 2.5M sodium acetate (100 mL) to pH 5 (as measured by pH paper). The title compound was isolated by reverse phase HPLC (C-18, acetonitrile/0.1% TFA) and recovered from the pooled fractions of interest by lyophilization. Fast atom bombardment mass spectrometry confirmed the theoretical molecular weight of 650.

By following the procedures of the Example 1 to 122, the following compounds are made:
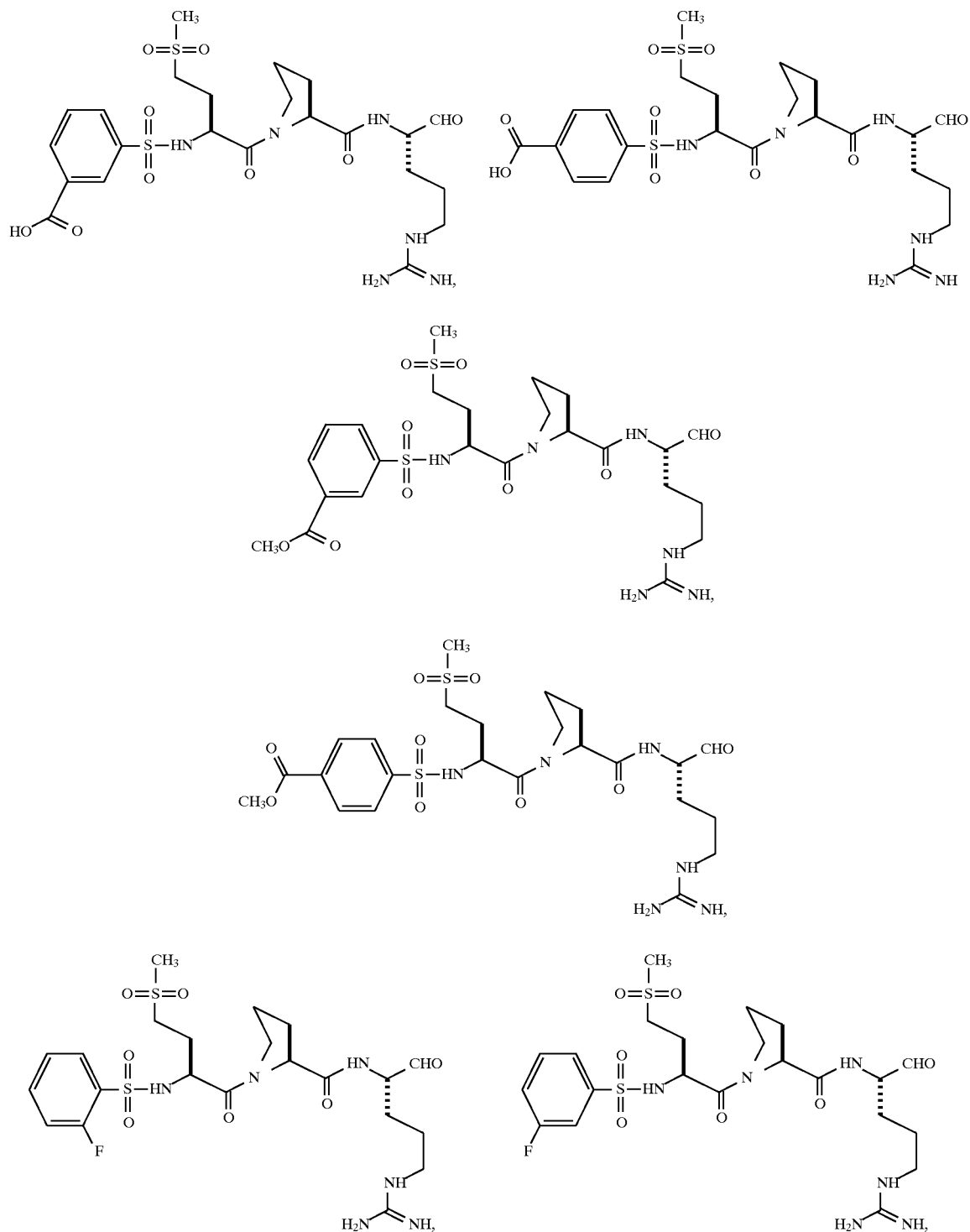

121
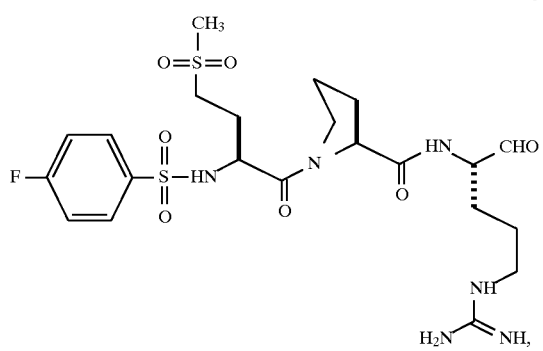
122
-continued
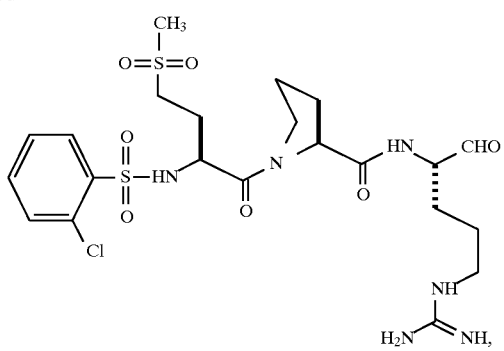
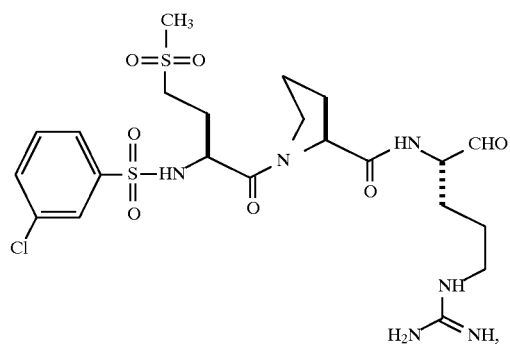
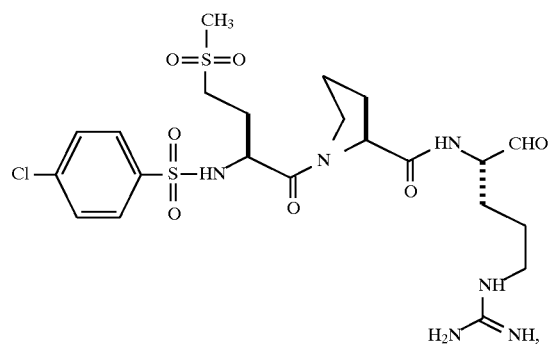
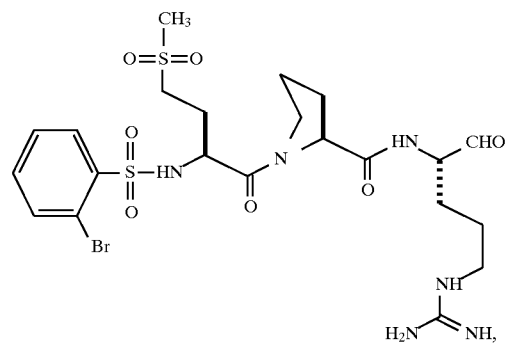
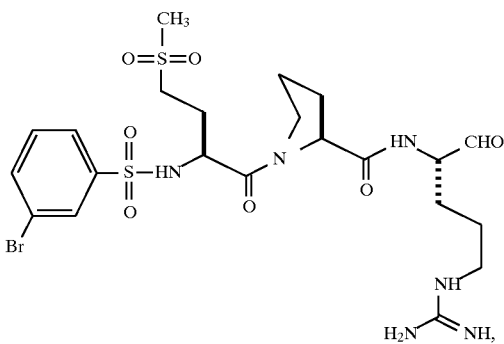
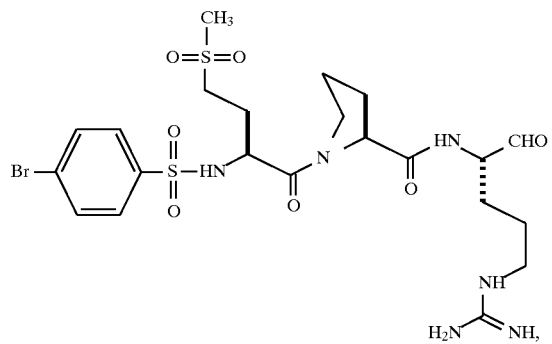
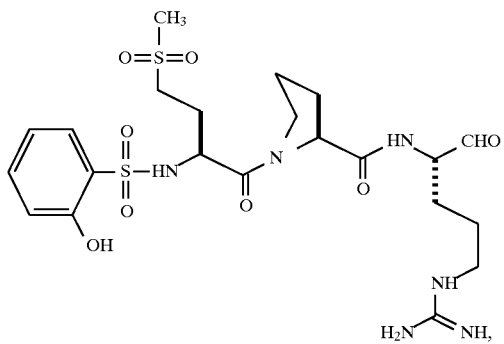

123 124
-continued
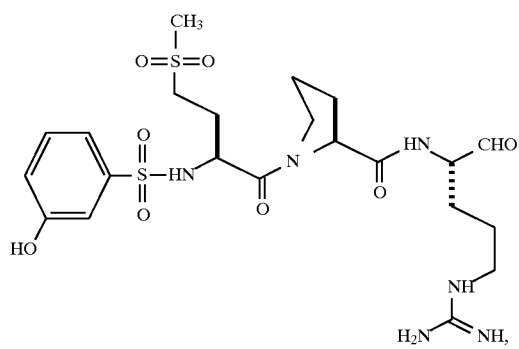 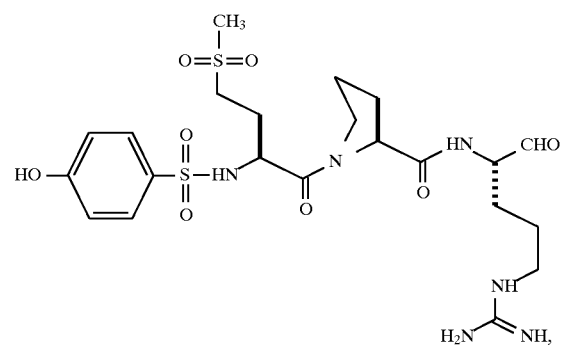
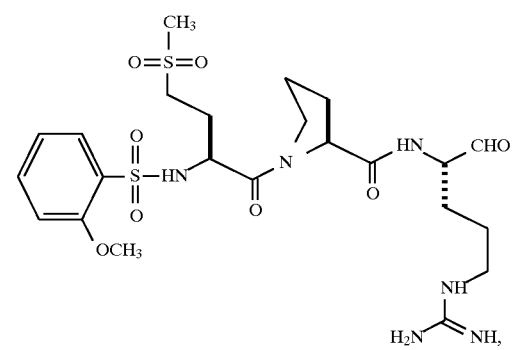 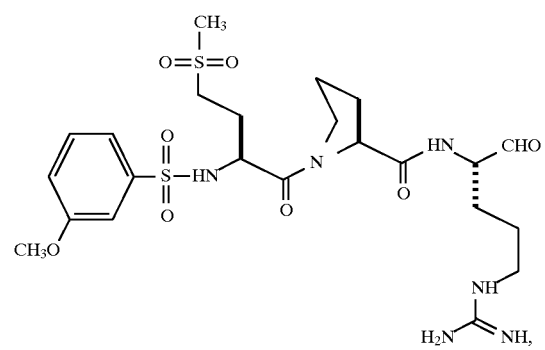
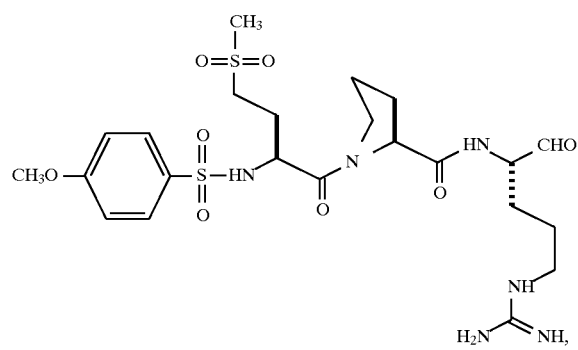 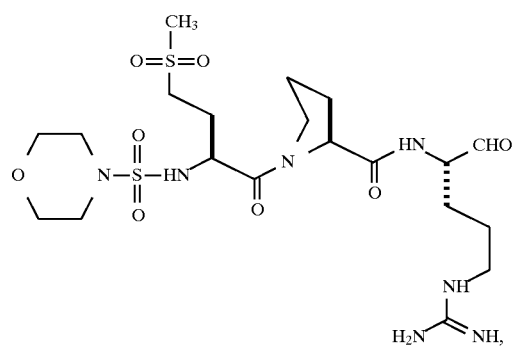
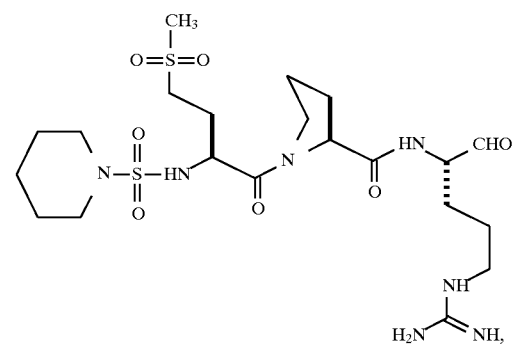 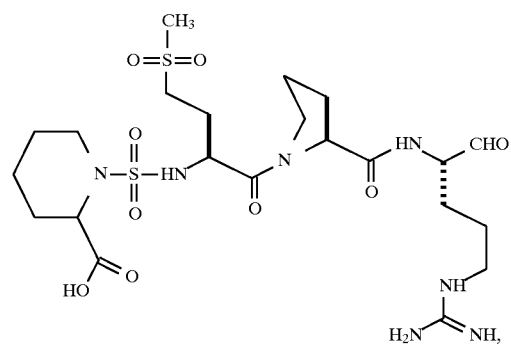

5,770,600
125 126
-continued
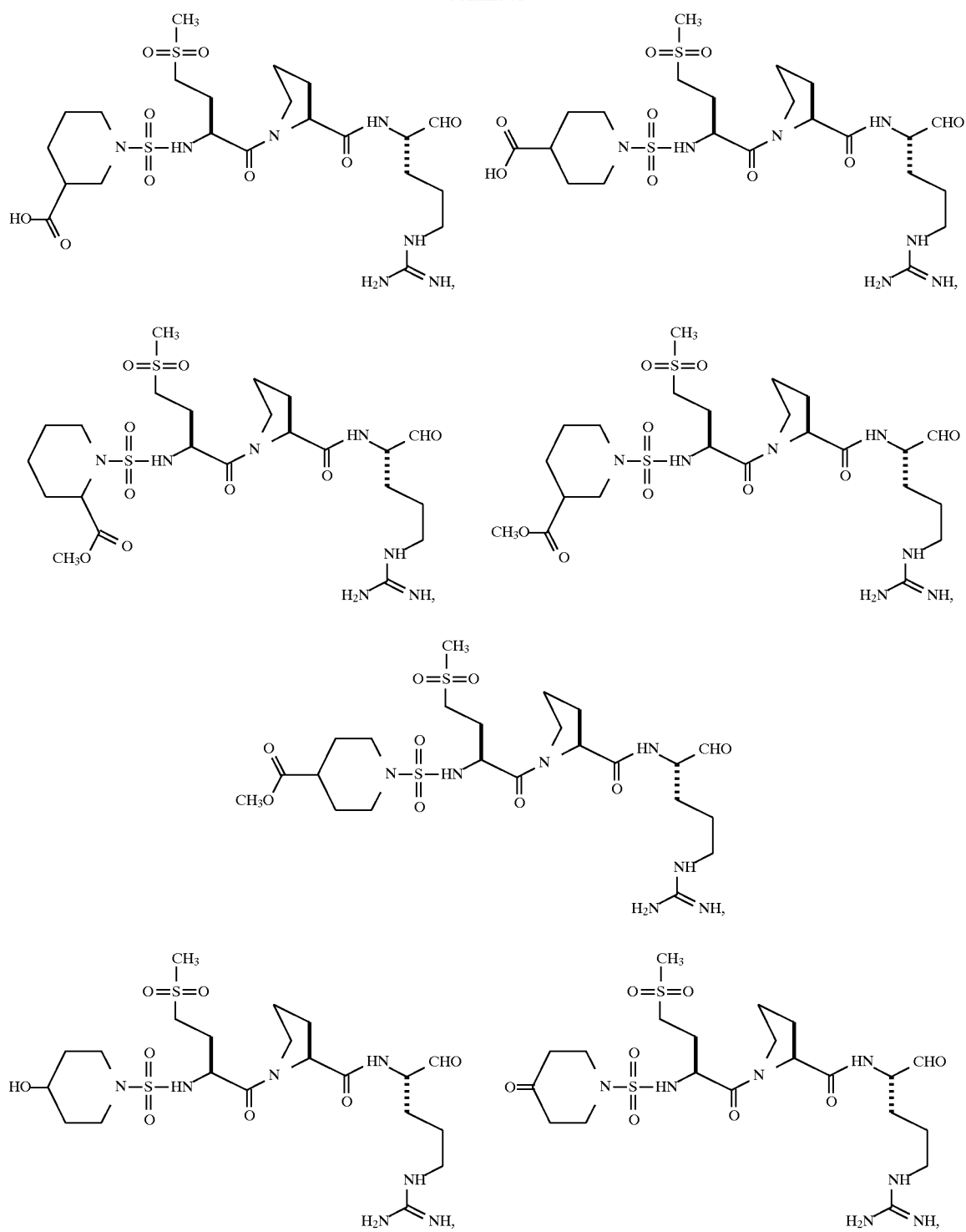

-continued
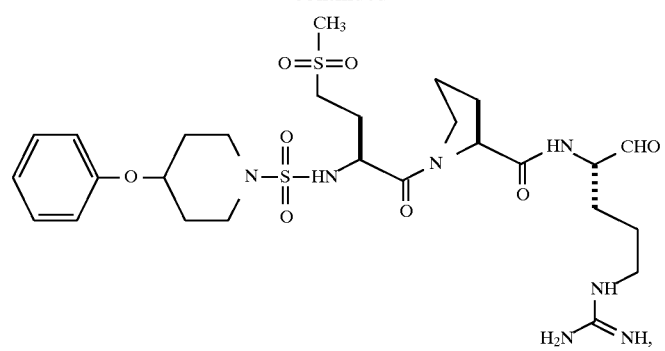
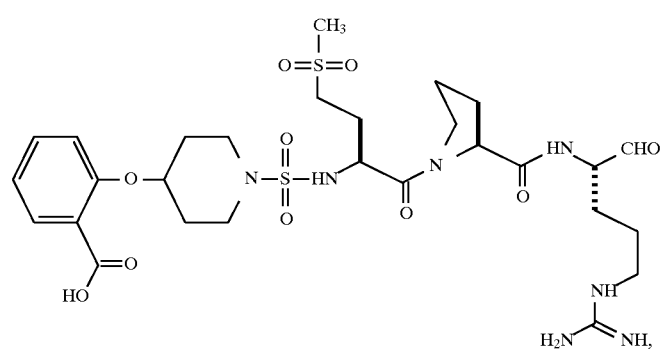
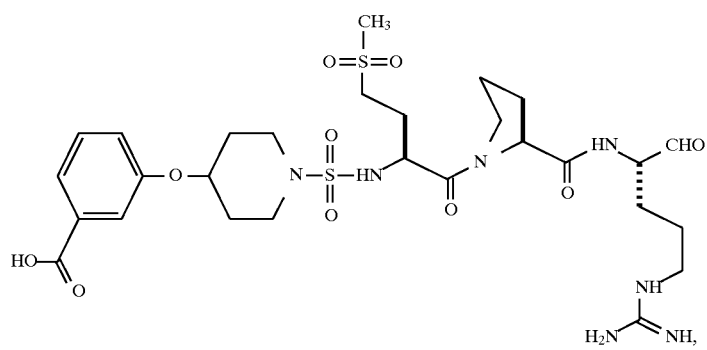
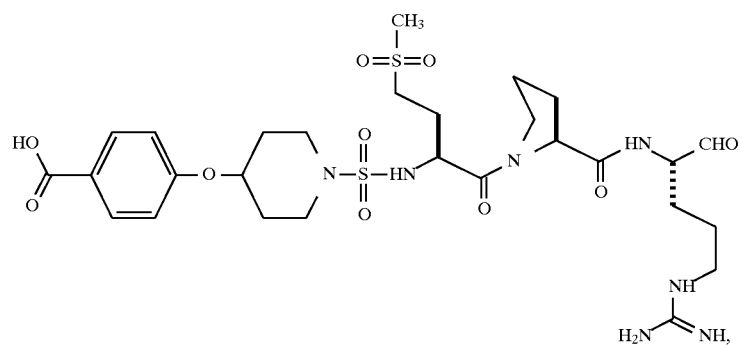

-continued
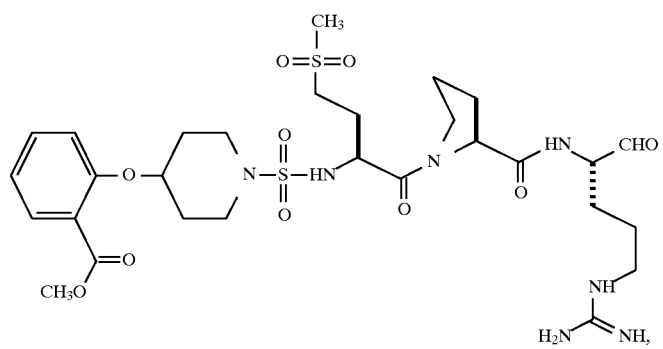
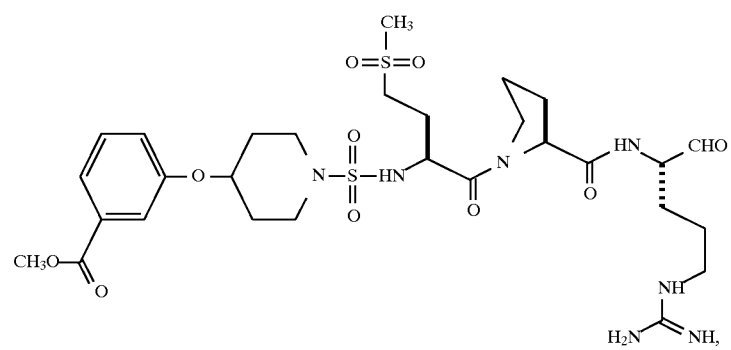
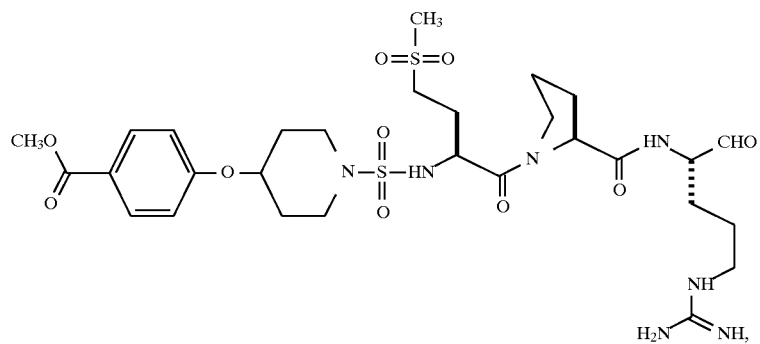
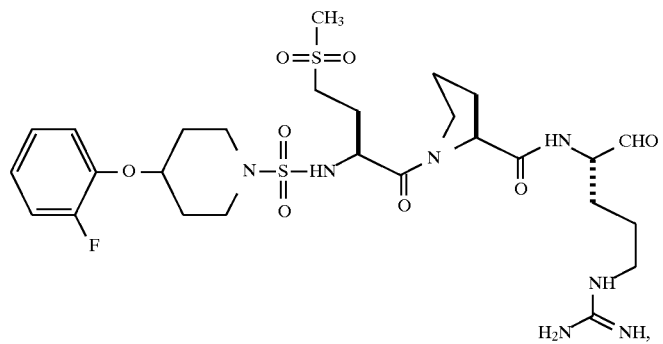

-continued
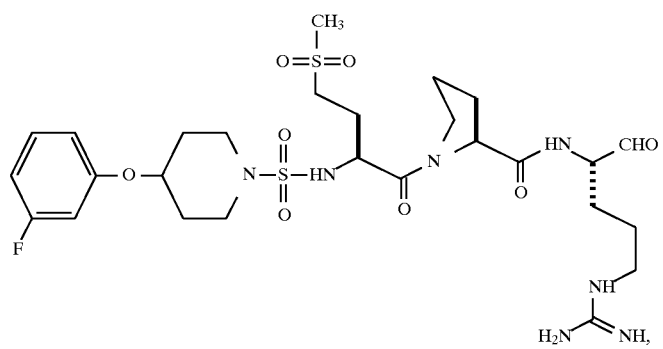
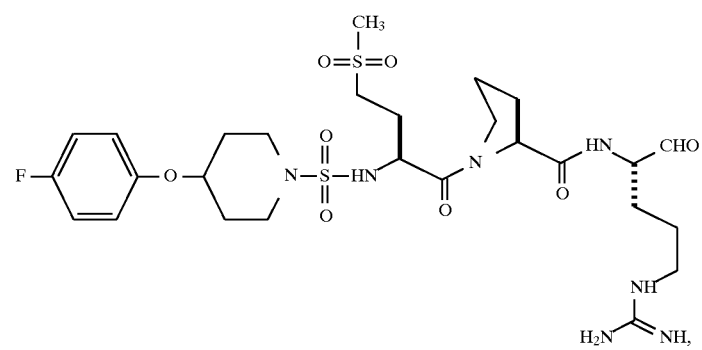
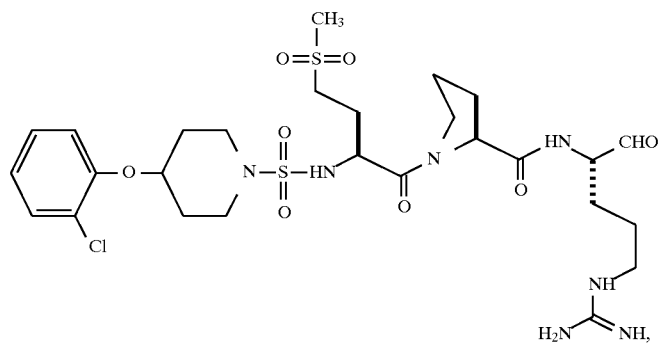
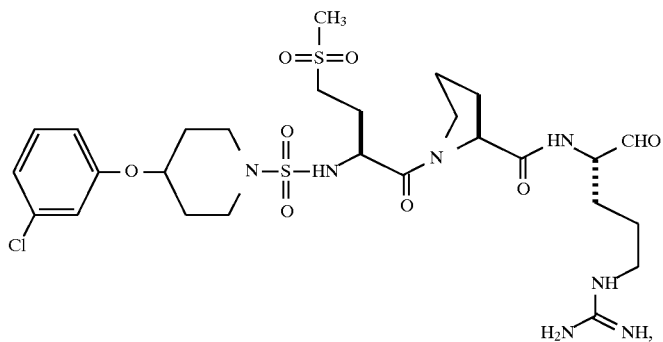

-continued
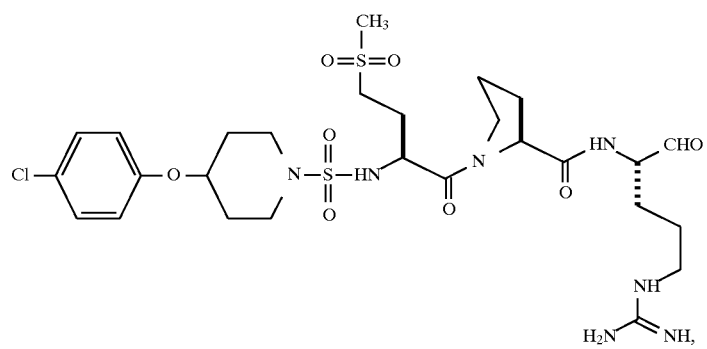
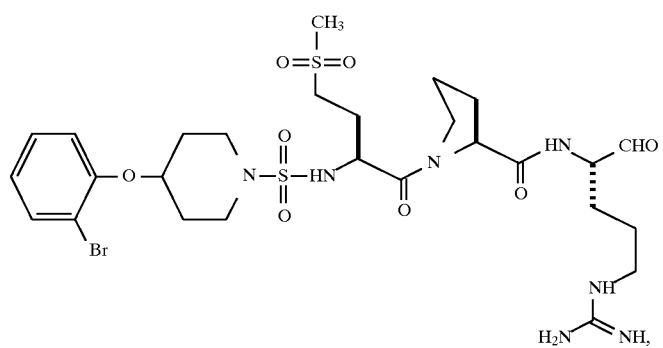
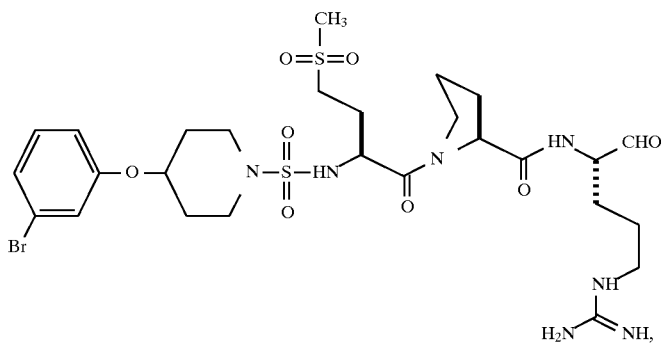
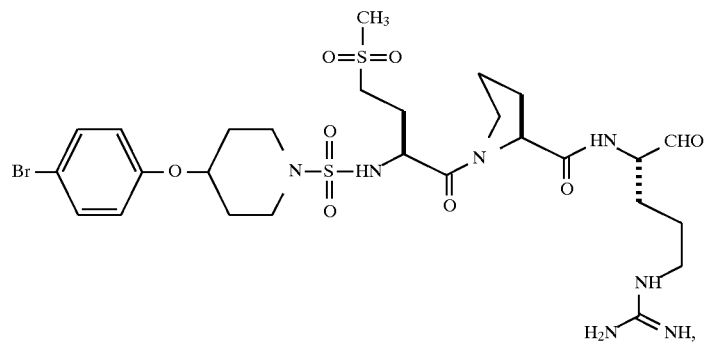

-continued
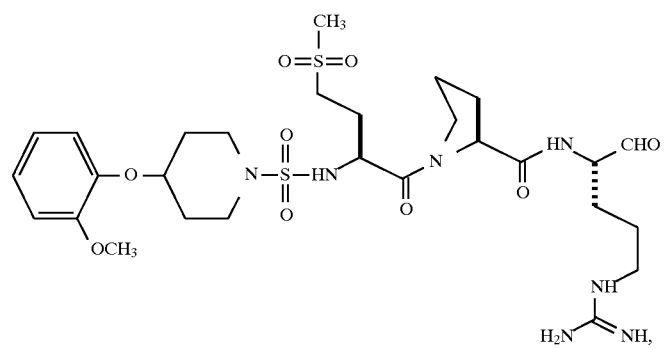
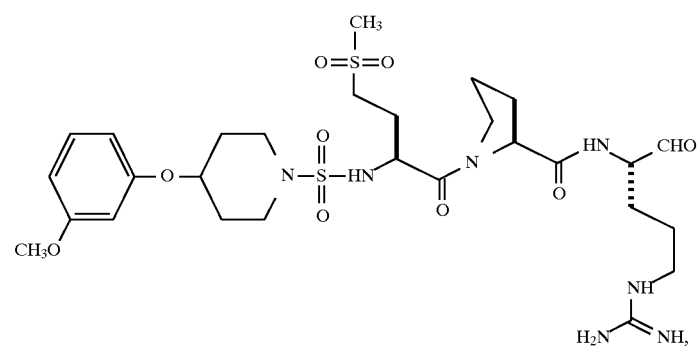
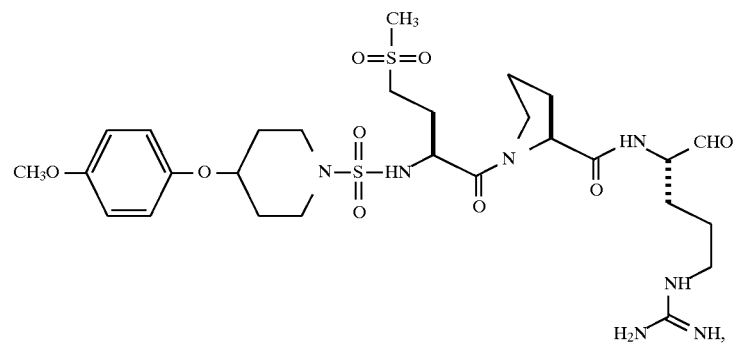
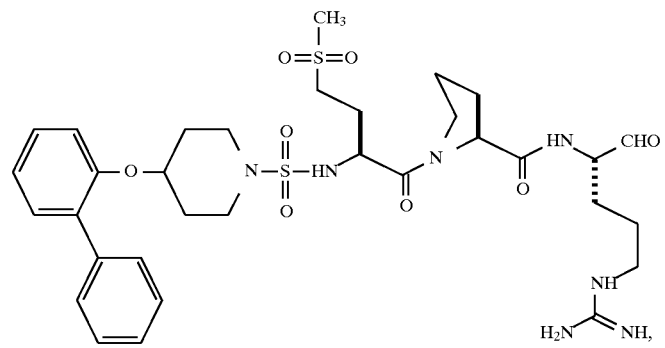

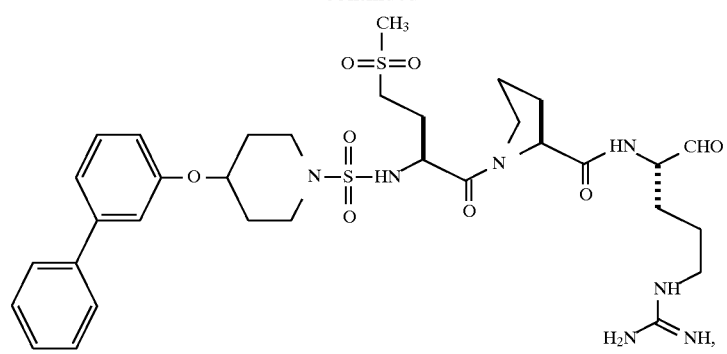
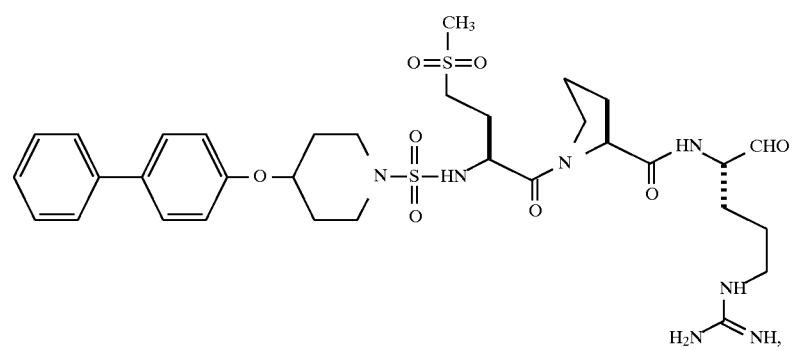
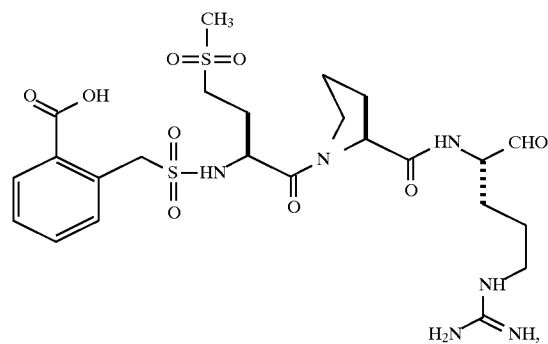
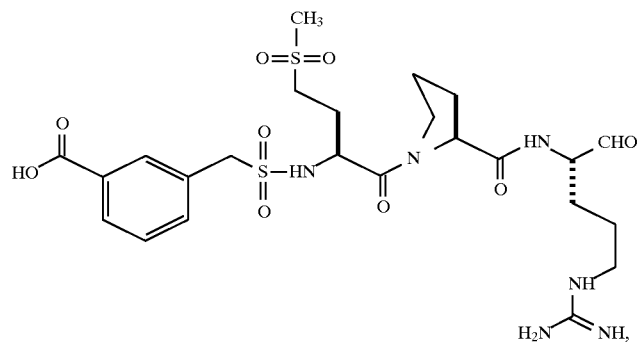

-continued
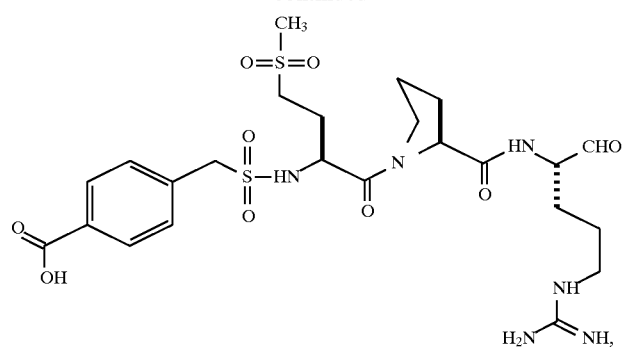
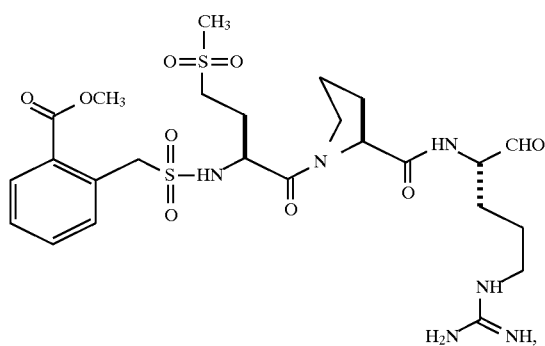
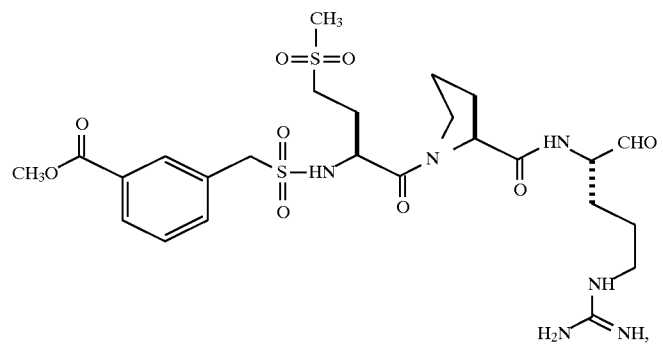
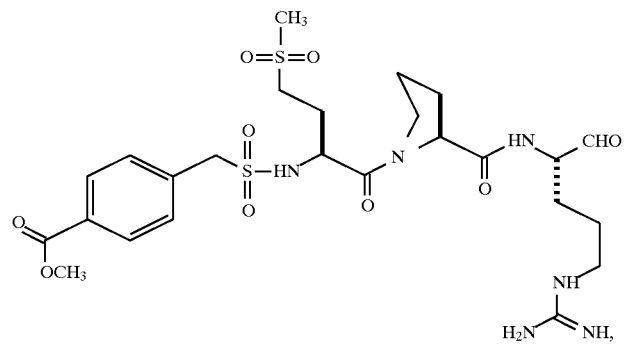

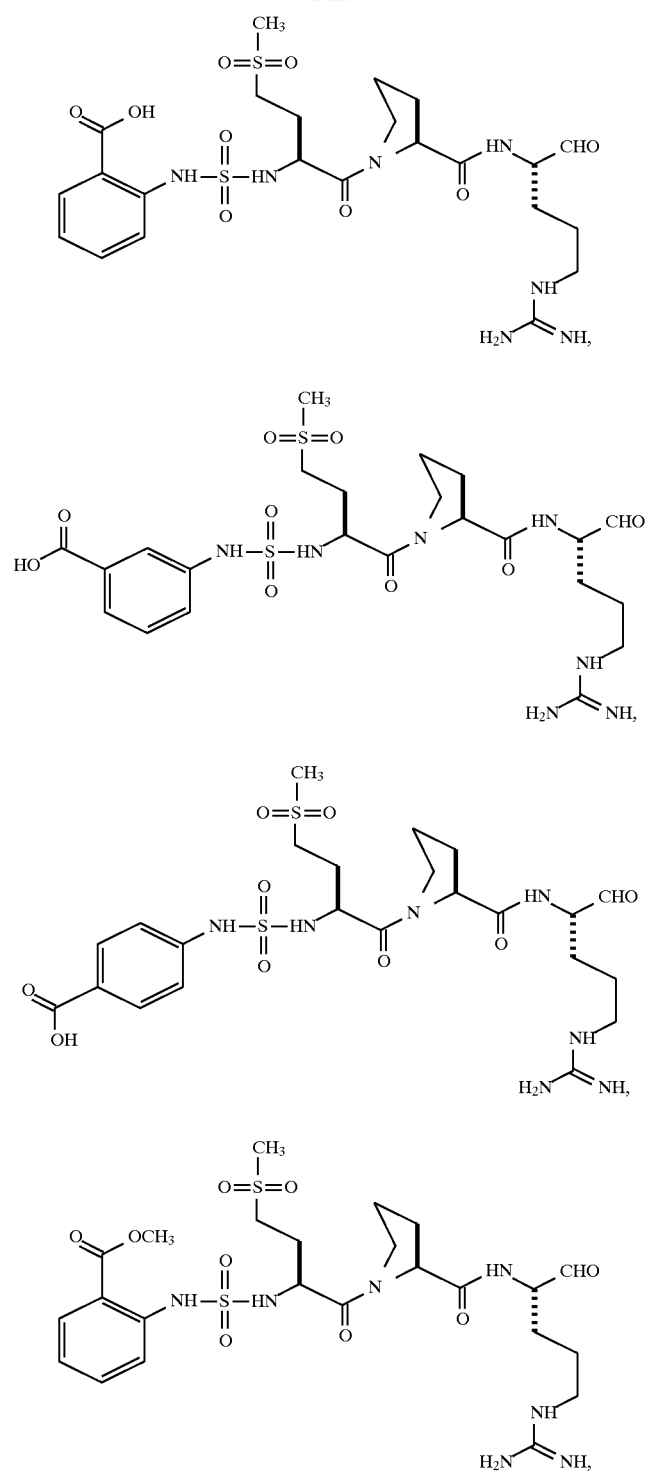

-continued

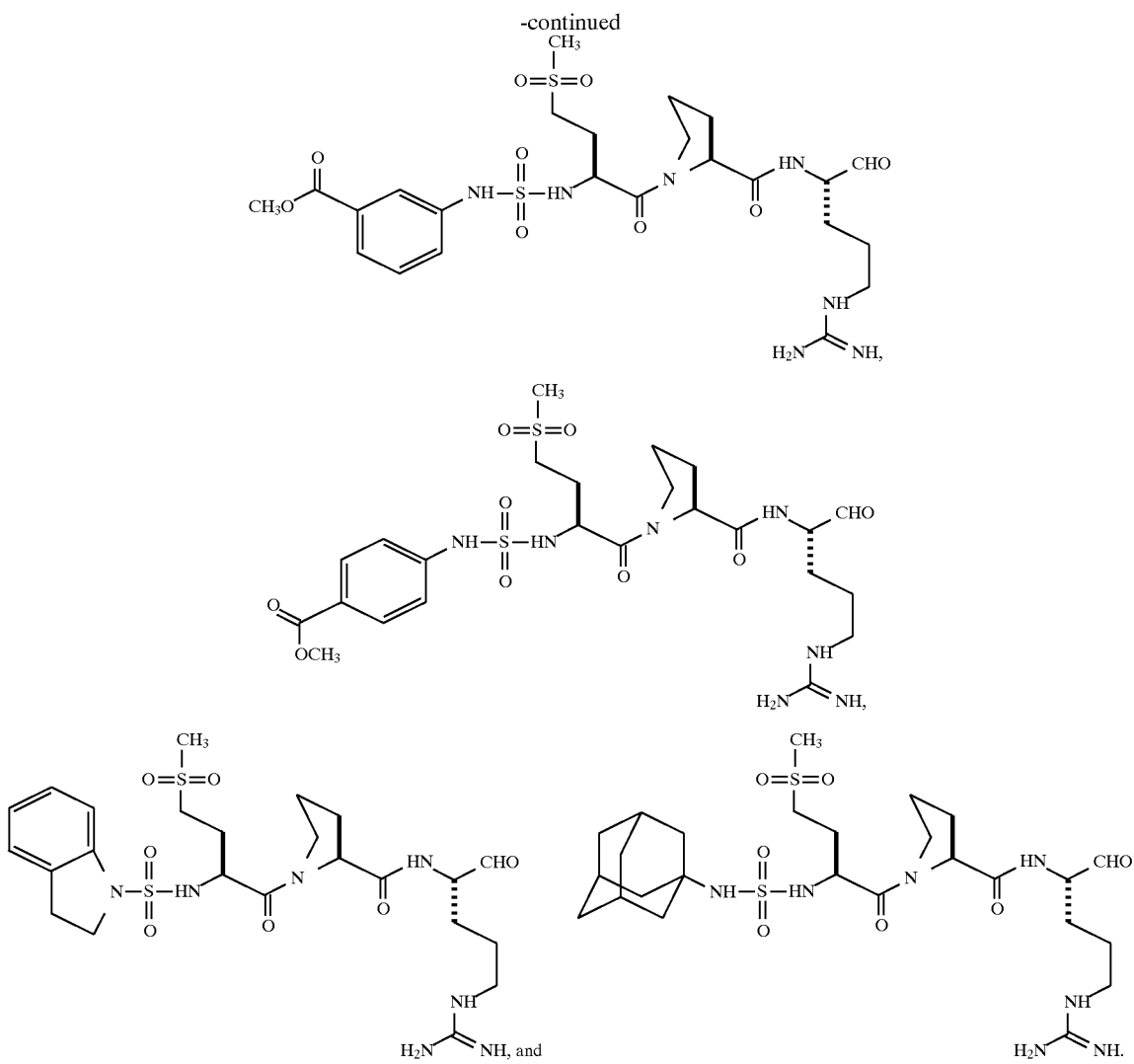

Kinetic Analysis of Selected Compounds in an in vitro Thrombin Inhibition Assay

1. Determination of $IC_{50}$

The ability of the compounds of the present invention to act as inhibitors of thrombin and plasmin catalytic activity was assessed by determining the concentration which inhibited enzyme activity by 50%, ($IC_{50}$), using the purified human enzymes.

The buffer used for all assays was HBSA (10 mM HEPES, pH 7.5, 150 mM sodium chloride, 0.1% bovine serum albumin).

The assay for $IC_{50}$ determinations was conducted by combining in appropriate wells of a Corning microtiter plate, 50 microliters of HBSA, 50 microliters of the test compound at a specified concentration (covering a broad concentration range) diluted in HBSA (or HBSA alone for $V_o$ (uninhibited velocity) measurement), and 50 microliters of the enzyme diluted in HBSA. Following a 30 minute incubation at ambient temperature, 50 microliters of the substrate at the concentrations specified below, was added to the wells yielding a final total volume of 200 microliters. The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value.

Thrombin Assay

Thrombin catalytic activity was determined using the chromogenic substrate Pefachrome t-PA ($CH_3SO_2$-D-hexahydrotyrosine-glycyl-L-arginine-p-nitroaniline, obtained from Pentapharm Ltd.). The substrate was made up in deionized water followed by dilution in HBSA prior to the assay in which the final concentration was 300 $\mu$M (about 10-times Km). Purified human alpha-thrombin was obtained from Enzyme Research Laboratories, Inc. The enzyme was diluted into HBSA prior to the assay in which the final concentration was 0.25 nM.

Factor Xa Assay

Factor Xa catalytic activity was determined using the substrate, S2765 (N-alpha-benzyloxycarbonyl-D-argininyl-L-glycyl-L-arginine-p-nitroanilide dihydrochloride) which was obtained from Kabi Diagnostica. The substrate was made up in deionized water followed by dilution in HBSA prior to the assay in which the final concentration was 250 $\mu$M (about 5-times Km). Human factor Xa was prepared from purified human factor X obtained from Enzyme Research Laboratories according to the method described by Bock, P. E. et al., Archives of Biochem. Biophys. 273: 375

(1989). The enzyme was diluted into HBSA prior to the assay in which the final concentration was 0.5 nM.

Plasmin Assay

Plasmin catalytic activity was determined using the chromogenic substrate, S-2251 [D-valyl-L-leucyl-L-lysine-p-nitroanilide dihydrochloride], which was obtained from Kabi Diagnostica. The substrate was made up in deionized water followed by dilution in HBSA prior to the assay in which the final concentration was 300 μM (about 5-times Km). Purified human plasmin was obtained from Enzyme Research Laboratories, Inc. The enzyme was diluted into HBSA prior to assay in which the final concentration was 1.0 nM.

Table I below gives the $IC_{50}$ values for thrombin and plasmin for selected test compounds of the present invention.

of 0.5 nM in a total volume of 200 microliters. Velocities of chromogenic substrate hydrolysis which occurred over 40 minutes was measured by the change in absorbance at 405 nm using a Thermo Max® Kinetic Microplate Reader.

Ki values were determined for test compounds using the relationships developed by Williams and Morrison, Methods in Enzymology, 63: 437 (1979) using steady state velocities (Vs) measured over 40 minutes. The extent of substrate hydrolysis was less than 5% over the course of this assay.

Table 2 below gives the Ki values for selected test compounds. The data shows their utility as potent in vitro inhibitors of human alpha-thrombin.

TABLE 1

$IC_{50}$ of Preferred Compounds.

| Compound Tested | From Example | IC50, micromolar Thrombin | Plasmin |
|---|---|---|---|
| BuSO$_2$—Met[S(O$_2$)]—Pro—Arg-al | 11 | 0.0016 | 0.199 |
| ChxCH$_2$SO$_2$—Met[S(O$_2$)]—Pro—Arg-al | 18 | 0.00066 | 0.030 |
| 2-CMPhSO$_2$—Met[S(O$_2$)]—Pro—Arg-al | — | 0.00081 | 0.20 |
| 1-NpSO$_2$—Met[S(O$_2$)]—Pro—Arg-al | 21 | 0.00078 | >0.025 |
| 2-NpSO$_2$—Met[S(O$_2$)]—Pro—Arg-al | 24 | 0.00058 | 0.035 |
| BzlSO$_{2-Met[S(O2)]}$—Pro—Arg-al | 27 | 0.0010 | 0.086 |
| d-Camphor-SO$_2$—Met[S(O$_2$)]—Pro—Arg-al | — | 0.0026 | 0.030 |
| ChxNH—SO$_2$—Met[S(O$_2$)]—Pro—Arg-al | — | 0.146 | 2.6 |
| 2-PrPen—Met[S(O$_2$)]—Pro—Arg-al | 33 | 0.0055 | 0.50 |
| Bzl—SO$_2$—Cys[S—CH$_2$CO$_2$H]—Pro—Arg-al | — | 0.013 | 0.49 |
| BuSO$_2$—Cys[S(O$_2$)—CH$_3$]—Pro—Arg-al | 40 | 0.0018 | >0.25 |
| 2-PrPen—Cys[S(O$_2$)—CH$_3$]—Pro—Arg-al | 43 | 0.0051 | 2.8 |
| 2-NpSO$_2$—Cys[S(O$_2$)—CH$_3$]—Pro—Arg-al | 46 | 0.0014 | >0.25 |
| 1-NpSO$_2$—Cys[S(O$_2$)—CH$_3$]—Pro—Arg-al | 49 | 0.0031 | 0.25 |
| Bu—SO$_2$—Cys[S(O$_2$)—CH$_2$CO$_2$H]—Pro—Arg-al | — | 0.0030 | 0.11 |
| BzlSO$_2$—Cys[S(O$_2$)—CH$_2$CO$_2$H]—Pro—Arg-al | 56 | 0.013 | 0.49 |
| 2-PrPen—Cys[S(O$_2$)—CH$_2$CO$_2$H]—Pro—Arg-al | 59 | 0.0016 | 0.22 |
| 2-NpSO$_2$—Cys[S(O$_2$)—CH$_2$CO$_2$CH$_3$]—Pro—Arg-al | 69 | 0.00056 | 0.061 |
| Compound of Example 139 | 139 | 0.0017 | 0.25–2.5 |
| Compound of Example 144 | 144 | 0.000742 | 0.388 |

2. Determination of Inhibition constant, Ki

The ability of the compounds of the present invention to act as inhibitors of thrombin catalytic activity was assessed by determining their inhibition constant, Ki.

Enzyme activity was determined using the chromogenic substrate Pefachrome t-PA (CH$_3$SO$_2$-D-hexahydrotyrosine-glycyl-L-arginine-p-nitroaniline), obtained from Pentapharm Ltd. The substrate was reconstituted in deionized water prior to use. Purified human alphathrombin (3000 U/mg specific activity) was obtained from Enzyme Research Laboratories, Inc. The buffer used for all assays was HBSA (10 mM HEPES, pH 7.5, 150 mM sodium chloride, 0.1% bovine serum albumin).

The assay for Ki determinations was conducted by combining in appropriate wells of a Corning microtiter plate, 50 microliters of HBSA, 50 microliters of the test compound at a specified concentration diluted in HBSA (or HBSA alone for Vo(uninhibited velocity) measurement), and 50 microliters of the chromogenic substrate (250 micromolar, 5×Km) At time zero, 50 microliters of alpha-thrombin diluted in HBSA, was added to the wells yielding a final concentration

TABLE 2

Inhibitor Constants (Ki) of Preferred Compounds.

| Compound | Ki (nM) |
|---|---|
| 2-Prpen—Met[S(O$_2$)]—Pro—Arg-al[1] | 4.0 |
| 2-NpSO$_2$—Met[S(O$_2$)]—Pro—Arg-al[2] | 0.135 |
| BzlSO$_2$—Met[S(O$_2$)]—Pro—Arg-al[3] | 1.06 |

[1]This is the compound of Example 33.
[2]This is the compound of Example 24.
[3]This is the compound of Example 27.

Example B

Ex vivo Anticoagulant Effects of BzlSO$_2$-Met[S(O$_2$)]-Pro-Arg-al in Rat and Human Plasma The ex vivo anticoagulant effects of BzlSO$_2$-Met[S(O$_2$)]-Pro-Arg-al was determined by measuring the prolongation of the activated partial thromboplastin time (APTT) over a broad concentration range of the added inhibitor, using pooled normal human and rat plasma. Fresh frozen citrated pooled normal human plasma was obtained from George King Biomedical, Overland Park, Kans. Pooled normal rat plasma was prepared from citrated whole blood collected from anesthetized rats using standard procedures. The plasma was flash frozen and stored at −80° C. until use. Measurements APTT was made using the Coag-A-Mate RA4 automated coagulometer (General Diagnostics, Organon Technica, Oklahoma City, Okla.) using the Automated APTT reagent (Organon Technica, Durham, N.C.) as the initiator of clotting according to the manufacturer's instructions.

The assay was conducted by making a series of dilutions of the test compounds in rapidly thawed plasma followed by adding 200 microliters to the wells of the assay carousel.

FIG. 2 shows the anticoagulant effect of $BzlSO_2$-Met[S$(O_2)$]-Pro-Arg-al was measured in citrated rat (●) and human (○) plasma using this activated partial thromboplastin time (APTT) assay. The elevation in APTT due to increasing concentration of compound is presented relative to the control clotting time for rat (19.75 sec) and human (28.3 sec) plasma which is set to a value of 1.0. It is clear from these data that $BzlSO_2$-Met[S$(O_2)$]-Pro-Arg-al prolonged the APTT in a dose dependent manner in both rat and human plasma indicating a similar anticoagulant effect in both species of mammals.

Example C
Evaluation of the Antithrombotic Potential of $BzlSO_2$-Met[S$(O_2)$]-Pro-Arg-al in an Experimental Rat Model of Thrombosis The demonstrated anticoagulant effects of $BzlSO_2$-Met[S$(O_2)$]-Pro-Arg-al in both rat and human citrated plasma indicated that this compound may have potent antithrombotic effects in an experimental model of thrombosis performed in rats. To investigate this, the antithrombotic (prevention of thrombus formation) properties of this compound was evaluated using the following established experimental model of acute vascular thrombosis.

Rat model of $FeCl_3$-induced platelet-dependent arterial thrombosis

This is a well characterized model of platelet dependent, arterial thrombosis which has been used in the evaluation potential antithrombotic compounds such as direct thrombin inhibitors. Kurz, K. D., Main, B. W., and Sandusky, G. E., Thromb. Res., 60: 269–280 (1990). In this model a platelet-rich, occlusive thrombus is formed in a segment of the rat carotid artery treated locally with a fresh solution of $FeCl_3$ absorbed to a piece of filter paper. The $FeCl_3$ is thought to diffuse into the treated segment of artery and causes de-endothelialization of the affected vessel surface. This results in the exposure of blood to subendothelial structures which in turn causes platelet adherence, thrombin formation and platelet aggregation resulting in occlusive thrombus formation. The effect of a test compound on the incidence of occlusive thrombus formation following the application of the $FeCl_3$ is monitored by ultrasonic flowtometry and is used as the primary end point. The use of flowtometry to measure carotid artery blood flow, is a modification of the original procedure in which thermal detection of clot formation was employed. Kurz, K. D., Main, B. W., and Sandusky, G. E., Thromb. Res., 60: 269–280 (1990).

Male Harlan Sprague Dawley rats (420–450 g) were acclimated at least 72 hours prior to use and fasted for 12 hours prior to surgery with free access to water. The animals were prepared, anesthetized with Nembutal followed by the insertion of catheters for blood pressure monitoring, drug and anesthesia delivery. The left carotid artery was isolated by making a midline cervical incision followed by blunt dissection and spreading techniques to separate a 2 cm segment of the vessel from the carotid sheath. A silk suture was inserted under the proximal and distal ends of the isolated vessel to provide clearance for the placement of a ultrasonic flow probe (Transonic) around the proximal end of the vessel. The probe was then secured with a stationary arm.

Following surgery the animals were randomized in either a control (saline) or treatment group with test compound ($BzlSO_2$-Met[S$(O_2)$]-Pro-Arg-al) with at least 6 animals per group per dose. The test compound was administered as a single intravenous bolus at the doses outlined in Table 3 after placement of the flow probe and 5 minutes prior to the application of the $FeCl_3$ thrombogenic stimulus (t=0). At t=0, a 3 mm diameter piece of filter paper (Whatman #3) soaked with 10 microliters of a 35% solution of fresh $FeCl_3$ (made up in water) was applied the segment of isolated carotid artery distal to the flow probe. Blood pressure, blood flow, heart rate, and respiration were monitored for 60 minutes.

The incidence of occlusion (defined as the attainment of zero blood flow) was recorded as the primary end point.

The efficacy of $BzlSO_2$-Met[S$(O_2)$]-Pro-Arg-al as an antithrombotic agent in preventing thrombus formation in this in vivo model was demonstrated by the reduction in the incidence of thrombotic occlusion as shown in Table 3 below.

TABLE 3

Results of $BzlSO_2$—Met[S$(O_2)$]—Pro—Arg-al
(Test Cmpd) in the $FeCl_3$ Model of Thrombosis in Rats.

| Treatment Group | Dose (mg/kg) | n | Incidence of Occlusion |
|---|---|---|---|
| Saline | — | 6 | 6/6 |
| Test Cmpd | 0.5 | 6 | 6/6 |
| Test Cmpd | 0.75 | 6 | 2/6 |
| Test Cmpd | 1.0 | 6 | 1/6* |
| Test Cmpd | 3.0 | 6 | 0/6* |

*—$p \leq 0.05$ from saline control by Fisher test

The therapeutically effective amount (dose) which prevents 50% of thrombotic occlusions in this model ($ED_{50}$) can be determined from the above data by plotting the incidence of occlusion versus the dose administered. This allows a direct comparison of the antithrombotic efficacy of $BzlSO_2$-Met[S$(O_2)$]-Pro-Arg-al with other antithrombotic agents which have also been evaluated in this model as described above. Table 4 lists the $ED_{50}$ values for several well known anticoagulant agents in this model compared to this compound.

TABLE 4

Efficacy of $BzlSO_2$—Met[S$(O_2)$]—Pro—Arg-al
compared to other antithroinbotic agents based on $ED_{50}$ for
thrombus prevention in the $FeCl_3$ model of arterial thrombosis.

| Compound | Ki (nM) | $ED_{50}$[b] (mg/kg) |
|---|---|---|
| Standard Heparin | | 300 U/kg |
| Argatroban | 19.0[c] | 3.8 mg/kg |
| Hirulog ™ | 2.56[d] | 3.0 mg/kg |
| $BzlSO_2$—Met[S$(O_2)$]—Pro—Arg-al | 1.06[a] | 0.7 mg/kg |

[a]Ki determined using human alpha-thrombin as described above and in items c and d
[b]$ED_{50}$ is defined as the dose that prevents the incidence of complete thrombotic occlusion in 50% of animals tested
[c]Kikumoto, R. et. al. Biochemistry 23: 85–90 (1984)
[d]Witting, J. I. et. al. Biochem. J. 283: 737–743 (1992)

The data presented in Table 4 clearly demonstrates the effectiveness of $BzlSO_2$-Met[S$(O_2)$]-Pro-Arg-al in preventing occlusive thrombus formation in this experimental model. The relevance of this data to preventing human thrombosis can be inferred from the comparison to the other anticoagulant agents listed in this table which have been evaluated in an identical manner in this experimental model and have demonstrated antithrombotic efficacy in preventing thrombus formation clinically as described in the following literature citations: Heparin-Hirsh, J. N. Engl., J. Med 324:1565–1574 (1992) and Cairns, J. A. et. al., Chest, 102: 456S–481S (1992); Argatroban-Gold, H. K. et. al., J. Am. Coll. Cardiol., 21: 1039–1047 (1993); and Hirulog™-Sharma, G. V. R. K. et.al., Am. J. Cardiol., 72: 1357–1360 (1993) and Lidón, R. M. et.al., Circulation, 88: 1495–1501 (1993).

The in vivo comparison of $BzlSO_2$-Met[$S(O_2)$]-Pro-Arg-al with the clinically effective antithrombotic agents Heparin, Argatroban, and Hirulog™ in the same rodent model of experimental thrombosis coupled with the demonstrated anticoagulant effects of $BzlSO_2$-Met[$S(O_2)$]-Pro-Arg-al in both rat and human plasma described above in Example B clearly suggests that this compound will be an effective antithrombotic agent in humans.

We claim:

1. A compound of the formula:

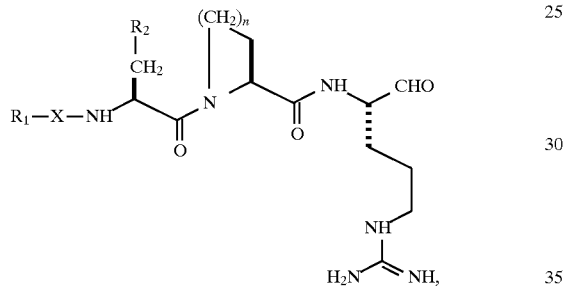

wherein (a) X is selected from the group consisting of —C(O)—, —O—C(O)—, —NH—C(O)—, —S($O_2$)—, —O—S($O_2$)—, —NH—S($O_2$)— and —N(R')—S($O_2$)—, wherein R' is alkyl of 1 to about 4 carbon atoms, aryl of about 6 to about 14 carbon atoms, or aralkyl of about 6 to about 15 carbon atoms;

(b) $R_1$ is selected from the group consisting of:

(1)

wherein W is methylene, —C(O)—, —CH(OH)—, —CH($OA_1$)—, —CH(C(O)—OH)—, —CH(C(O)—OR')—, —CH(C(O)—NHR')—, —CH(C(O)—NR'R")—, or

where X is not —O—C(O)—, NH—C(O)—, —O—S($O_2$)—, —NH—S($O_2$)— or —N(R')—S($O_2$)—, (2)

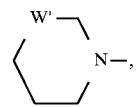

wherein W' is methylene, —C(O)—, —CH(OH)—, —CH($OA_1$)—, —CH(C(O)—OH)—, —CH(C(O)—OR')—, —CH(C(O)—NHR')—, —CH(C(O)—NR'R")—, or

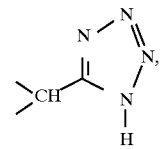

where X is not —O—C(O)—, NH—C(O)—, —O—S($O_2$)—, —NH—S($O_2$)— or —N(R')—S($O_2$)—, and (3)

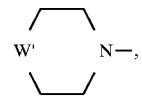

wherein W' is oxygen, methylene, —C(O)—, —CH(OH)—, —CH($OA_1$)—, —CH(C(O)—OH)—, —CH(C(O)—OR')—, —CH(C(O)—NHR')—, —CH(C(O)—NR'R")—, or

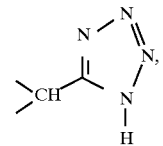

where X is not —O—C(O)—, NH—C(O)—, —O—S($O_2$)—, —NH—S($O_2$)— or —N(R')—S($O_2$)—, wherein $Y_1$, $Y_2$ and $Y_3$ are independently selected from the group consisting of bromo, chloro, fluoro, —$Z_1$, —OH, —$OZ_1$, —$NH_2$, —$NHZ_1$, —$NZ_1Z_2$, —NH—C(O)—$Z_1$, —N($Z_1$)—C(O)—$Z_2$, —NH—C(O)—$OZ_1$, —N($Z_1$)—C(O)—$OZ_2$, —NH—C(O)—$NH_2$, —NH—C(O)—$NHZ_1$, —NH—C(O)—$NZ_1Z_2$, —N($Z_1$)—C(O)—$NHZ_2$, —N($Z_1$)—C(O)—$NZ_2Z_3$, —C(O)—OH, —C(O)—$OZ_1$, —C(O)—$NHZ_1$, —C(O)—$NZ_1Z_2$, —SH, —$SZ_1$, —S(O)—$Z_1$, —S($O_2$)—$Z_1$, —S($O_2$)—OH, —S($O_2$)—$OZ_1$, —S($O_2$)—$NH_2$, —S($O_2$)—$NHZ_1$, —S($O_2$)—$NZ_1Z_2$ and

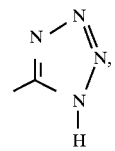

wherein $Z_1$, $Z_2$ and $Z_3$ are independently selected from the group consisting of trifluoromethyl, pentafluoroethyl, alkyl of 1 to about 12 carbon atoms, aryl of about 6 to about 14 carbon atoms, and aralkyl of about 6 to about 15 carbon atoms, R" is alkyl of 1 to about 4 carbon atoms, aryl of about 6 to about 14 carbon atoms, or aralkyl of about 6 to about 15 carbon atoms, $A_1$ is aryl of about 6 to about 14 carbon atoms, aryl of about 6 to about 14 carbon atoms which is substituted with $Y_1$, aralkyl of about 6 to about 15 carbon atoms, or aralkyl of about 6 to about 15 carbon atoms which is substituted with $Y_1$;

(c) $R_2$ is selected from the group consisting of
—$CH_2$—$S(O)_q$—$CH_3$,
—$CH_2$—$S(O)_q$—$(CH_2)_m$—$C(O)$—OH,
—$CH_2$—$S(O)_q$—$(CH_2)_m$—$C(O)$—OR',
—$CH_2$—$S(O)_q$—$(CH_2)_m$—$C(O)$—$NH_2$,
—$CH_2$—$S(O)_q$—$(CH_2)_m$—$C(O)$—NHR',
—$CH_2$—$S(O)_q$—$(CH_2)_m$—$C(O)$—NR'R",

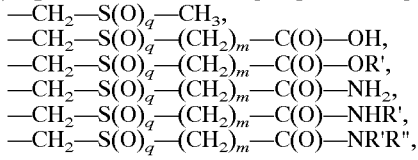

—$CH_2$—$S(O)_q$—$(CH_2)_m$—Ar—C(O)OH,
—$CH_2$—$S(O)_q$—$(CH_2)_m$—Ar—C(O)OR',
—$CH_2$—$S(O)_q$—$(CH_2)_m$—Ar—C(O)$NH_2$,
—$CH_2$—$S(O)_q$—$(CH_2)_m$—Ar—C(O)NHR',
—$CH_2$—$S(O)_q$—$(CH_2)_m$—Ar—C(O)NR'R",
—$CH_2$—$S(O)_q$—$(CH_2)_m$—Ar—[$CHN_4$]$CN_4$H,
—$S(O)_q$—$CH_3$,
—$S(O)_q$—$(CH_2)_m$—C(O)—OH,
—$S(O)_q$—$(CH_2)_m$—C(O)—OR',
—$S(O)_q$—$(CH_2)_m$—C(O)—$NH_2$,
—$S(O)_q$—$(CH_2)_m$—C(O)—NHR',
—$S(O)_q$—$(CH_2)_m$—C(O)—NR'R",

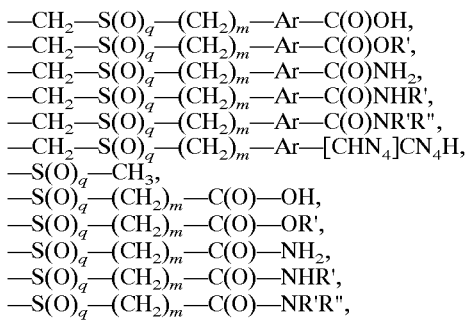

—$S(O)_q$—$(CH_2)_m$—Ar—C(O)OH,
—$S(O)_q$—$(CH_2)_m$—Ar—C(O)OR',
—$S(O)_q$—$(CH_2)_m$—Ar—C(O)$NH_2$,
—$S(O)_q$—$(CH_2)_m$—Ar—C(O)NHR',
—$S(O)_q$—Ar—C(O)NR'R", and
—$S(O)_q$—Ar—[$CHN_4$]$CN_4$H, wherein m is 1, 2, 3, 4, 5 or 6; q is 0, 1 or 2 and Ar is a divalent aryl group of 6 to 14 carbon atoms and (d) n is 1, 2 or 3; or pharmaceutically acceptable salts thereof.

2. A compound of claim 1, wherein n is 2.

3. A compound of claim 2, wherein $R_2$ is —$CH_2$—$S(O_2)$—$CH_3$.

4. A compound of claim 3, wherein X is —$S(O_2)$— or —C(O)—.

5. A compound of claim 4, wherein X is —$S(O_2)$—.

6. A compound of claim 4, wherein X is —C(O)—.

7. A compound of claim 2, wherein $R_2$ is —$S(O_2)$—$CH_3$.

8. A compound of claim 7, wherein X is —$S(O_2)$— or —C(O)—.

9. A compound of claim 8, wherein X is —$S(O_2)$—.

10. A compound of claim 2, wherein $R_2$ is —$S(O_2)$—$CH_2$—C(O)—OH.

11. A compound of claim 10, wherein X is —$S(O_2)$— or —C(O)—.

12. A compound of claim 11, wherein x is —$S(O_2)$—.

13. A compound of claim 11, wherein X is —C(O)—.

14. A compound of claim 2, wherein $R_2$ is —$S(O_2)$—$CH_2$—C(O)—OR'.

15. A compound of claim 14, wherein R' is methyl, ethyl or propyl.

16. A compound of claim 15, wherein R' is methyl.

17. A compound of claim 16, wherein X is —$S(O_2)$— or —C(O)—.

18. A compound of claim 17, wherein X is —$S(O_2)$—.

19. A compound of claim 17, wherein X is —C(O)—.

20. A compound of claim 2 wherein X is —$S(O_2)$— or —C(O)—.

21. A compound of claim 20 wherein $R_2$ is —S(O)q—$(CH_2)$m—Ar—C(O)OH, —S(O)q—$(CH_2)$m—Ar—C(O)OR', —S(O)q—$(CH_2)$m—Ar—C(O)$NH_2$, —S(O)q—$(CH_2)$m—Ar—C(O)—NHR', —S(O)q—$(CH_2)$m—Ar—C(O)—NHR'R", or, —S(O)q—$(CH_2)$m—Ar—C(O)—$CHN_4$.

22. A pharmaceutical composition for the prevention of thrombosis in a mammal suspected of having a condition of abnormal thrombosis, comprising a pharmaceutically acceptable carrier and a therapeutically effective amount of the compound of claim 1.

23. A method for the prevention of thrombosis in a mammal suspected of having a condition of abnormal thrombosis, comprising administering to said mammal a therapeutically effective amount of the compound of claim 1.

24. A method for the prevention of thrombosis in a mammal suspected of having a condition of abnormal thrombosis, comprising administering to said mammal a therapeutically effective amount of a pharmaceutical composition of claim 22.

* * * * *